US012329806B2

(12) United States Patent
Tavassi et al.

(10) Patent No.: US 12,329,806 B2
(45) Date of Patent: Jun. 17, 2025

(54) COMPOUND FOR MODULATING RLR, TLR, OAS AND/OR ONCOSTATIN M PATHWAYS, USE THEREOF FOR PREPARING A MEDICINE, COMPOSITION, METHOD FOR MODULATING SAID PATHWAYS AND METHOD OF TREATMENT

(71) Applicant: Instituto Butantan, São Paulo-SP (BR)

(72) Inventors: Ana Marisa Chudzinski Tavassi, São Paulo-SP (BR); Roger Chammas, São Paulo-SP (BR); Maurício Barbugiani Goldfeder, São Paulo-SP (BR); Carlos Deocesano Pereira, São Paulo-SP (BR); Flávio Linchtenstein, São Paulo-SP (BR); Jean Gabriel De Souza, São Paulo-SP (BR); Katia Luciano Pereira Morais, São Paulo-SP (BR)

(73) Assignee: Instituto Butantan, São Paulo-SP (BR)

( * ) Notice: Subject to any disclaimer, the term of this patent is extended or adjusted under 35 U.S.C. 154(b) by 1010 days.

(21) Appl. No.: 17/296,090

(22) PCT Filed: Nov. 22, 2019

(86) PCT No.: PCT/BR2019/050502
§ 371 (c)(1),
(2) Date: Oct. 28, 2021

(87) PCT Pub. No.: WO2020/102875
PCT Pub. Date: May 28, 2020

(65) Prior Publication Data
US 2022/0370577 A1 Nov. 24, 2022

(30) Foreign Application Priority Data
Nov. 22, 2018 (BR) .......................... 102018074043-1

(51) Int. Cl.
A61K 38/10 (2006.01)
A61K 38/57 (2006.01)
A61K 38/00 (2006.01)

(52) U.S. Cl.
CPC .............. *A61K 38/57* (2013.01); *A61K 38/00* (2013.01)

(58) Field of Classification Search
None
See application file for complete search history.

(56) References Cited

U.S. PATENT DOCUMENTS

2006/0058228 A1* 3/2006 Kelly ....................... C07K 7/06
514/19.3

FOREIGN PATENT DOCUMENTS

WO  WO 2008/109976 A1  9/2008

OTHER PUBLICATIONS

Gry, Markus et al, "Correlations between rna and protein expression profiles in 23 human cell lines." BMC Genom. (2009) 10:365.*
Uniprot entry for human cytochrome C, downloaded Sep. 2024.*
Baker, M. E.; "Albumin, steriod hormones and the origin of vertebrates." J. Endocrinol. (2002) 175 p. 121-127.*
Pereira, H. Anne et al, "Cap37, aneutrophil granule derived protein stimulates protein kinase c activity in endothelial cells." J. Leukocyte Biol. (1996) 60 p. 415-422.*
Passarelli, Anna et al; "Immune system and melanoma biolgy: a balance between immunosurveillance and immune escape." Oncotarget (2017) 8(62) p. 106132-106142.*
Akagi, Erica Mie et al., "Pro-apoptotic effects of Amblyomin-X in murine renal cell carcinoma "in vitro"" Biomedicine & Pharmacotherapy, 2012, pp. 64-69, vol. 66.
Anders, Simon et al., "Differential expression analysis for sequence count data" Genome Biology, 2010, pp. 1-12, vol. 11, R106.
Batista, Isabel F. C. et al., "Expressed sequence tags (ESTs) from the salivary glands of the tick Amblyomma cajennense (Acari: Ixodidae)" Toxicon, 2008, pp. 823-834, vol. 51.
Branco, Vania. G. et al., "Amblyomin-X having a Kunitz-type homologous domain, is a noncompetitive inhibitor of FXa and induces anticoagulation in vitro and in vivo" Biochimica et Biophysica Acta, 2016, pp. 1428-1435, vol. 1864.
Carvalho-Costa, Tamires Marielem et al., "Immunosuppressive effects of Amblyomma cajennense tick saliva on murine bone marrow-derived dendritic cells" Parasites & Vectors, 2015, pp. 1-13, vol. 8, No. 22.
Chen, Edward Y. et al., "Enrichr: interactive and collaborative HTML5 gene list enrichment analysis tool" BMC Bioinformatics, 2013, pp. 1-14, vol. 14, No. 128.
Chudzinski-Tavassi, Ana Marisa et al., "A new tick Kunitz type inhibitor, Amblyomin-X, induces tumor cell death by modulating genes related to the cell cycle and targeting the ubiquitin-proteasome system" Toxicon, 2010, pp. 1145-1154, vol. 56.
Chudzinski-Tavassi, Ana Marisa et al., "Tick salivary gland as potential natural source for the discovery of promising antitumor drug candidates" Biomedicine & Pharmacotherapy. 2016, pp. 14-19, vol. 77.
Colonna, Marco "TLR pathways and IFN-regulatory factors: To each its own" Eur. J. Immunol., 2007, pp. 306-309, vol. 37.

(Continued)

*Primary Examiner* — Fred H Reynolds
(74) *Attorney, Agent, or Firm* — Knobbe Martens Olson & Bear LLP

(57) ABSTRACT

The invention falls within the fields of pharmaceutical sciences, immunology and methods of treatment of cancer Methods. More specifically, the invention relates to a compound for modulating one or more innate immune pathways selected from RLR, TLR, OAS and/or oncostatin M, said compound being amblyomin-xor peptides derived from amblyomin-X. Use of said compound for preparing medicines; a pharmaceutical composition comprising said compound, a method for modulating said pathways in vitro and a method of treatment are also described.

3 Claims, 44 Drawing Sheets

Specification includes a Sequence Listing.

(56) References Cited

OTHER PUBLICATIONS

Csárdi, Gábor et al., "The igraph software package for complex network research". InterJournal Complex Systems, 2006, No. 1695.
De Souza, Jean Gabriel et al., "Promising pharmacological profile of a Kunitz-type inhibitor in murine renal cell carcinoma model" Oncotarget, 2016, pp. 62255-62266, vol. 7, No. 38.
Duan, Qiaonan et al., "L1000CDS$^2$: LINCS L1000 characteristic direction signatures search engine" npj Systems Biology and Applications, 2016, pp. 1-12, vol. 16015.
Finn, Robert. D. et al., "The Pfam protein family's database: towards a more sustainable future" Nucleic Acids Research, 2016, pp. D279-D285, vol. 44, Database issue.
Franceschini, Andrea. et al., "STRING v9.1: protein-protein interaction networks, with increased coverage and integration" Nucleic Acids Research, 2013, pp. D808-D815, vol. 41, Database issue.
Jheng, Jia-Rong et al., "ER stress, autophagy, and RNA viruses" frontiers in Microbiology, Aug. 2014, pp. 1-13, vol. 5, Article 388.
Kanehisa, Minoru et al., "KEGG as a reference resource for gene and protein annotation" Nucleic Acids Research, 2015, pp. 1-6.
Kim, Daehwan et al., "HISAT: Hierarchical Indexing for Spliced Alignment of Transcripts" BioRxiv, 2014.
Kuleshov, Maxim. V. et al., "Enrichr: a comprehensive gene set enrichment analysis web server 2016 update" Nucleic Acids Research, 2016, pp. W90-W97, vol. 44, Web Server issue.
Langfelder, Peter et al., "WGCNA: an R package for weighted correlation network analysis" BMC Bioinformatics, 2008, pp. 1-13, vol. 9, No. 559.
Langmead, Ben et al., "Fast gapped-read alignment with Bowtie 2" Nature Methods, Apr. 2012, pp. 357-359, vol. 9, No. 4.
Liao, Yang et al., "The Subread aligner: fast, accurate and scalable read mapping by seed-and-vote" Nucleic Acids Research, 2013, pp. 1-17, vol. 41, No. 10, e108.
Lopes, José Daniel et al., "B-1 cell: the precursor of a novel mononuclear phagocyte with immuno-regulatory properties" Anais da Academia Brasileira de Ciências, 2009, pp. 489-496, vol. 81, No. 3.
Maria, Durvanei Augusto et al. "A novel proteasome inhibitor acting in mitochondrial dysfunction, ER stress and ROS production" Invest. New Drugs, 2013, pp. 493-505, vol. 31.
Mignogna, C. et al., "Innate immunity in cutaneous melanoma" Clinical and Experimental Dermatology, 2017, pp. 243-250, vol. 42.
Mogensen, Trine H. "Pathogen Recognition and Inflammatory Signaling in Innate Immune Defenses" Clinical Microbiology, Apr. 2009, pp. 240-273, vol. 22, No. 2.
Morais, Katia L. P. et al., "Amblyomin-X induces ER stress, mitochondrial dysfunction, and caspase activation in human melanoma and pancreatic tumor cell" Mol. Cell. Biochem. 2016, pp. 119-131, vol. 415.
Öhman, Tina et al., "Actin and RIG-I/MAVS Signaling Components Translocate to Mitochondria upon Influenza A Virus Infection of Human Primary Macrophages" Journal of Immunology, 2009, pp. 5682-5692, vol. 182.
Pacheco, Mario T. F. et al., "Dynein Function and Protein Clearance Changes in Tumor Cells Induced by a Kunitz-Type Molecule, Amblyomin-X" PLoS ONE, Dec. 2014, pp. 1-20, vol. 9, No. 12, e111907.
Pfaffl, Michael W. et al., "A new mathematical model for relative quantification in real-time RT-PCR" Nucleic Acids Research, 2001, pp. 2002-2007, vol. 29, No. 9.
Rissi, Daniel Ricardo et al., "Melanoma maligno anaplásico em um eqüino" Ciência Rural, Santa Maria, 2008, pp. 2072-2075, vol. 38, No. 7.
Robinson, Mark D. et al., "edgeR: a Bioconductor package for differential expression analysis of digital gene expression data" Bioinformatics, 2010, pp. 139-140, vol. 26, No. 1.
Russo, Pedro S. T. et al., "CEMiTool: a Bioconductor package for performing comprehensive modular co-expression analyses" BMC Bioinformatics, 2018, pp. 1-13, vol. 19, No. 56.
Schmidt, Mariana Costa Braga et al., "Amblyomin-X, a recombinant Kunitz-type inhibitor, regulates cell adhesion and migration of human tumor cells" Cell Adhesion & Migration, 2020, pp. 129-138, vol. 14, No. 1.
Sergushichev, Alexey A. "An algorithm for fast preranked gene set enrichment analysis using cumulative statistic calculation" Computer Technologies Department, ITMO University, Saint Petersburg, 197101, Russia, 2016, pp. 1-9.
Smith, S. H. et al., "A Comparative Review of Melanocytic Neoplasms" Vet. Pathol., 2002, pp. 651-678, vol. 39.
Subramanian, Aravind et al., "Gene set enrichment analysis: A knowledge-based approach for interpreting genome-wide expression profiles" PNAS, Oct. 2005, pp. 15545-15550, vol. 102, No. 43.
Yu, Xiaofei et al., "Activation of the MDA-5-IPS-1 Viral Sensing Pathway Induces Cancer Cell Death and Type I IFN-Dependent Antitumor Immunity" Cancer Res. 2016, pp. 2166-2176, vol. 76, No. 8.
The Gene Ontology Consortium "Gene Ontology Consortium: going forward" Nucleic Acids Research, 2015, pp. D1049-D1056, vol. 43, Database issue.
The R Core Team "R: A Language and Environment for Statistical Computing" Aug. 2021.
International Search Report for PCT/BR2019/050502 dated Feb. 21, 2020.

\* cited by examiner

Function x DEGs – First responses

Innate immune response
- RIG-I, MDA5, LGP2, DDX60, IRF7, IL8, IP10 (CXCL10) ISG15, TRIM25

Inflammatory response
- cytokines: IL1B, IL6, CCL2, IP10, IL18RB, IL6ST, OSMR, GP130

Transport vesicle & tubulin
- Tubulin beta, PTP-1B, Importin (karyopherin), Zwilch Dyneins – no DEGs
Kinesins – no DEGs
HTT - almost a DEG RAB35 - Anti-apoptosis - promotes exosome release - Regulation of exosome secretion by Rab35 and its GTPase-activating proteins
RAB31 - Breast Cancer - poor survival - early endosome are controlled by RAB22 and RAB31

RAB8B - Golgi vesicle - migration/invasion - Oncogenic RAB8 transports exocytic vesicles carrying membrane type 1-matrix metalloproteinase (MT1-MMP) to the plasma membrane for matrix degradation of migrating cancer cells cultured in collagen gel.

Proteasome inhibition
- Postulated, data from previous studies

Figure 1

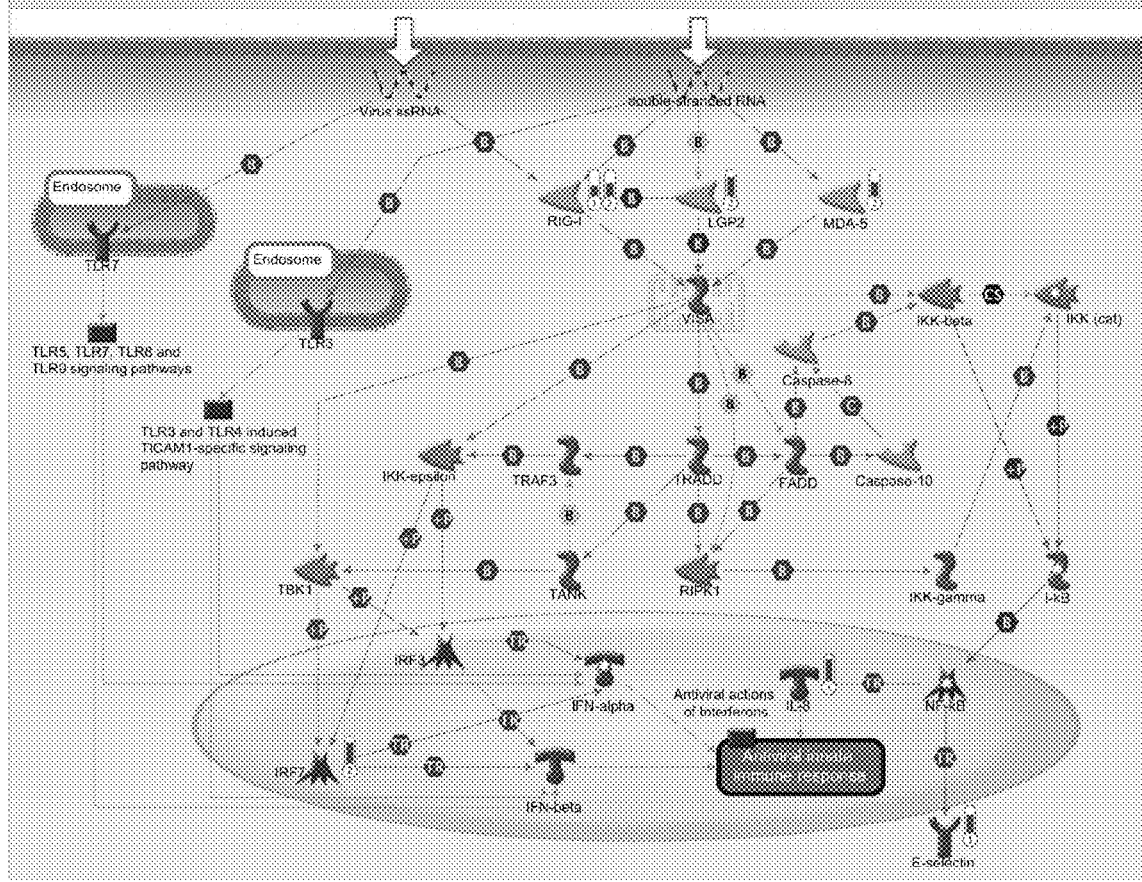

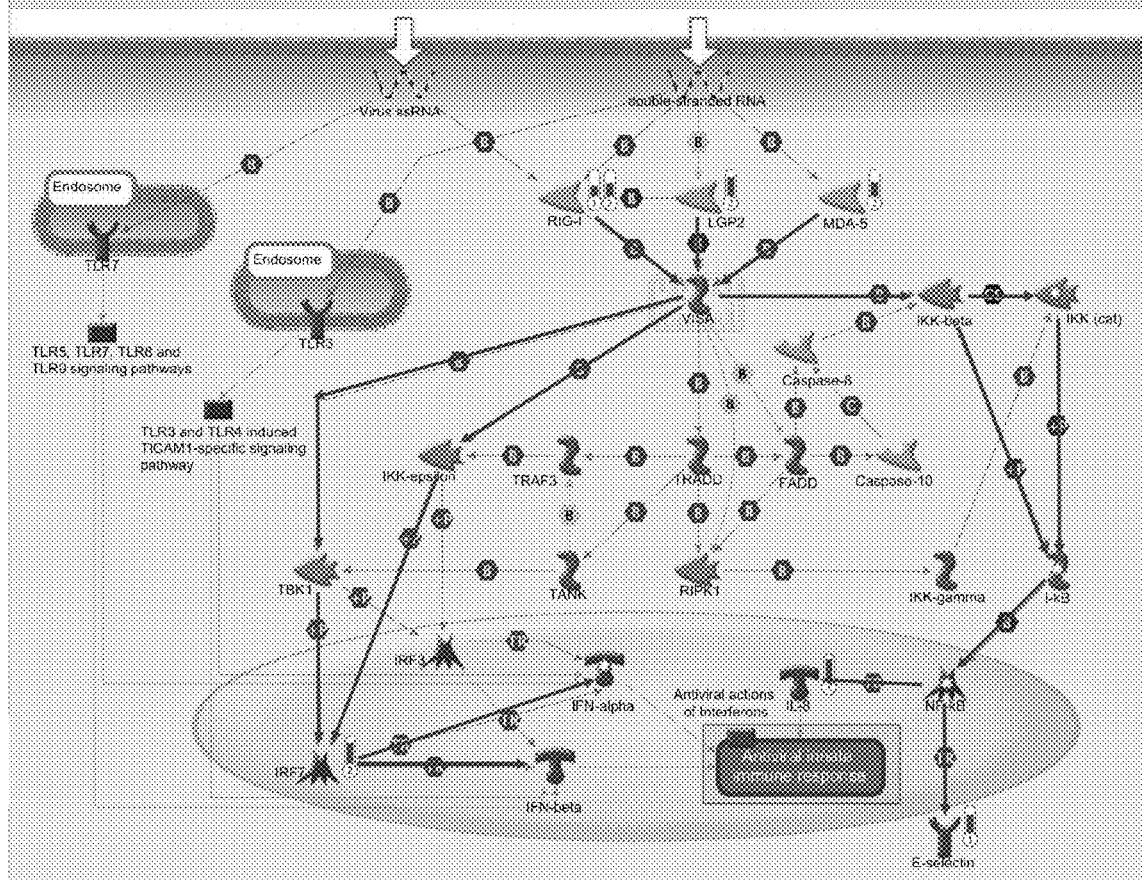

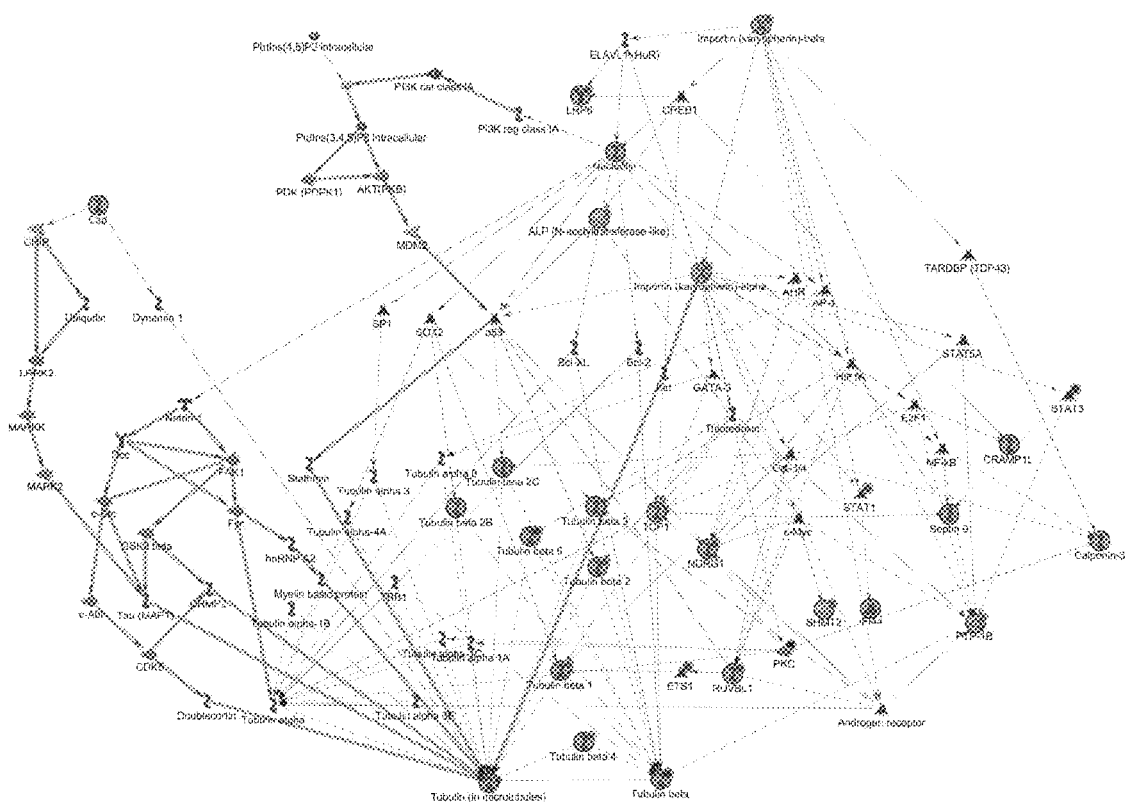

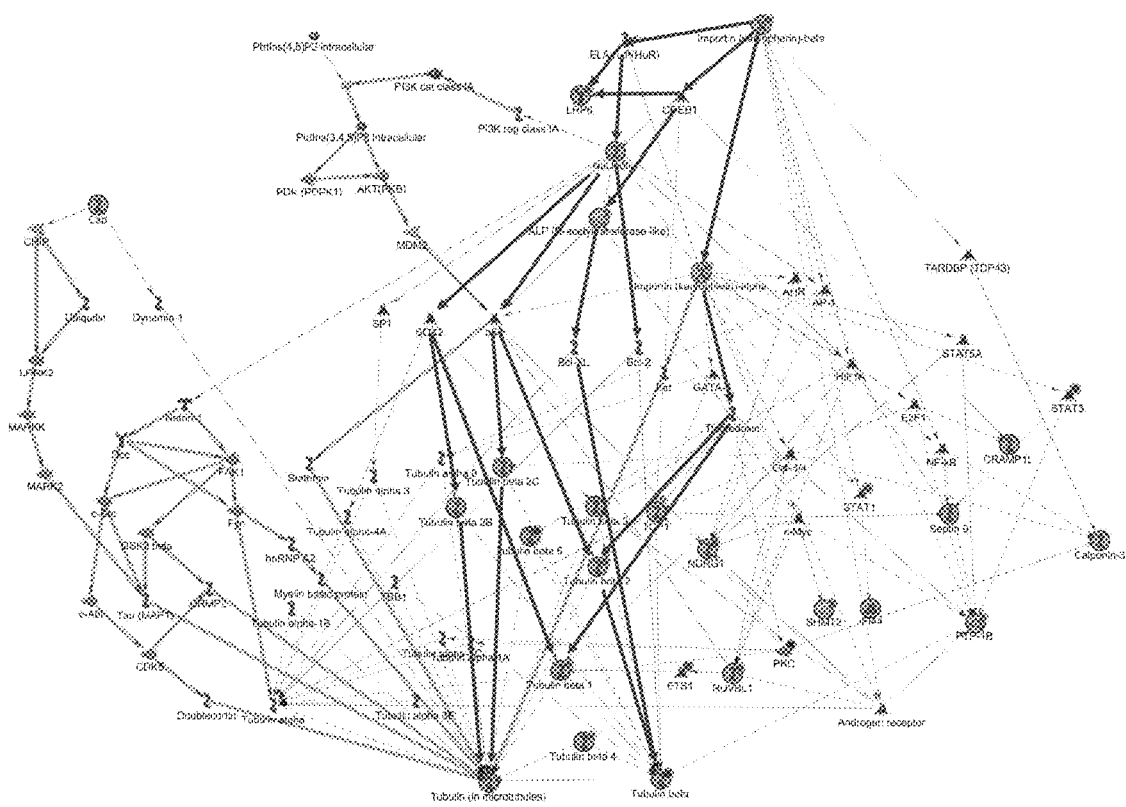

Function x DEGs – Second responses

Cellular immune response: macrophage
- CD91, P2RX7, TLR2(up,up), TLR4
- NFKB, STAT1 (up,up)
- IL6, IL8, IP10, CCL2
- IL8 --> Neutrophil migration

Accentuated innate immune response – role of PKR
- IFNA,B,G (no transcripts)
- STAT1 (up,up), IRF9 (up,up), STAT2(up,--), ISGF3
- PKR(up,up)
- WARS(up,--)
- OAS1, OAS2, OAS3
- MXA(--,up)

Endoplasmic reticulum stress Unfolded Protein Response
- Grp78, XBP1, ATF6 (Golgi - ER quality), PERK, EIF2A, EIF2A*, CALPAIN2
- To be validated: ATF4 (apoptosis CHOP), Ca+2 (ion)

Mitochondrial stress
- Cytochrome-c, SOD2, BCL2, BAX, CASP9
- To be validated: Ca2+, ψ - mitochondria membrane potential

Remodeling of the extracellular matrix
- IL1B, IL1RI, CCL2, PDGF-RA, EDNRB (endothelin receptor type B), PAI1, THBS1 (Thrombolspondin 1), MMP3 (Stromelysin-1), Cathepsin-L (CTSL ?) --> exception MMP1 (dw, --)

Figure 3

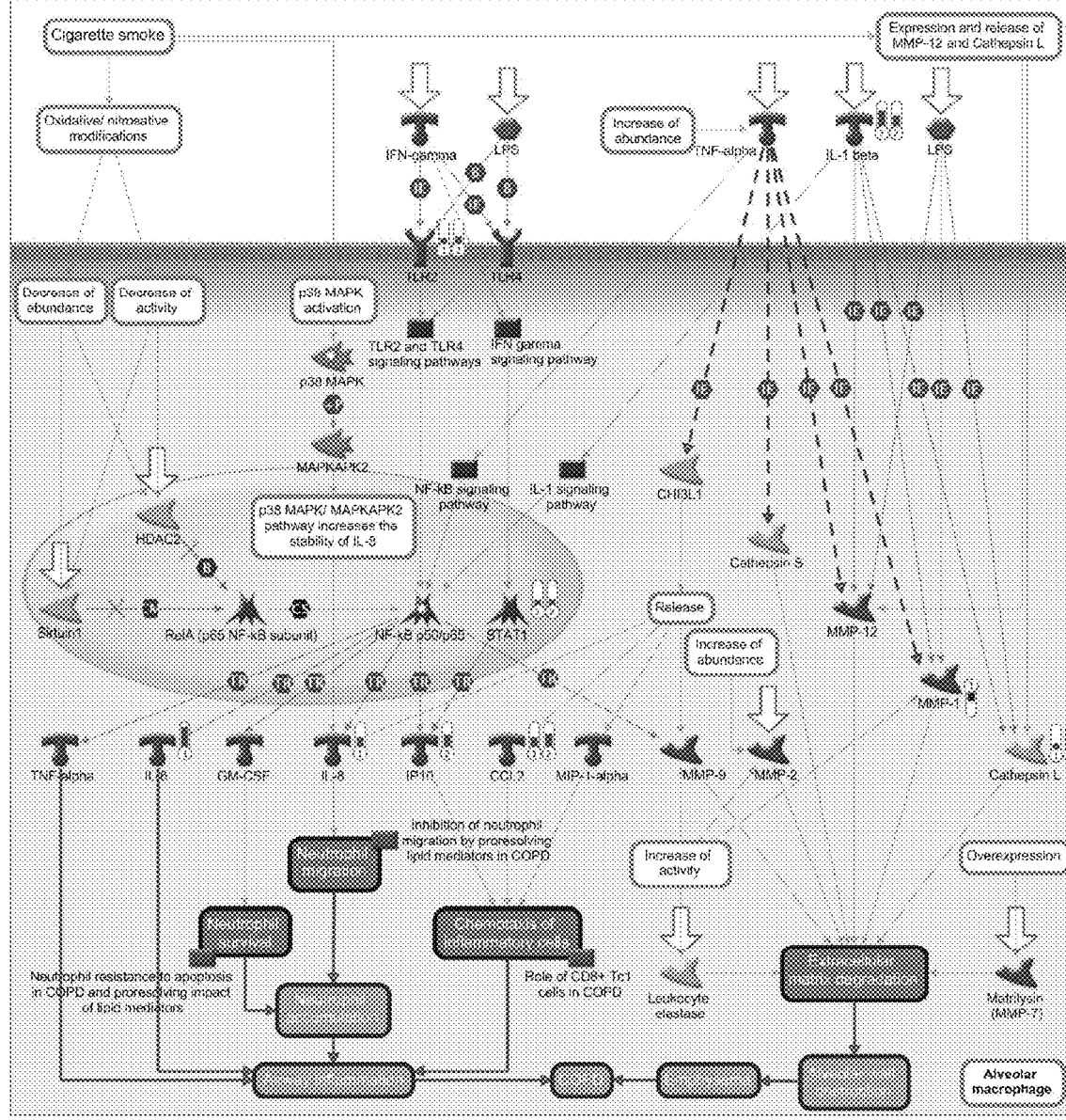
via11 - Release of pro-inflammatory mediators and elastolytic enzymes by alveolar macrophages in COPD

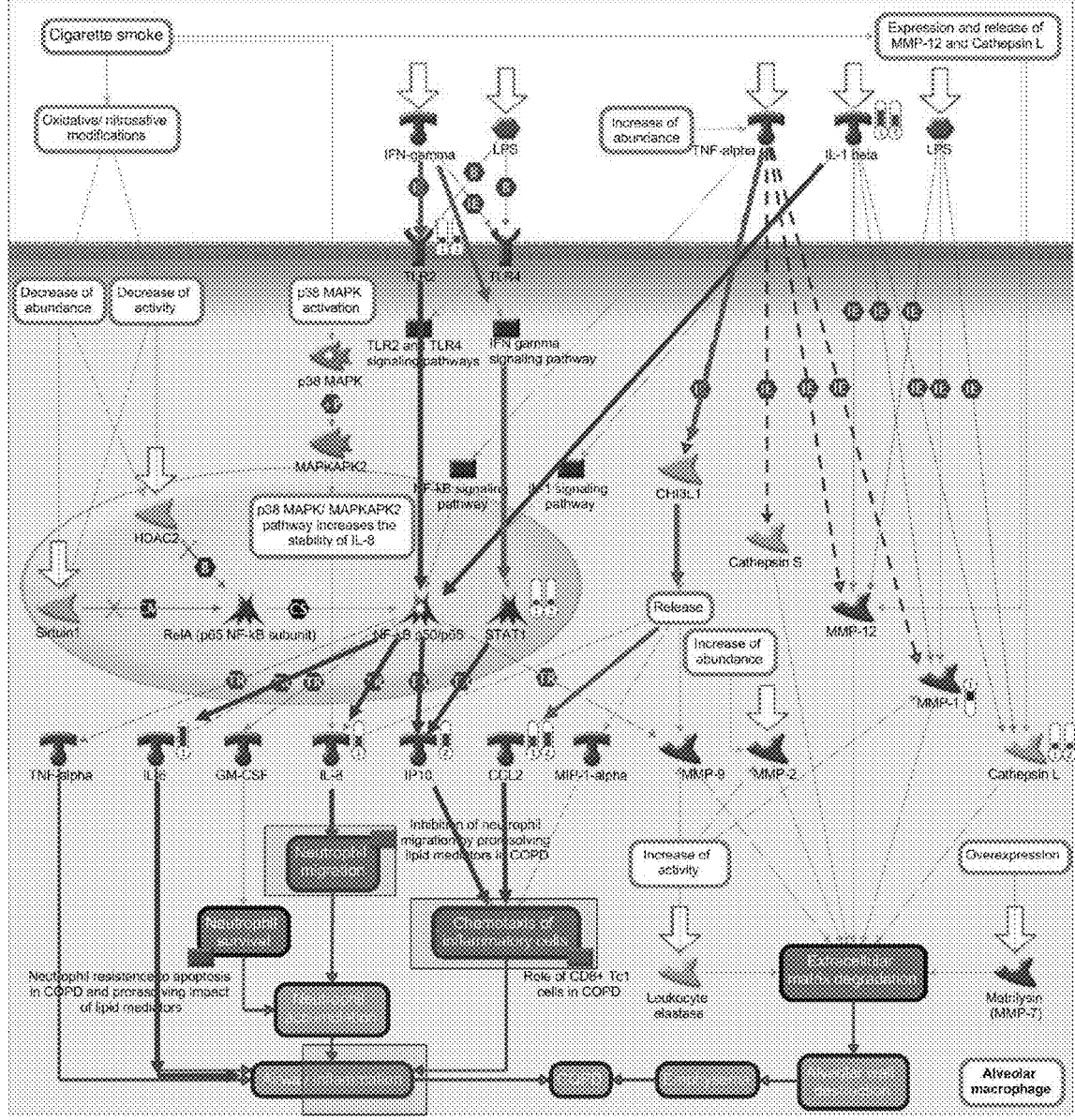
via11 - Release of pro-inflammatory mediators and elastolytic enzymes by alveolar macrophages in COPD

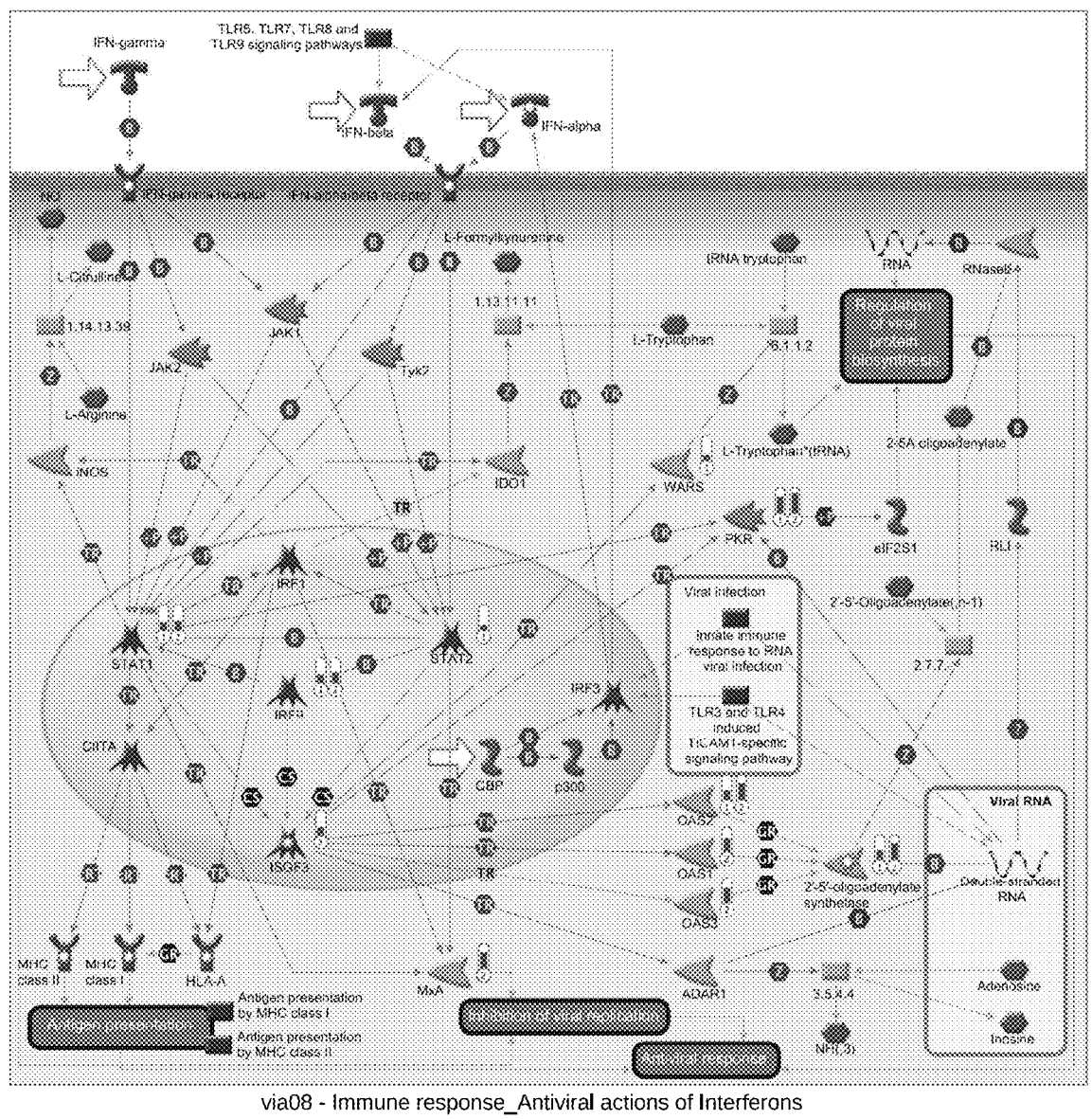

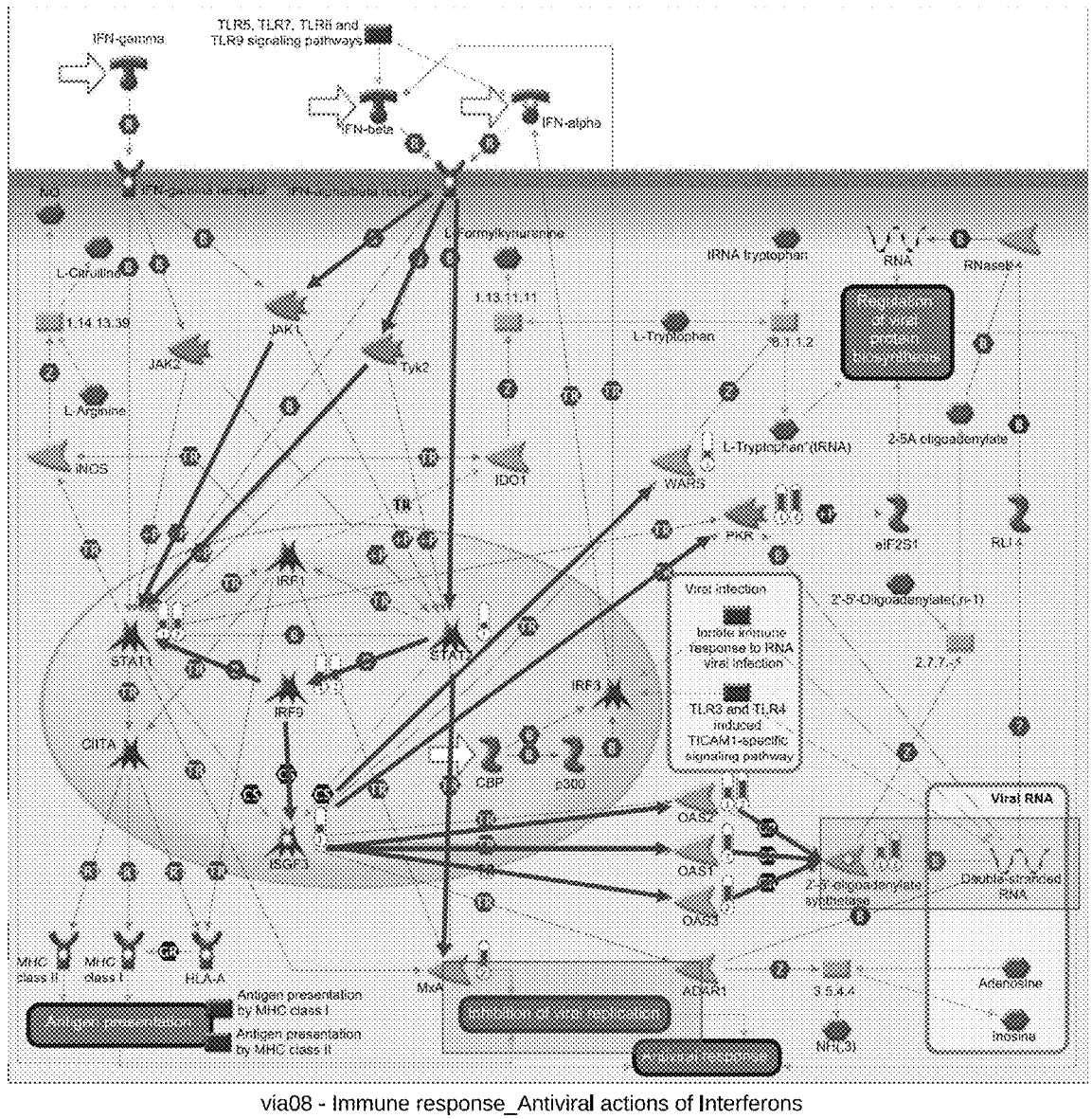
via08 - Immune response_Antiviral actions of Interferons

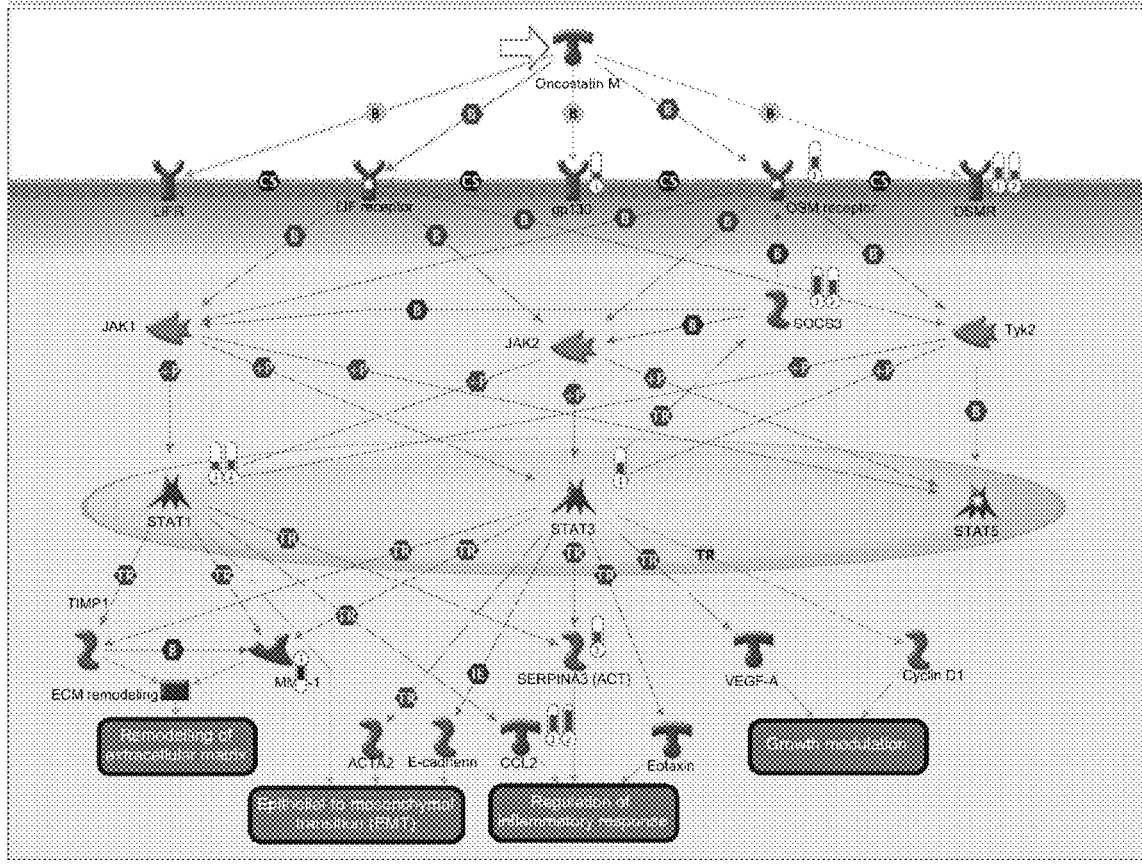
via04 - Immune response_Oncostatin M signaling via JAK-Stat

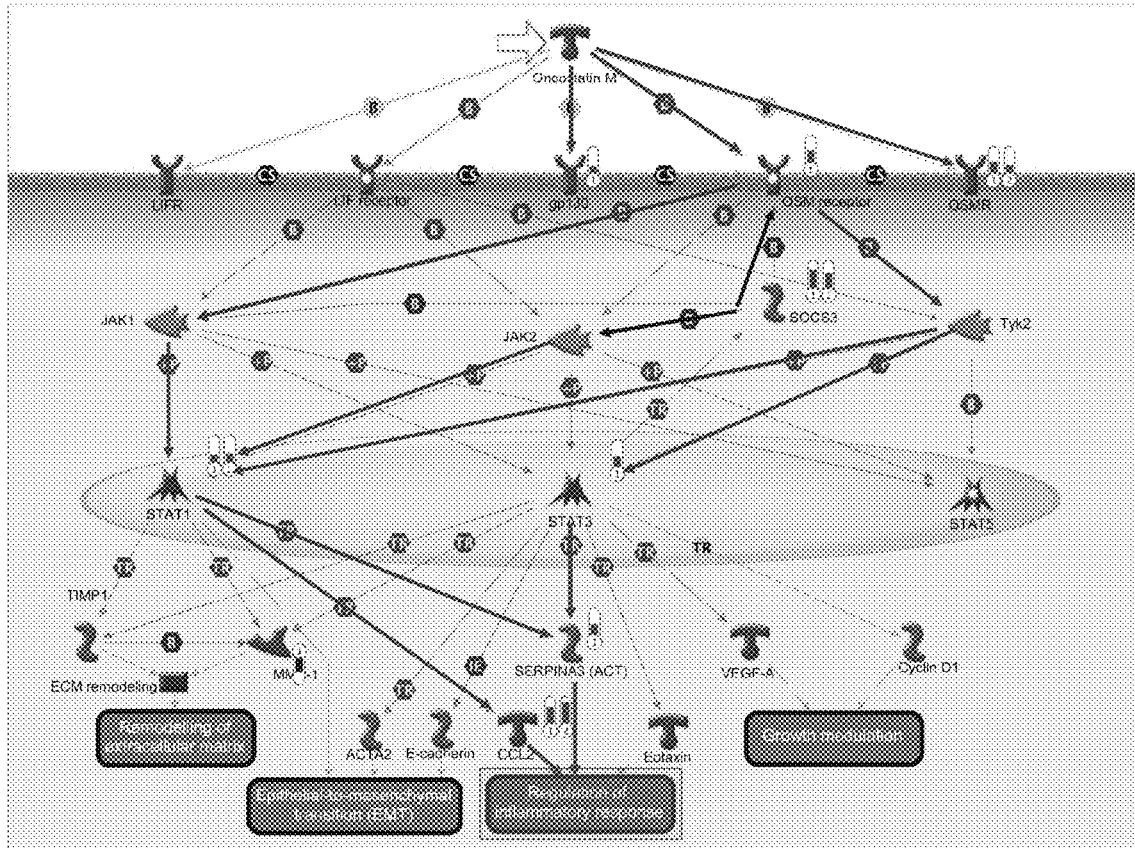

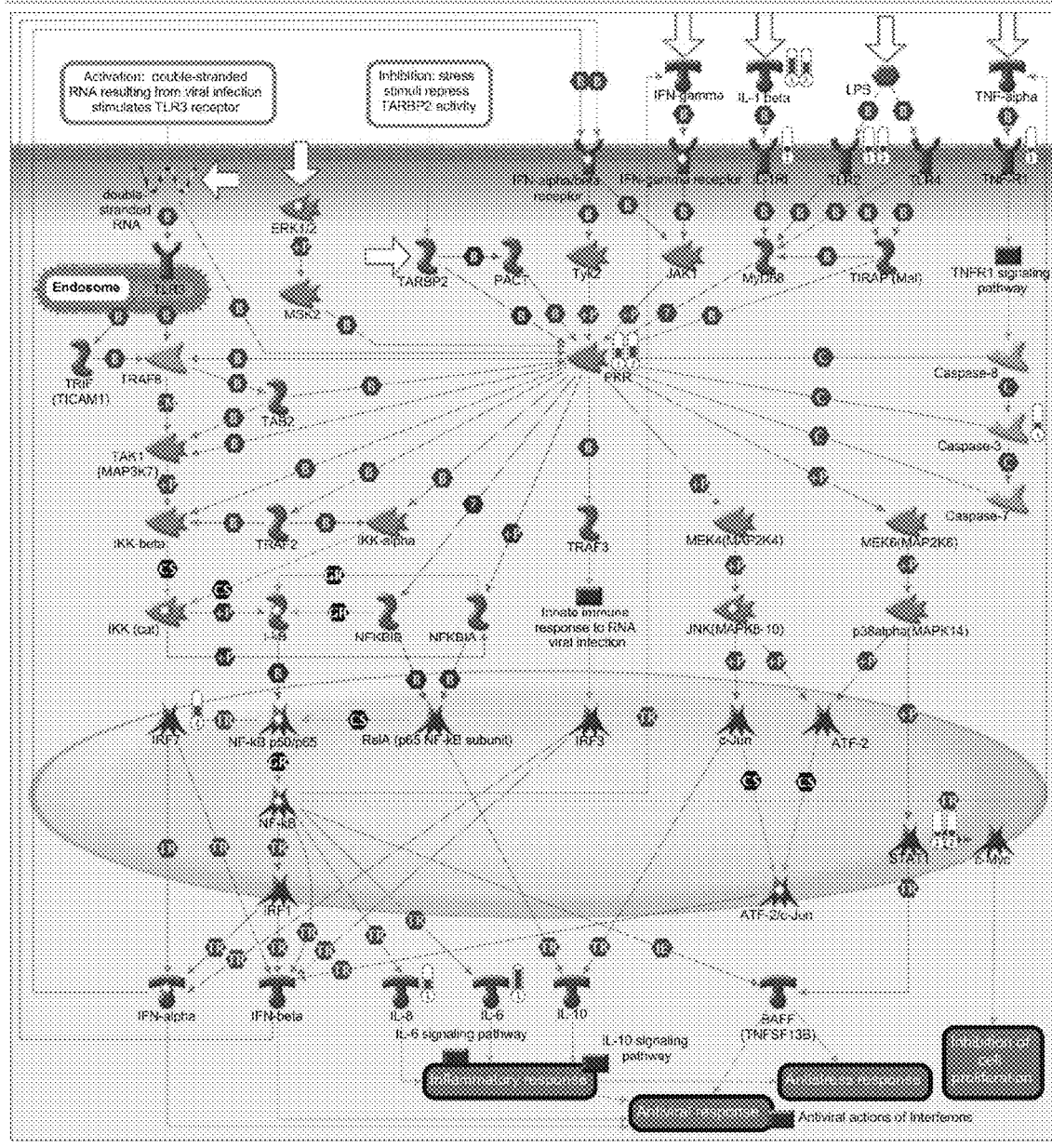
Pathway 37 - Immune response_Role of PKR in stress-induced antiviral cell response

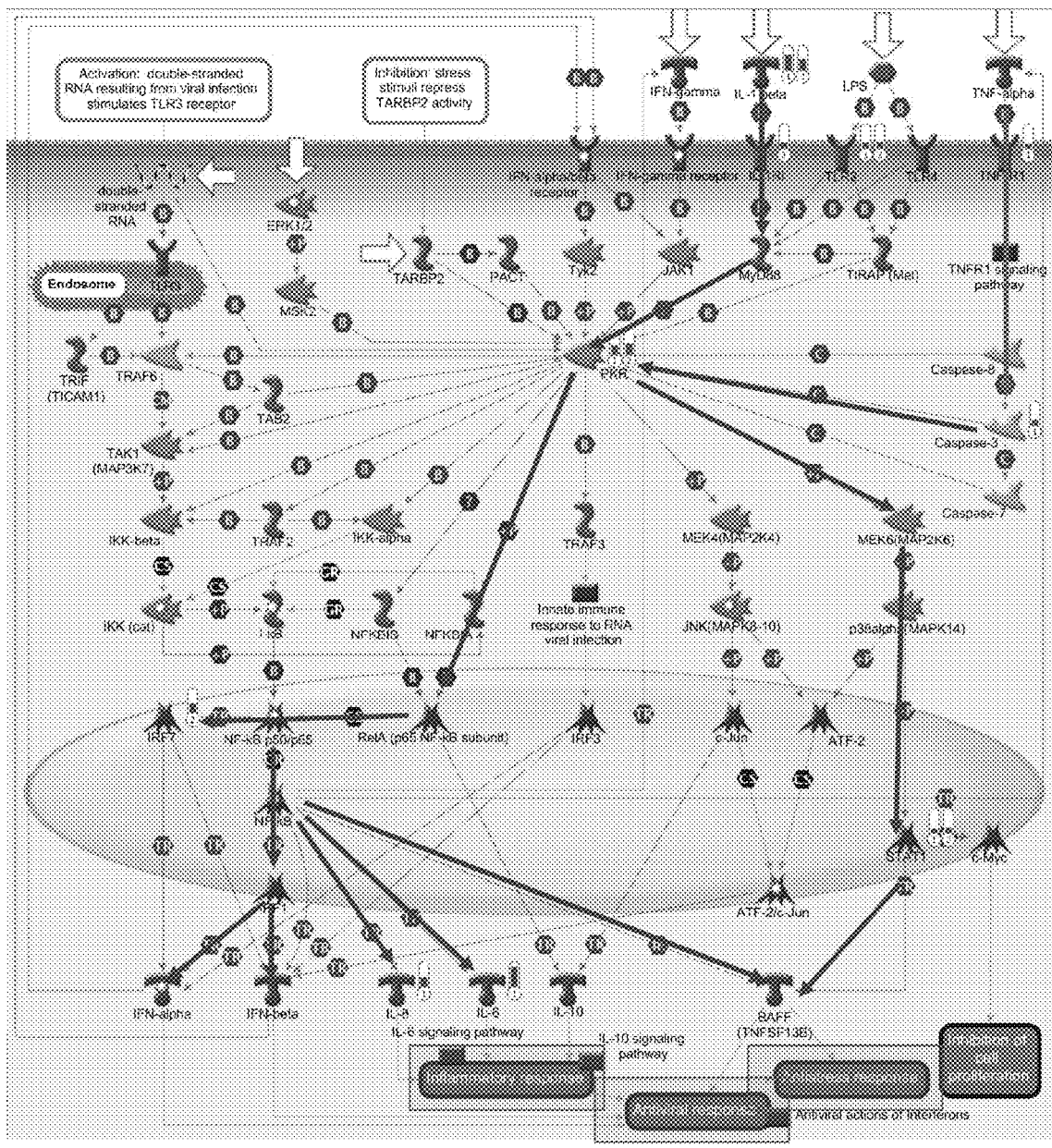
Pathway 37 - Immune response_Role of PKR in stress-induced antiviral cell response

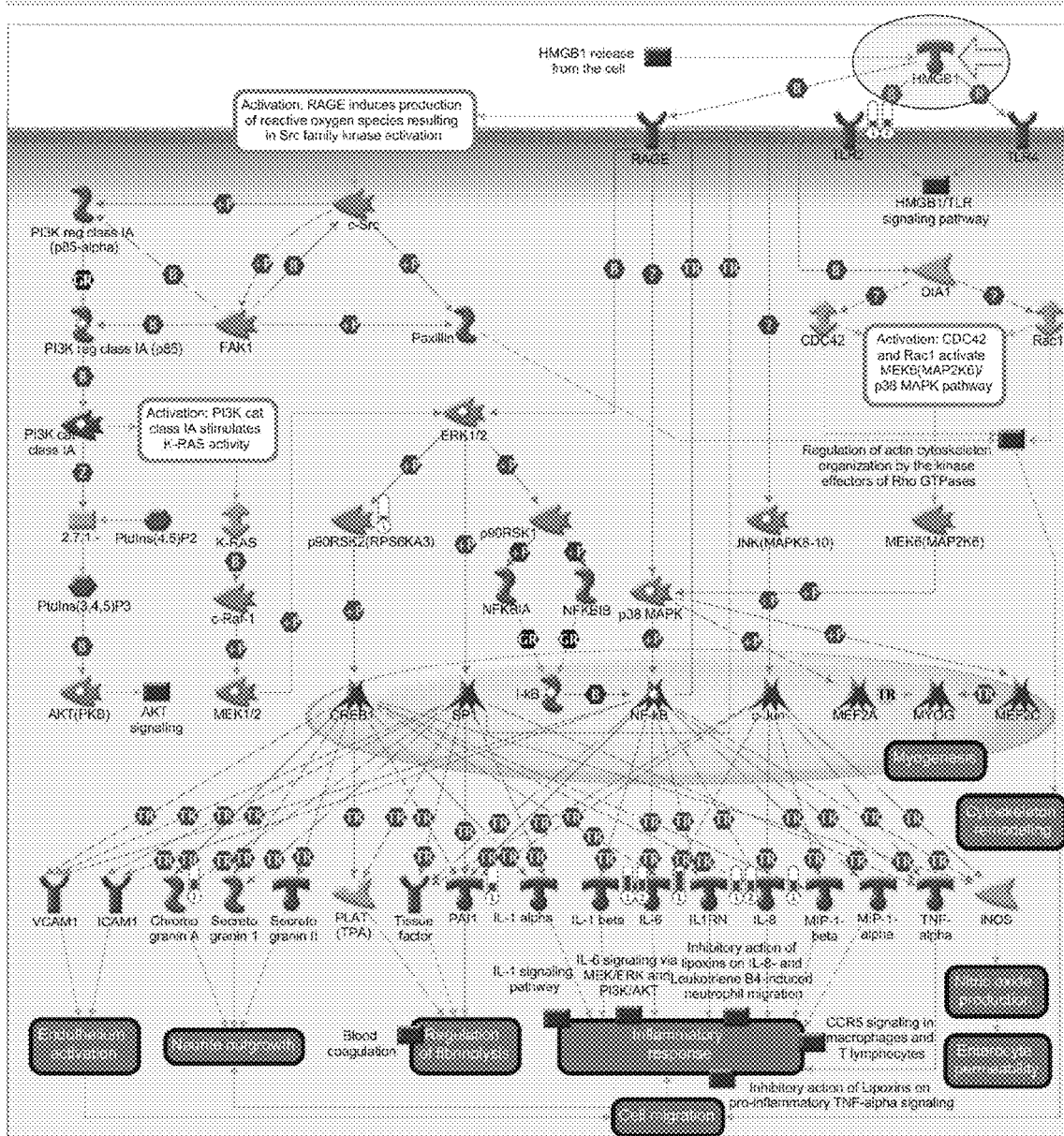
Pathway 59 - Immune response_HMGB1-RAGE signaling pathway

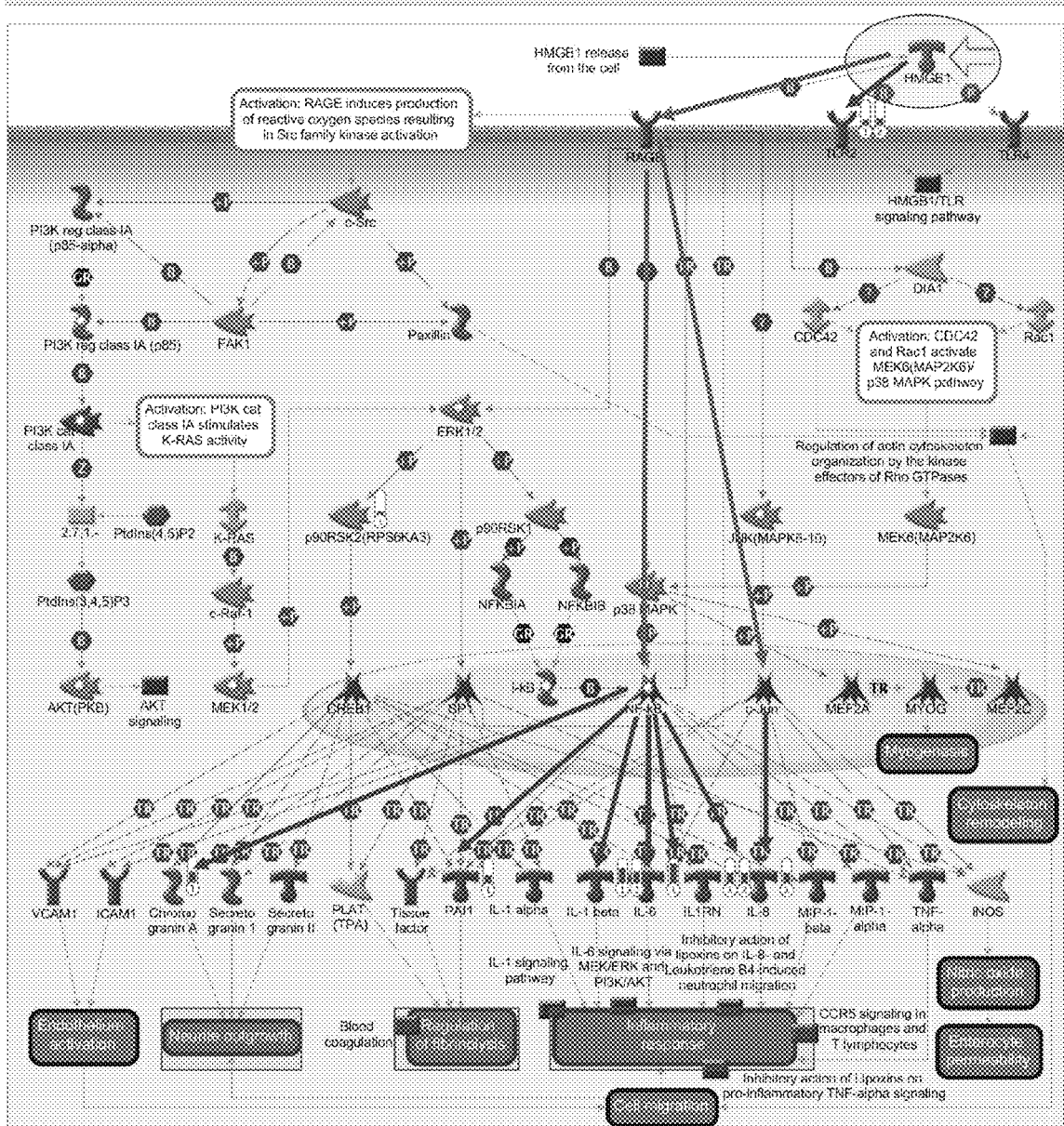
Pathway 59 - Immune response_HMGB1-RAGE signaling pathway

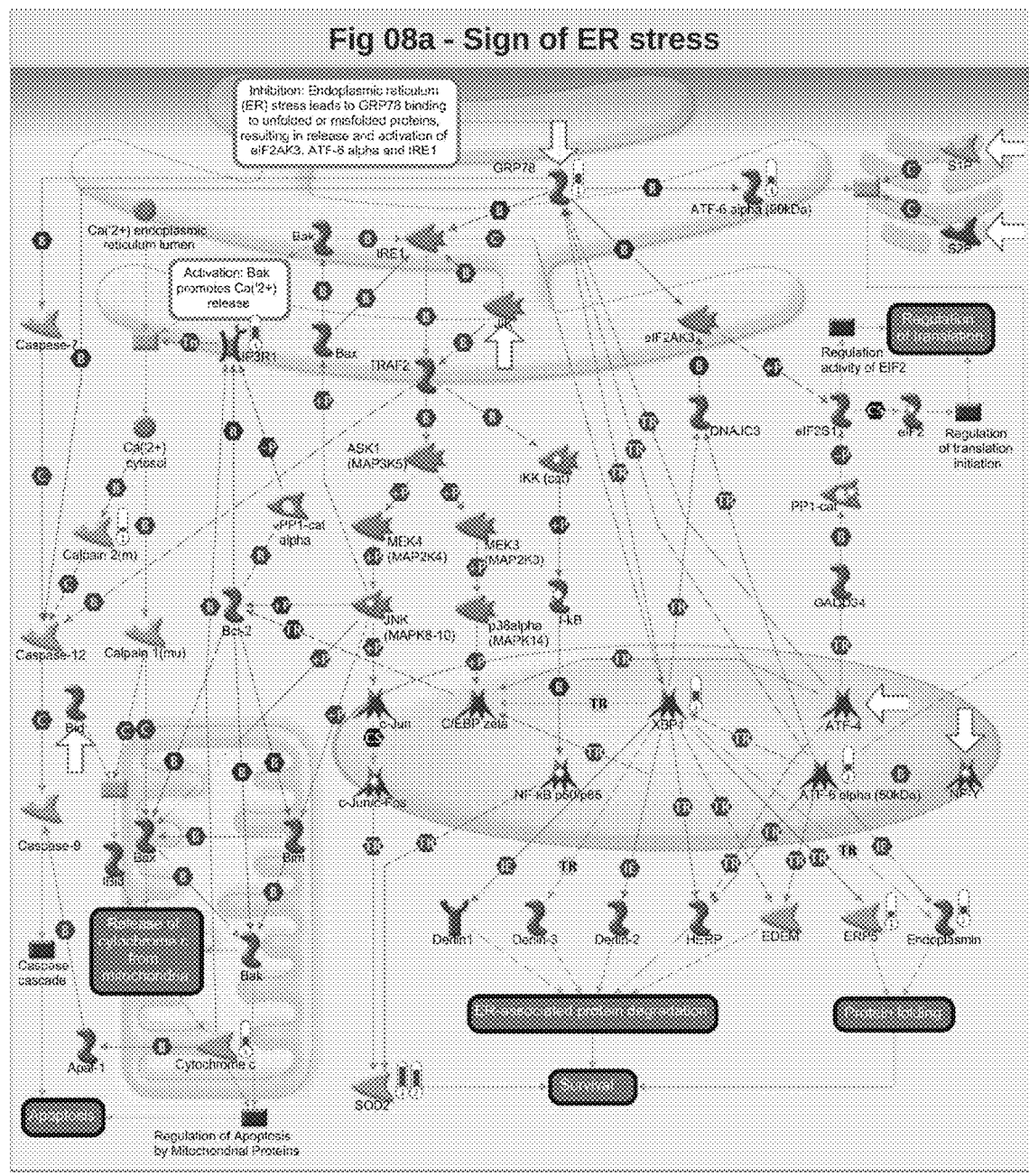
Pathway 17 - Apoptosis and survival_Endoplasmic reticulum stress response pathway

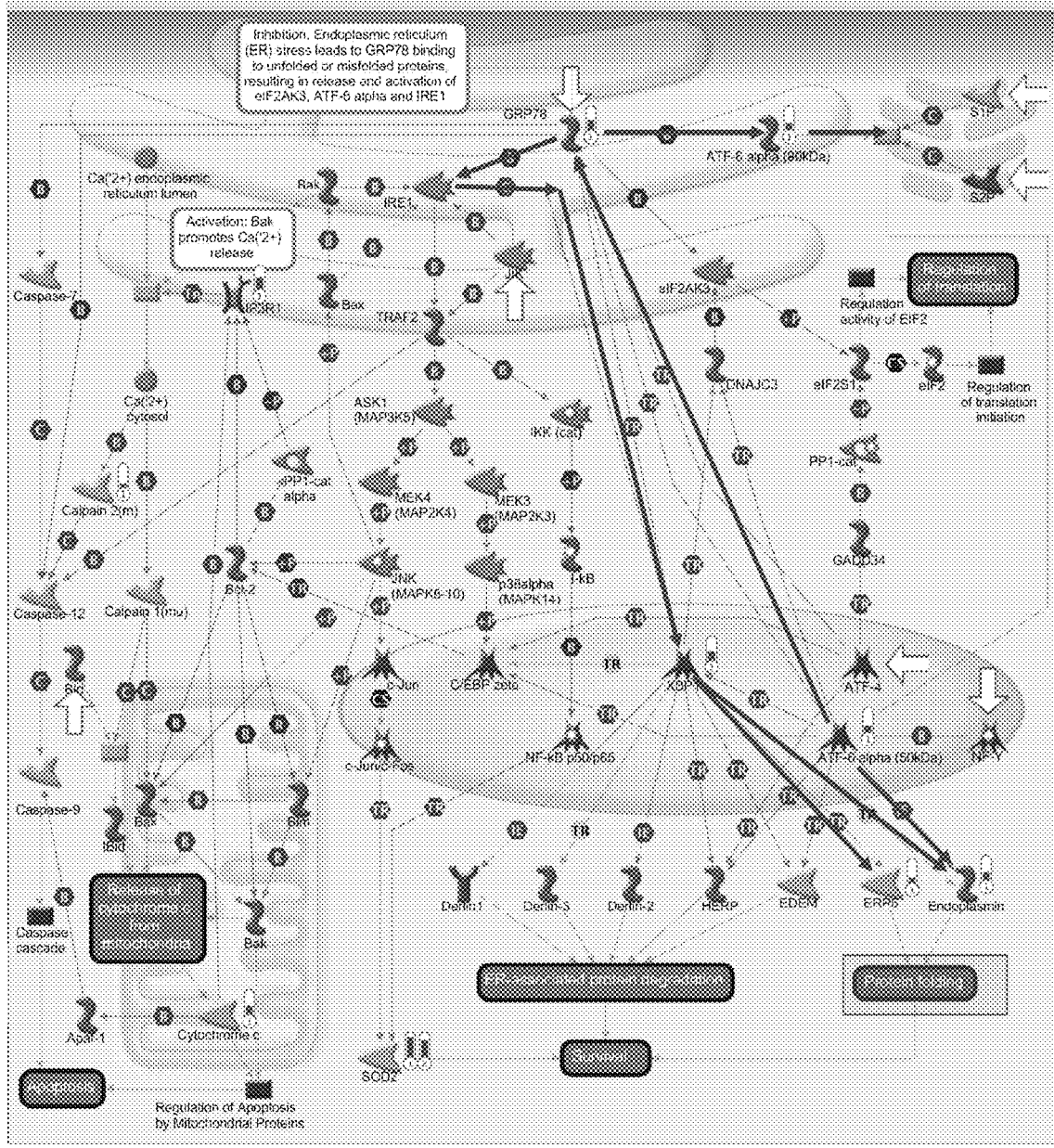

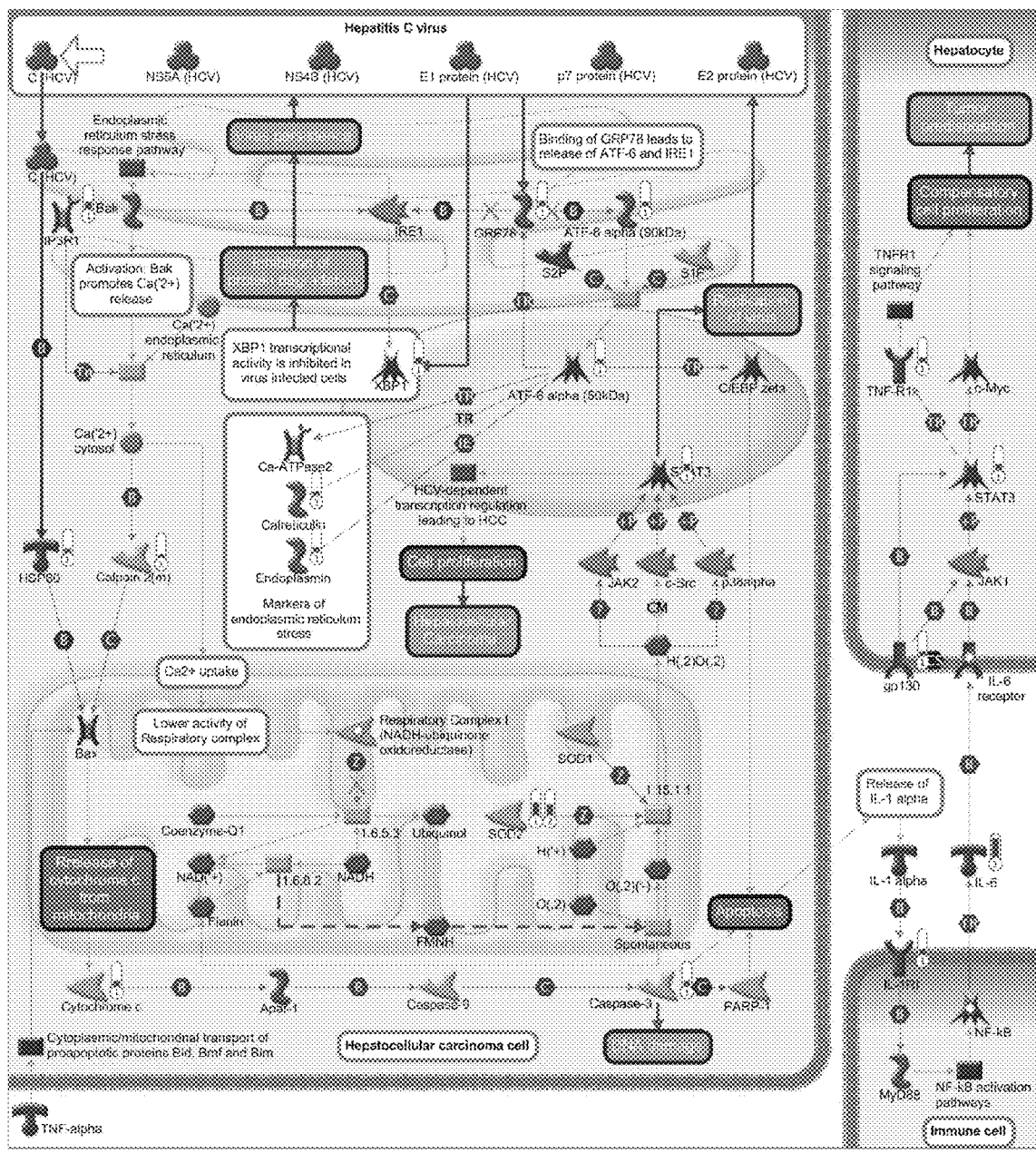
Pathway 01 - HCV-mediated liver damage and predisposition to HCC via cell stress

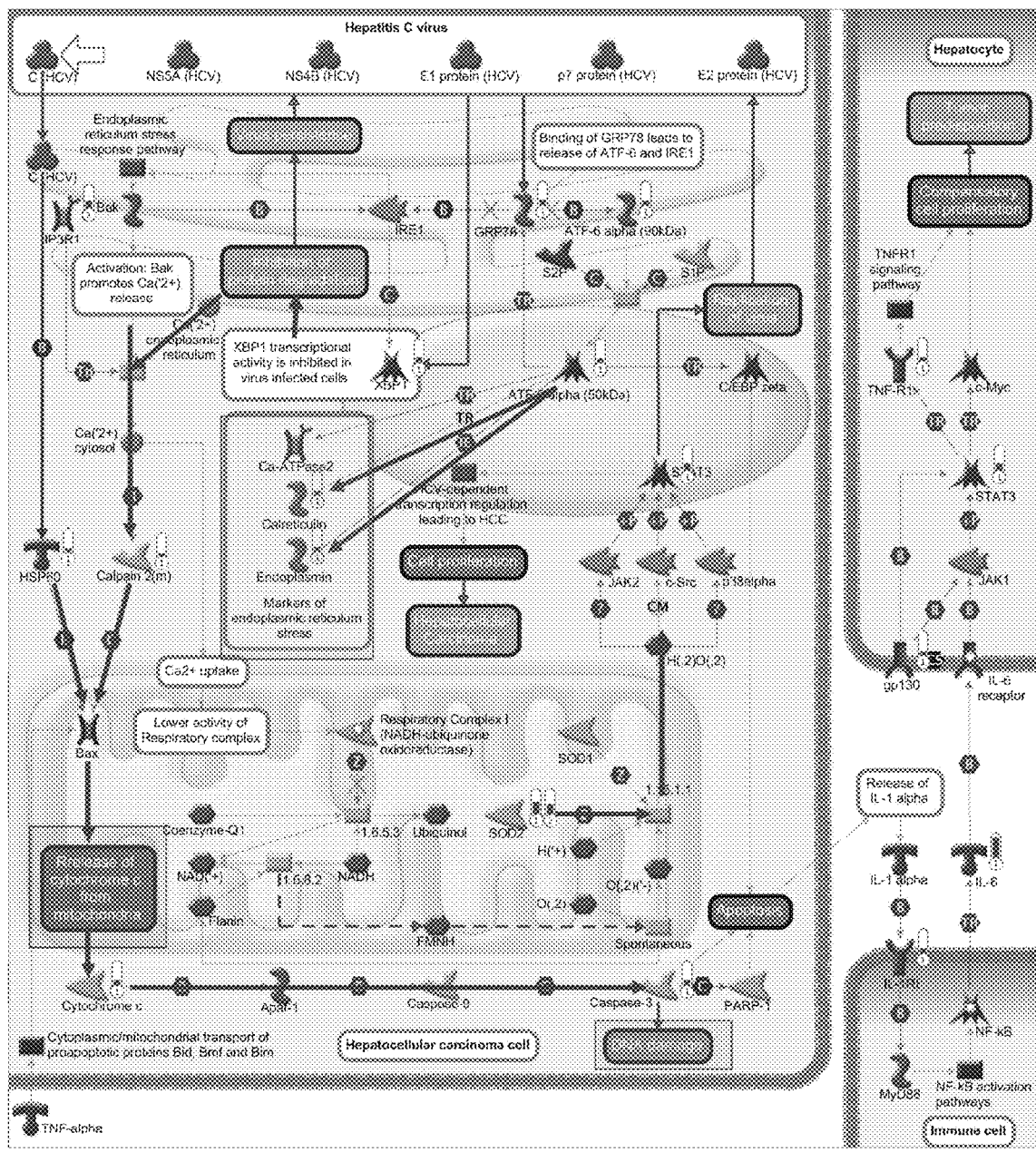

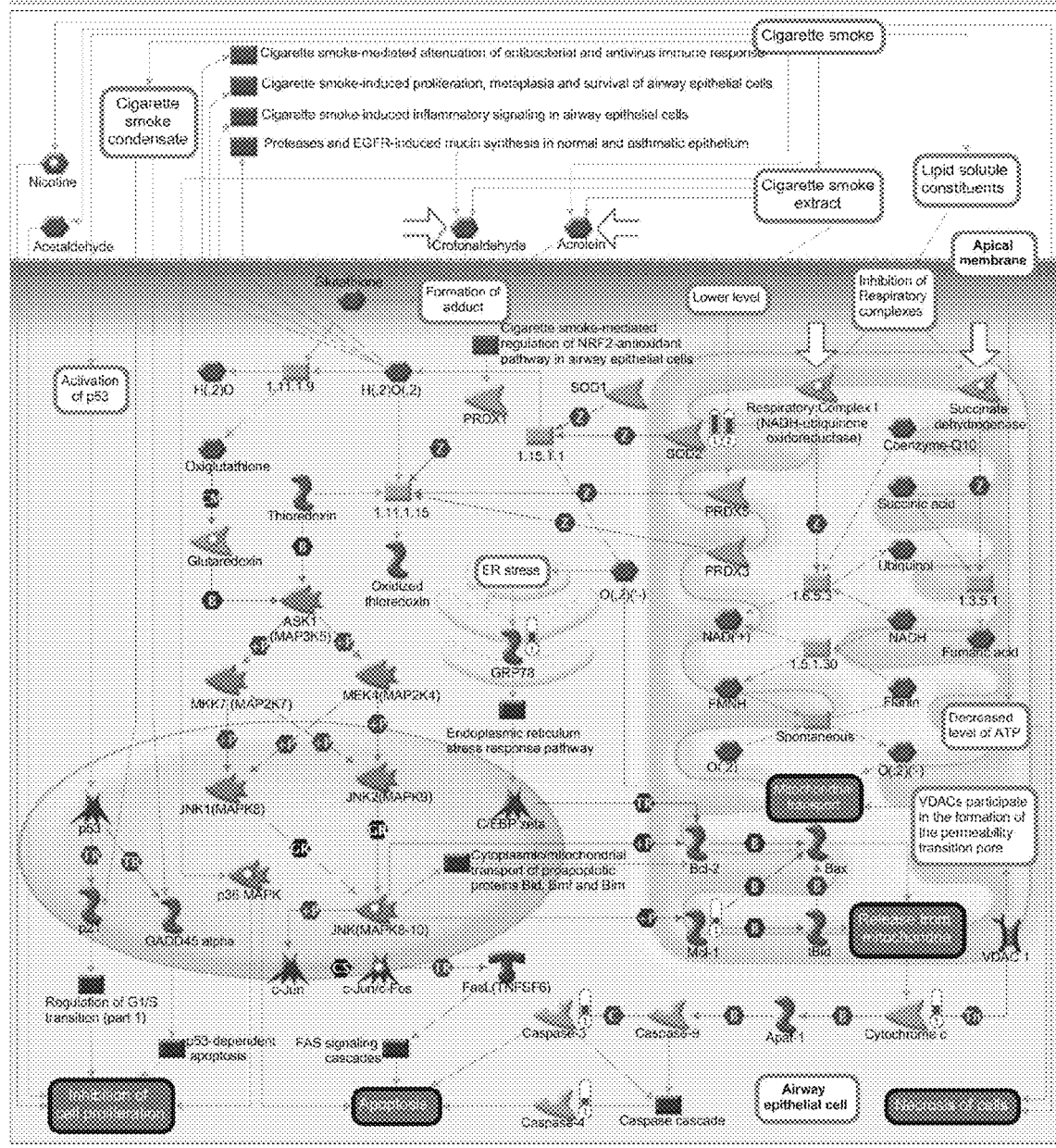
pathway237 - Oxidative stress and apoptosis in respiratory epithelial cells induced by cigarette smoke

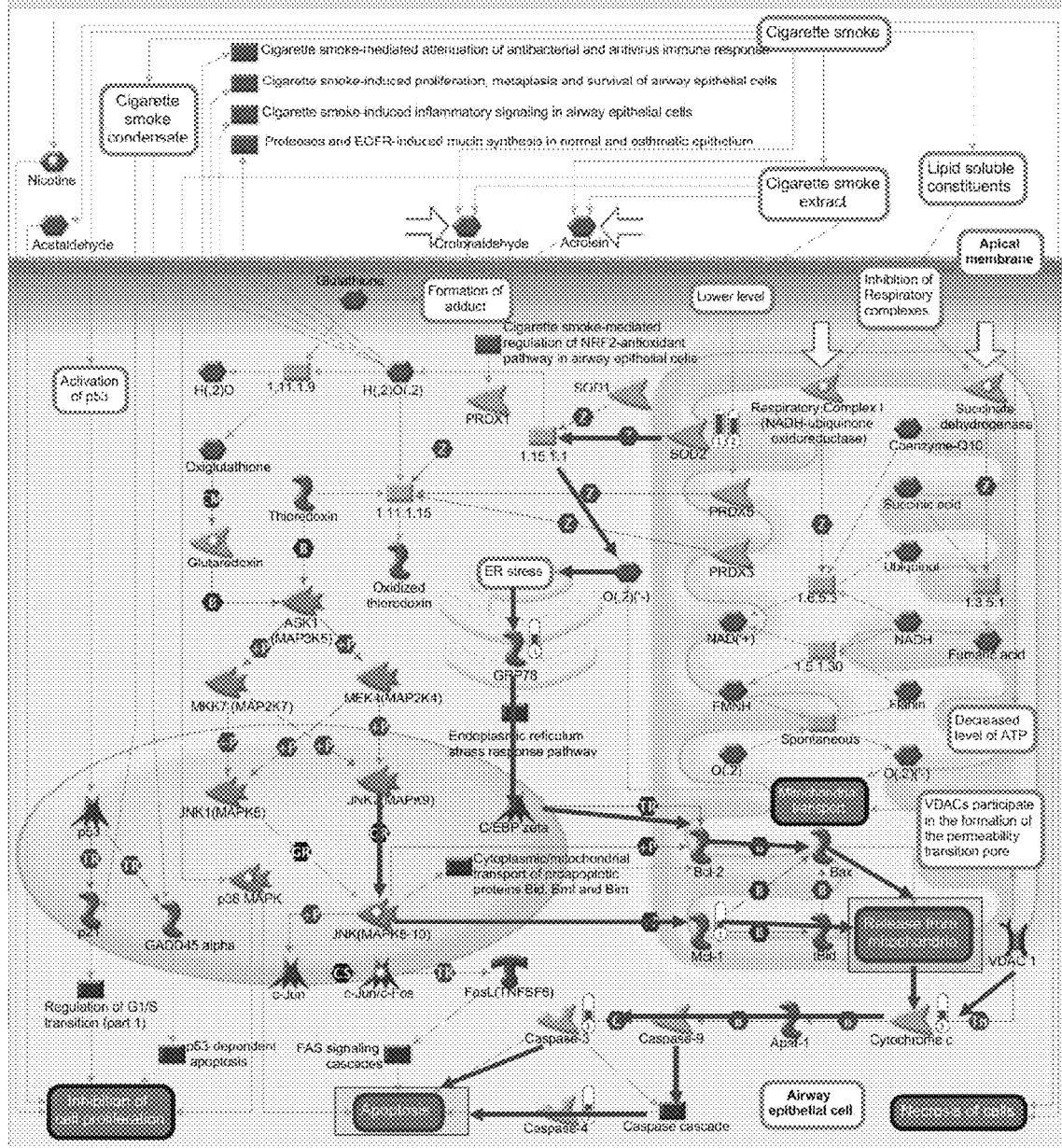

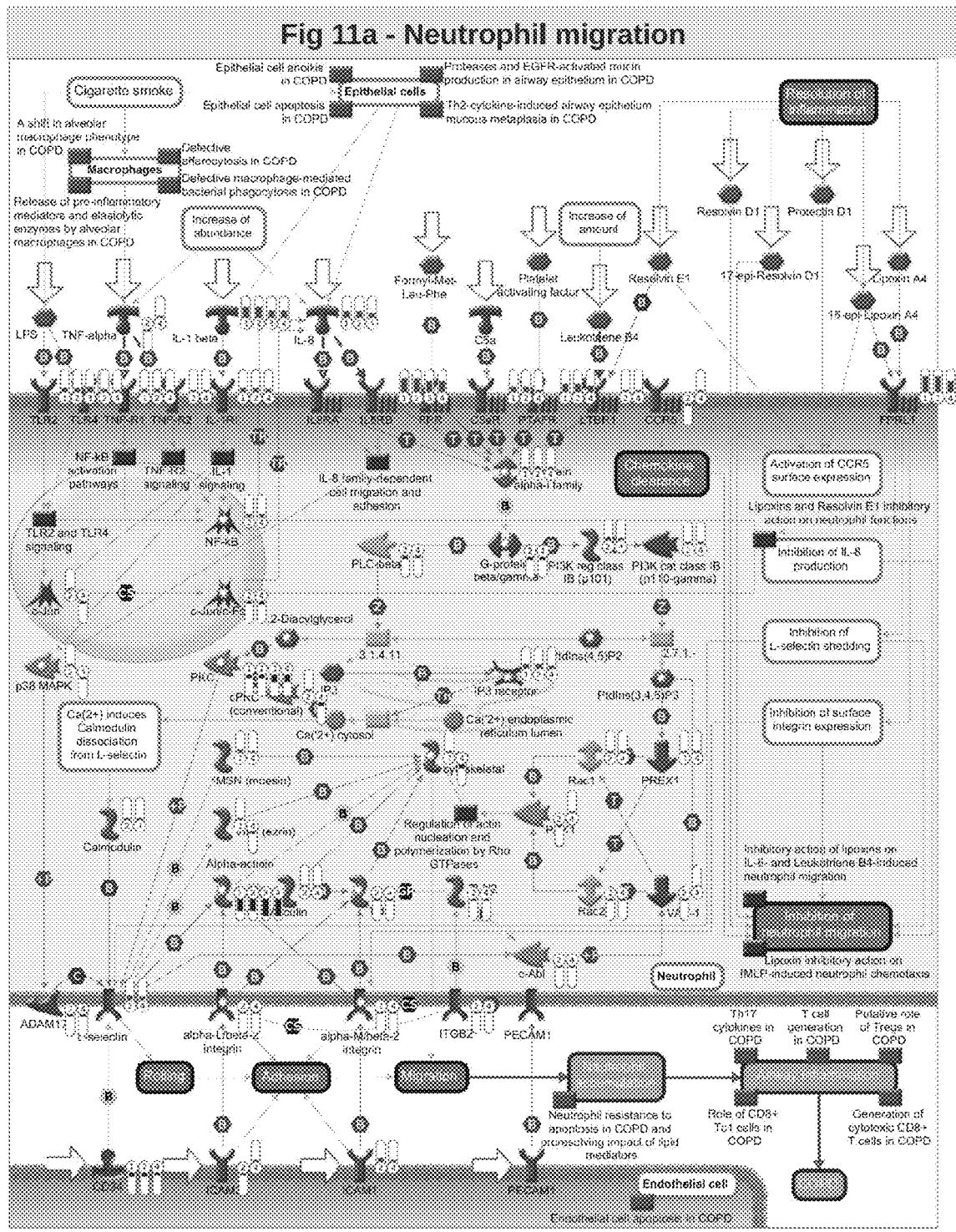
pathway12 - Inhibition of neutrophil migration by pre-resolution of lipid mediators in COPD

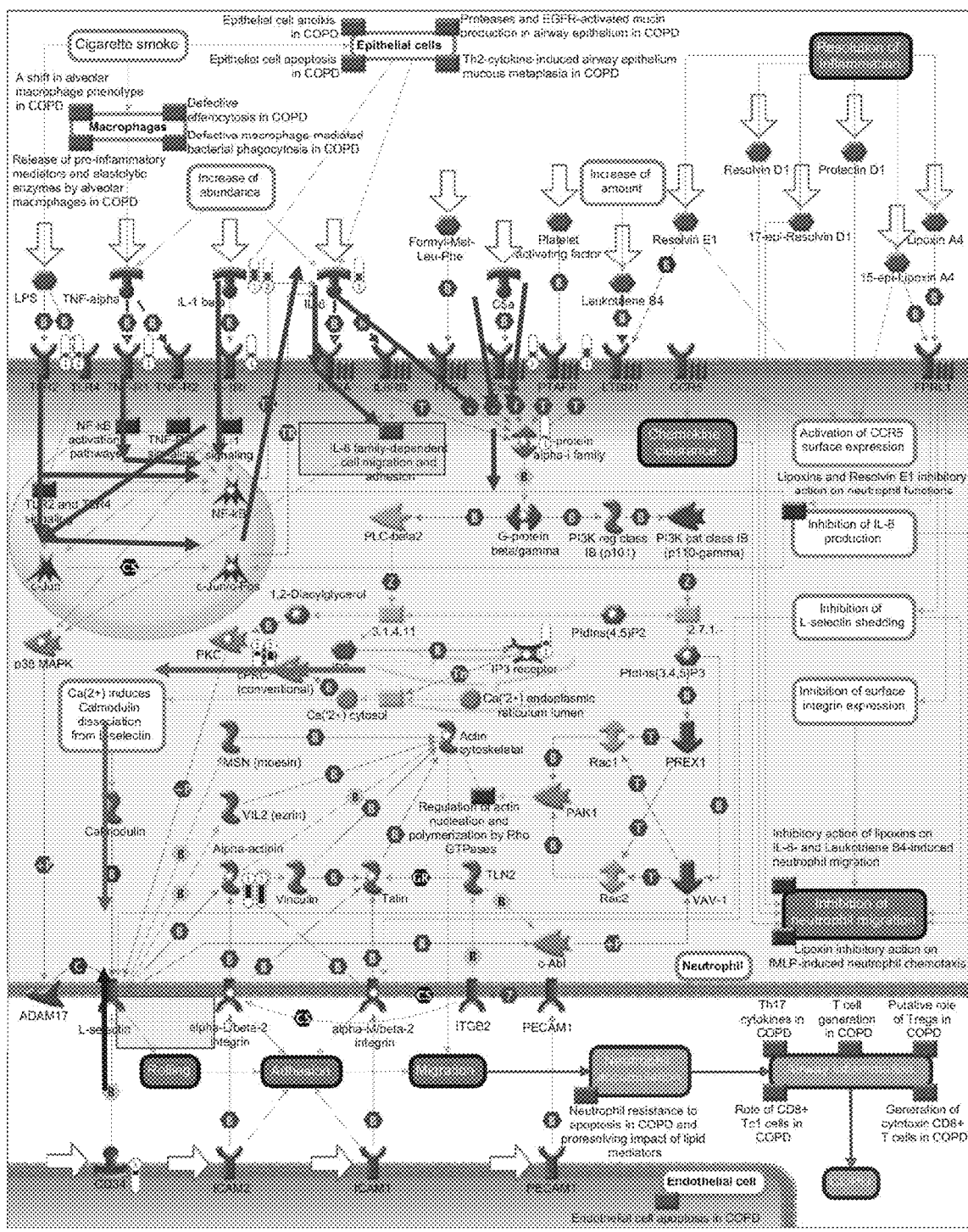

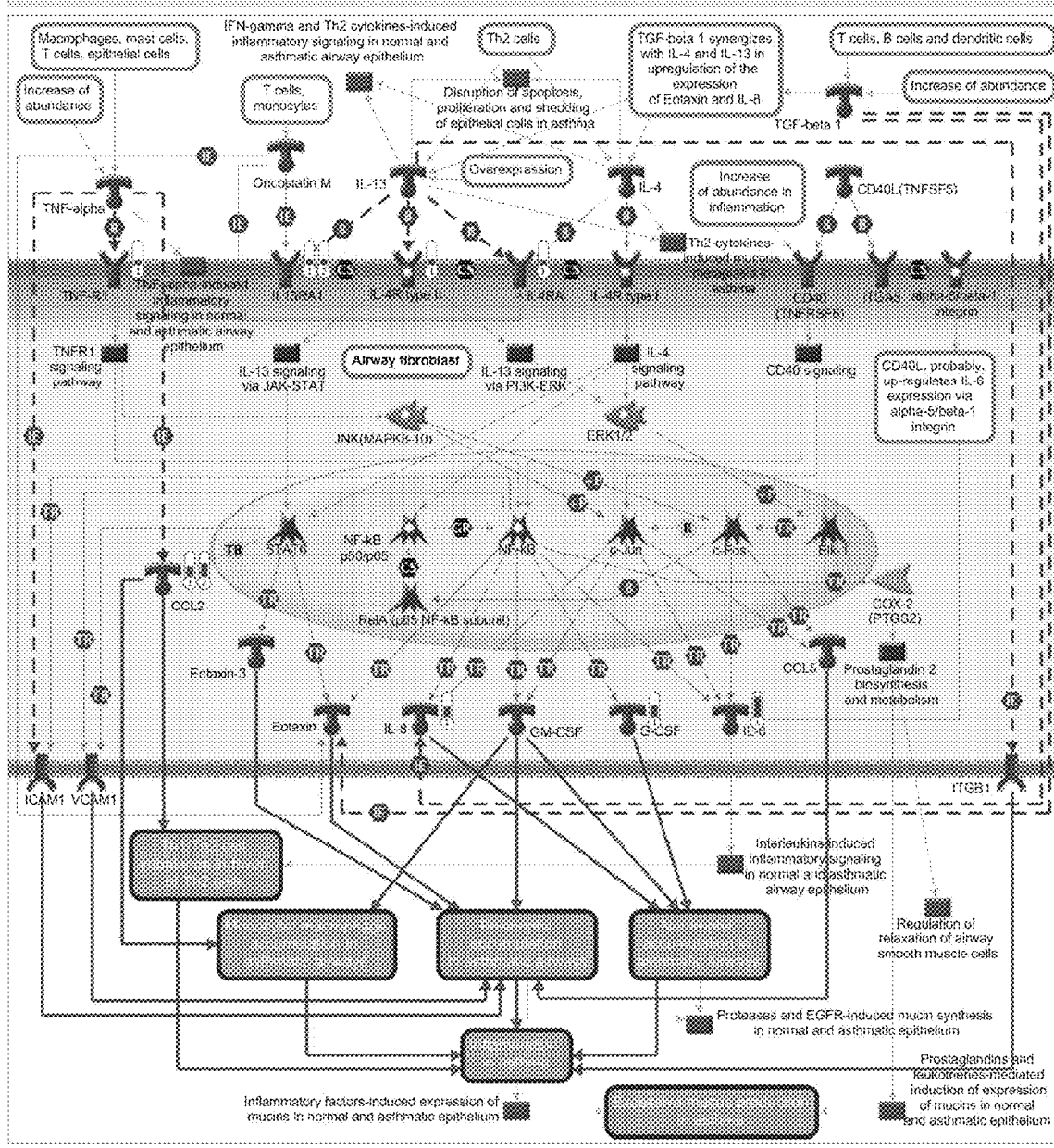
pathway19 - Th2 cytokine - and alpha-TNF induces inflammatory response in asthmatic airway fibroblasts

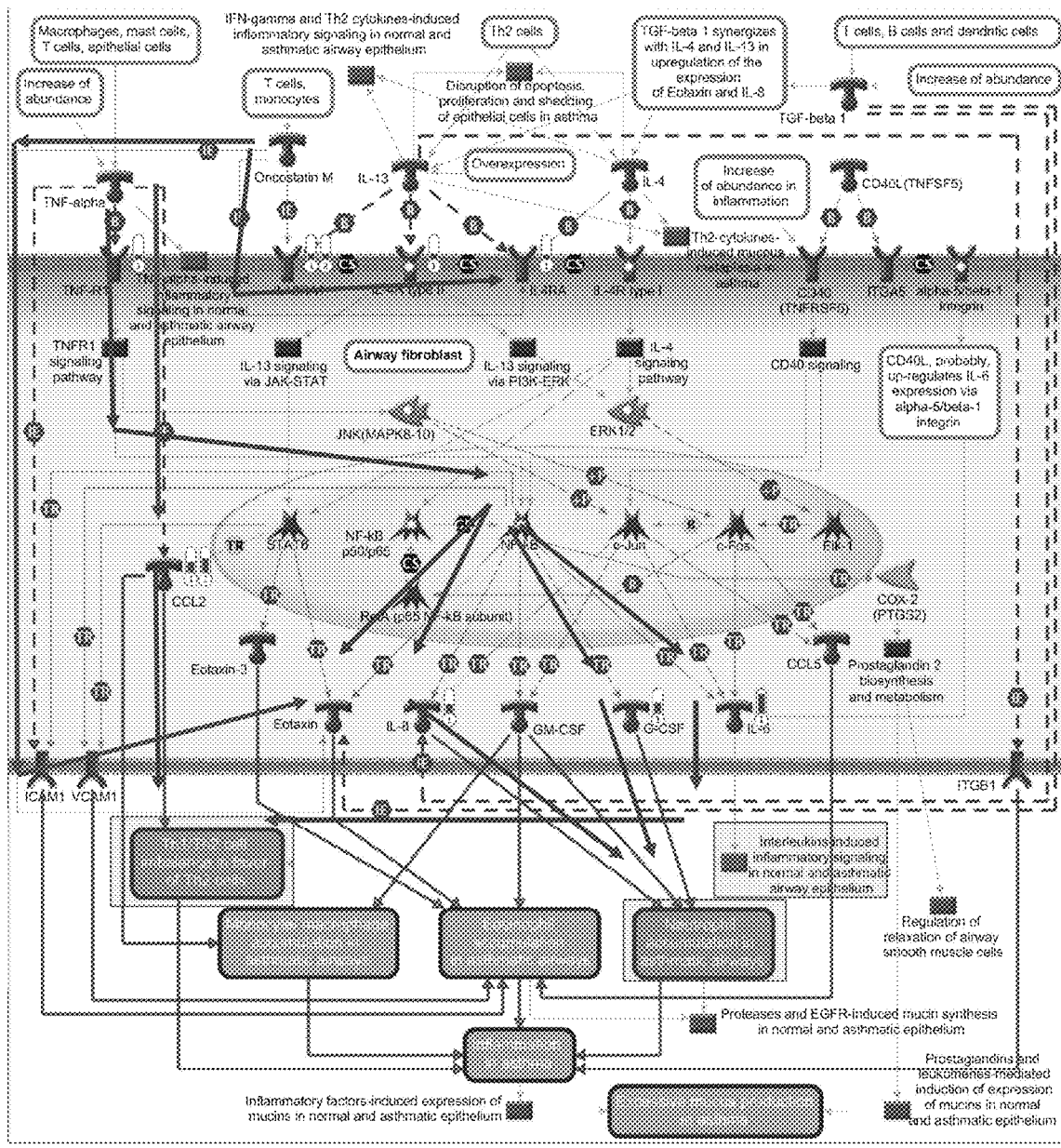

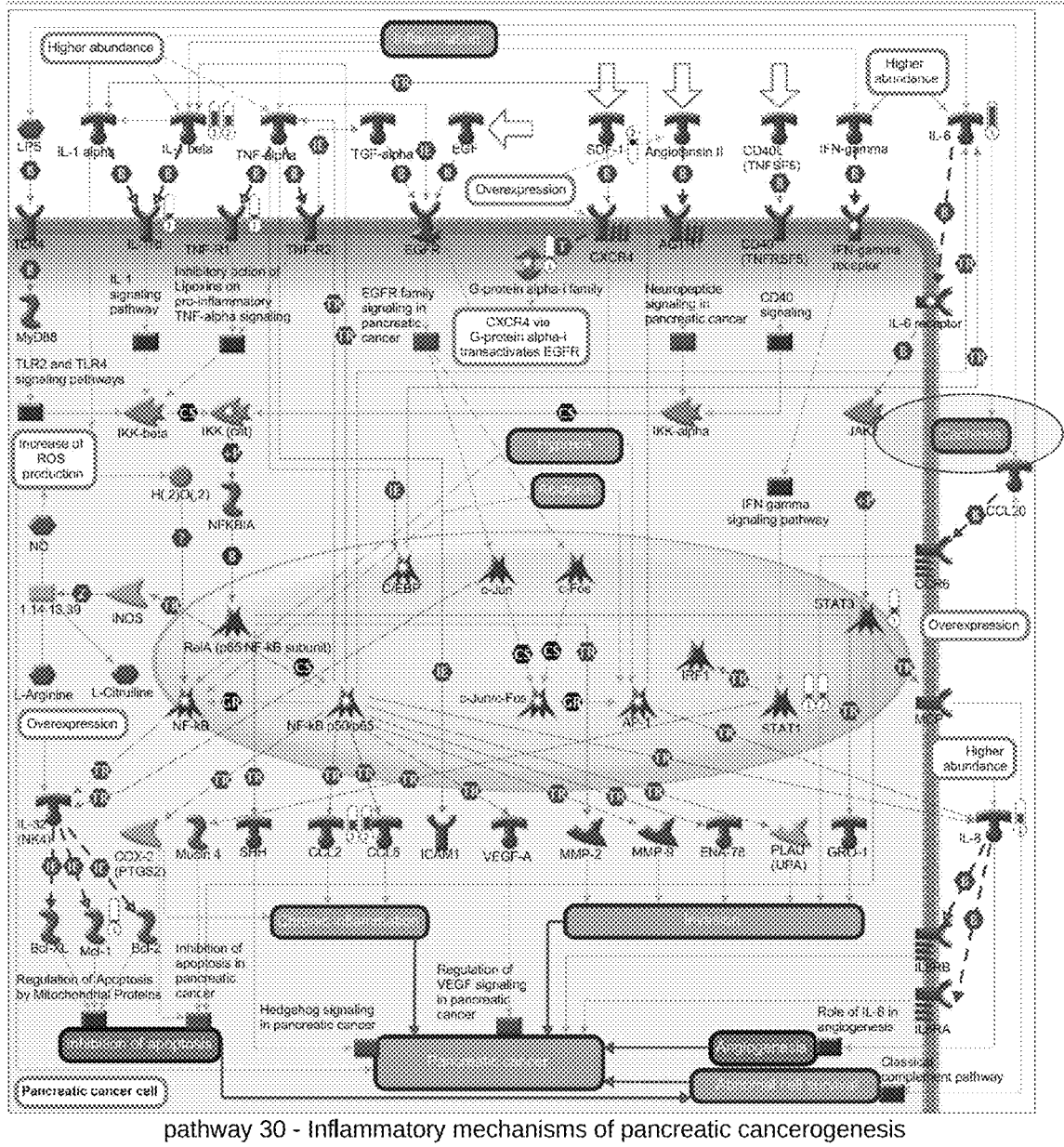
pathway 30 - Inflammatory mechanisms of pancreatic cancerogenesis

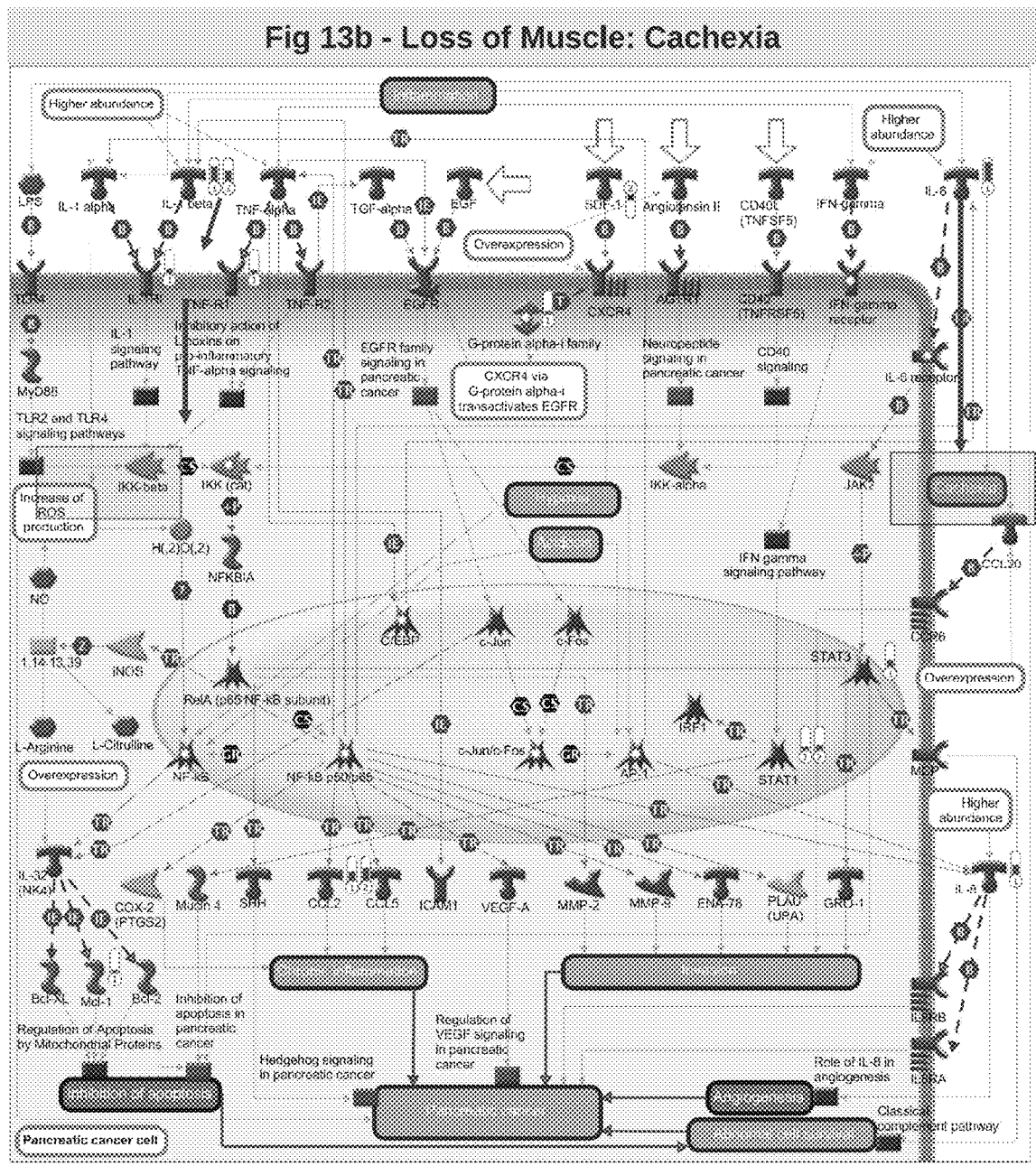

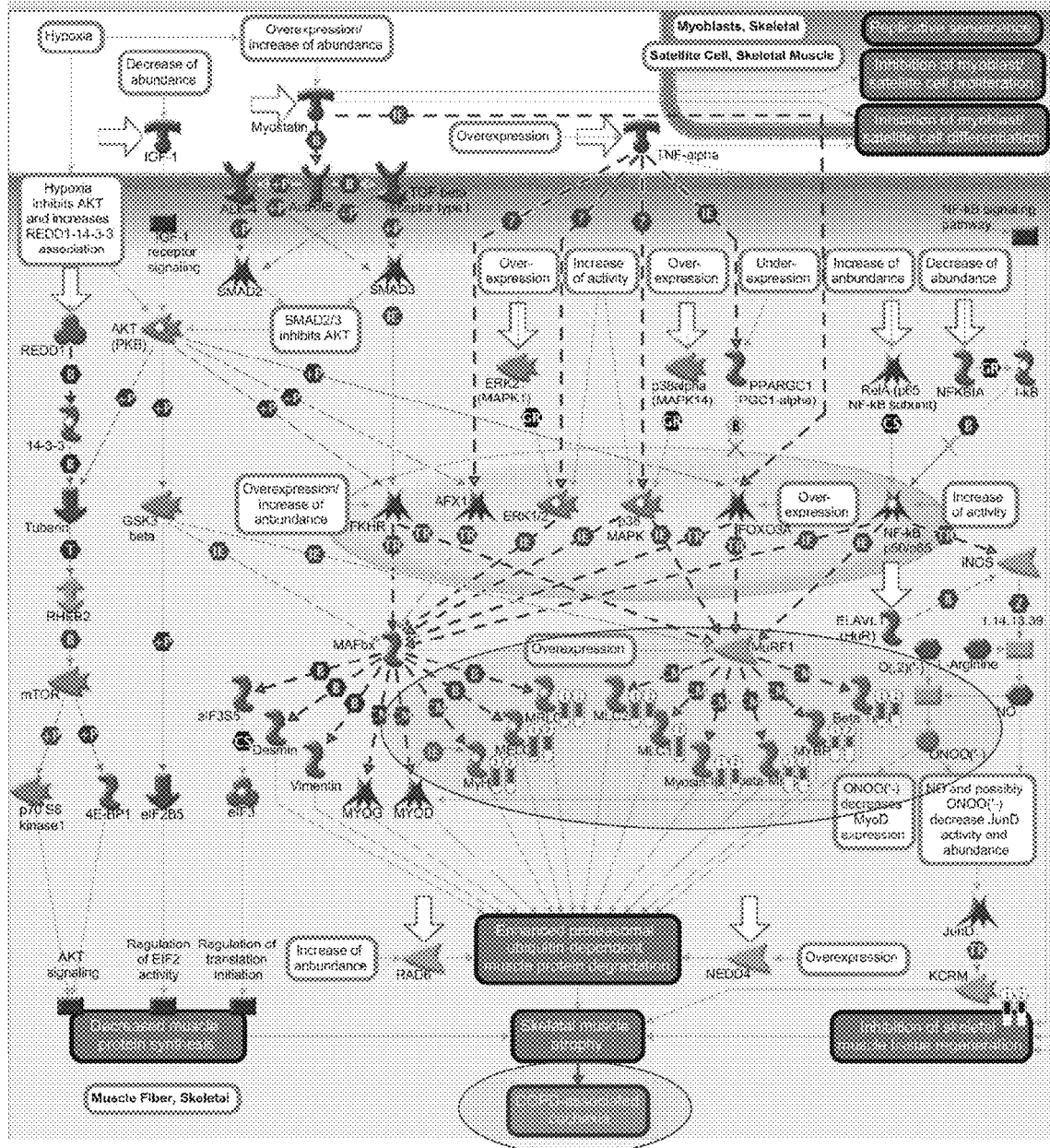
pathway 05 - Skeletal muscle atrophy in COPD

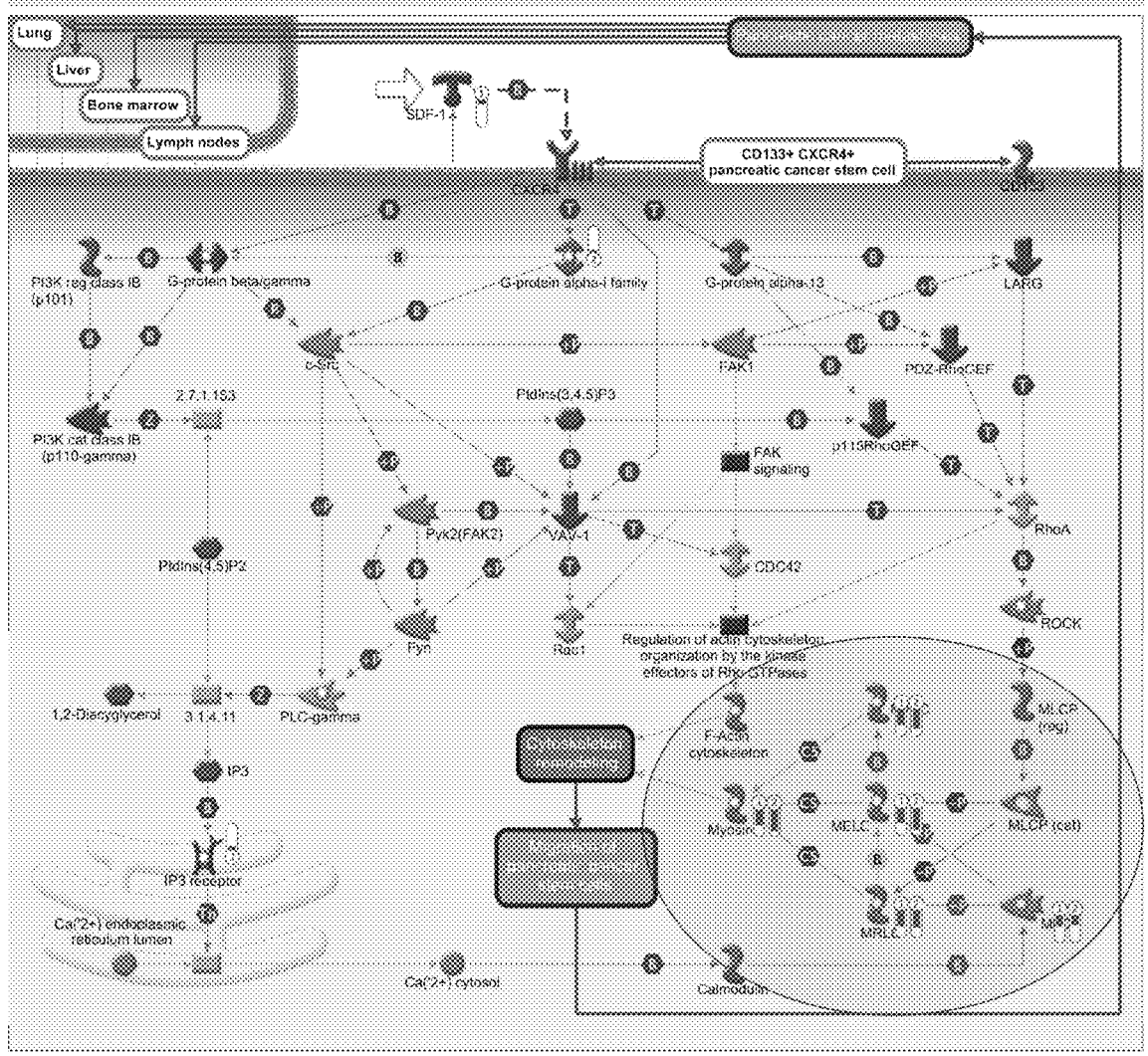
pathway 21 - Pancreatic cancer stem cells in tumor metastasis (stem cells)

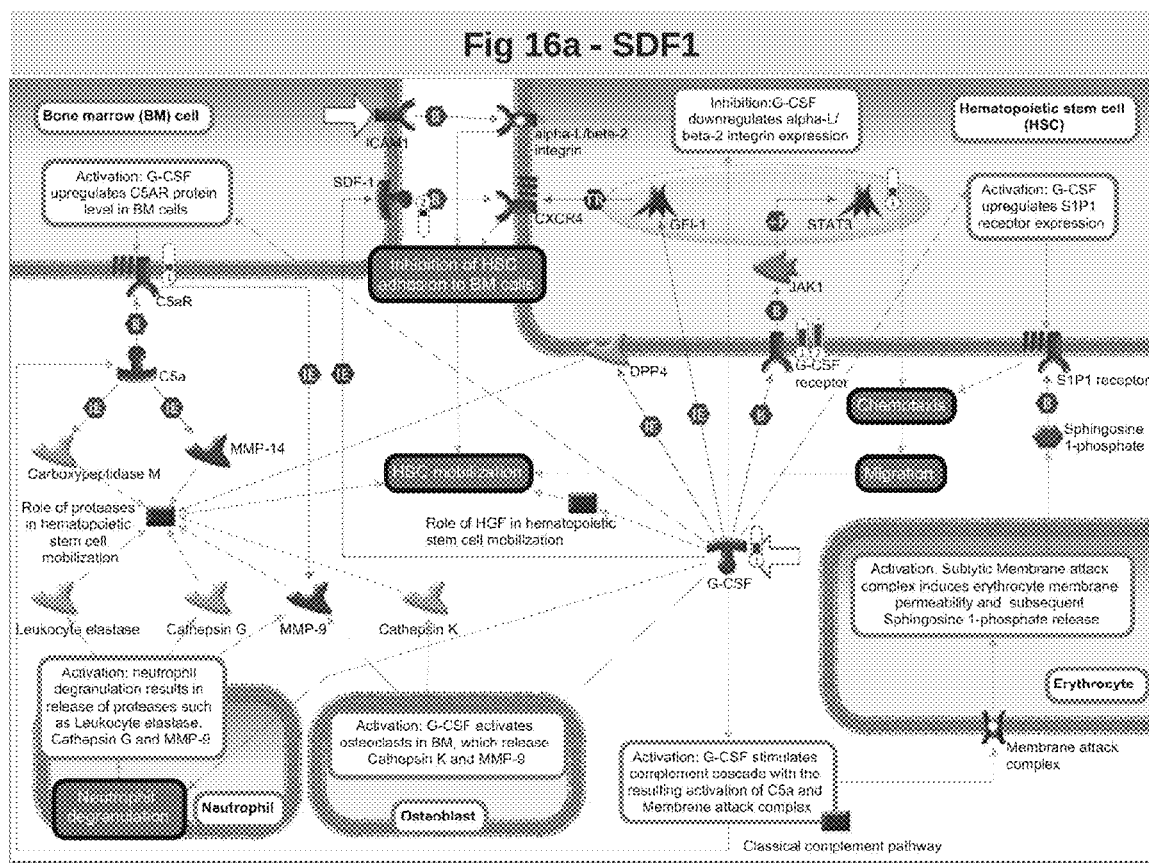
pathway163 – Development - Role of G-CSF in hematopoietic stem cell mobilization

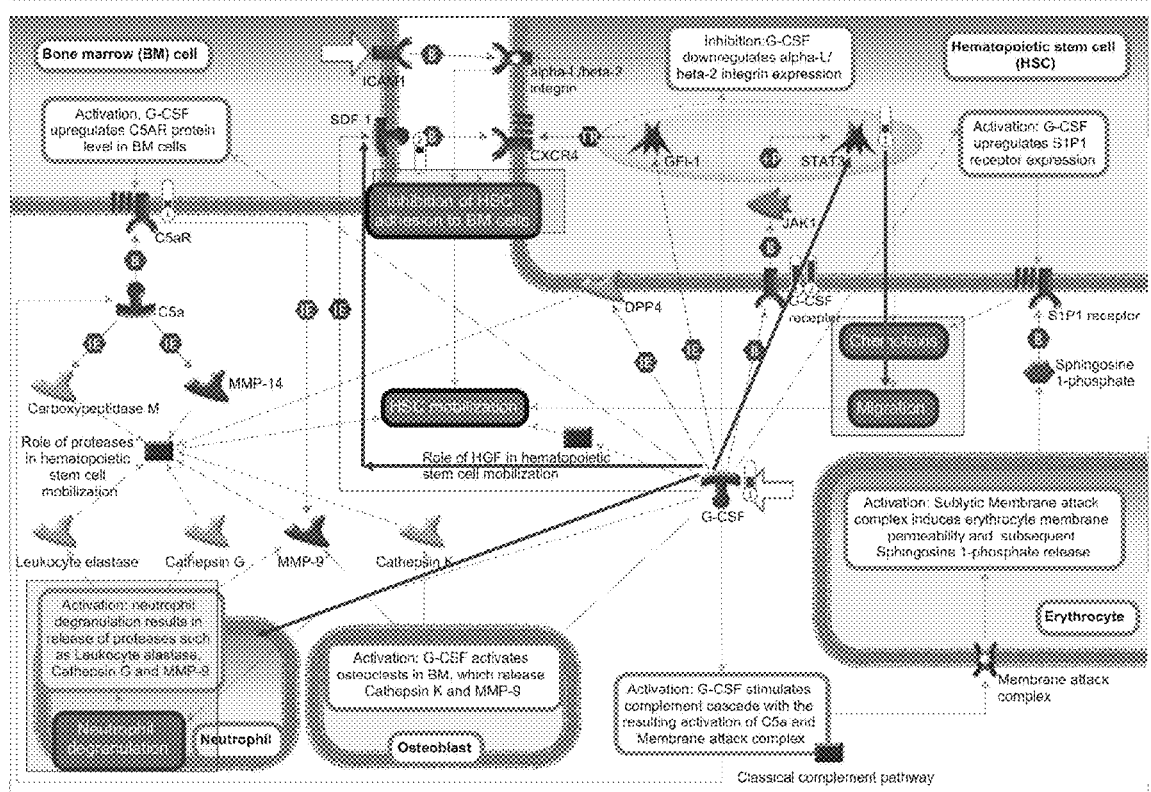

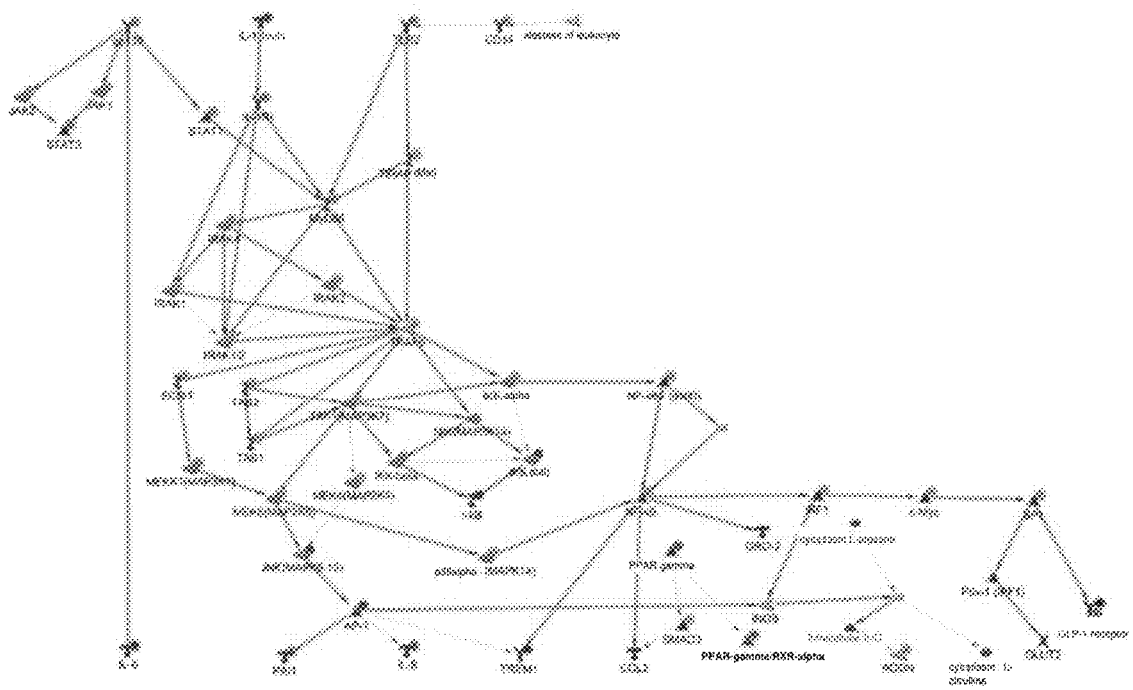

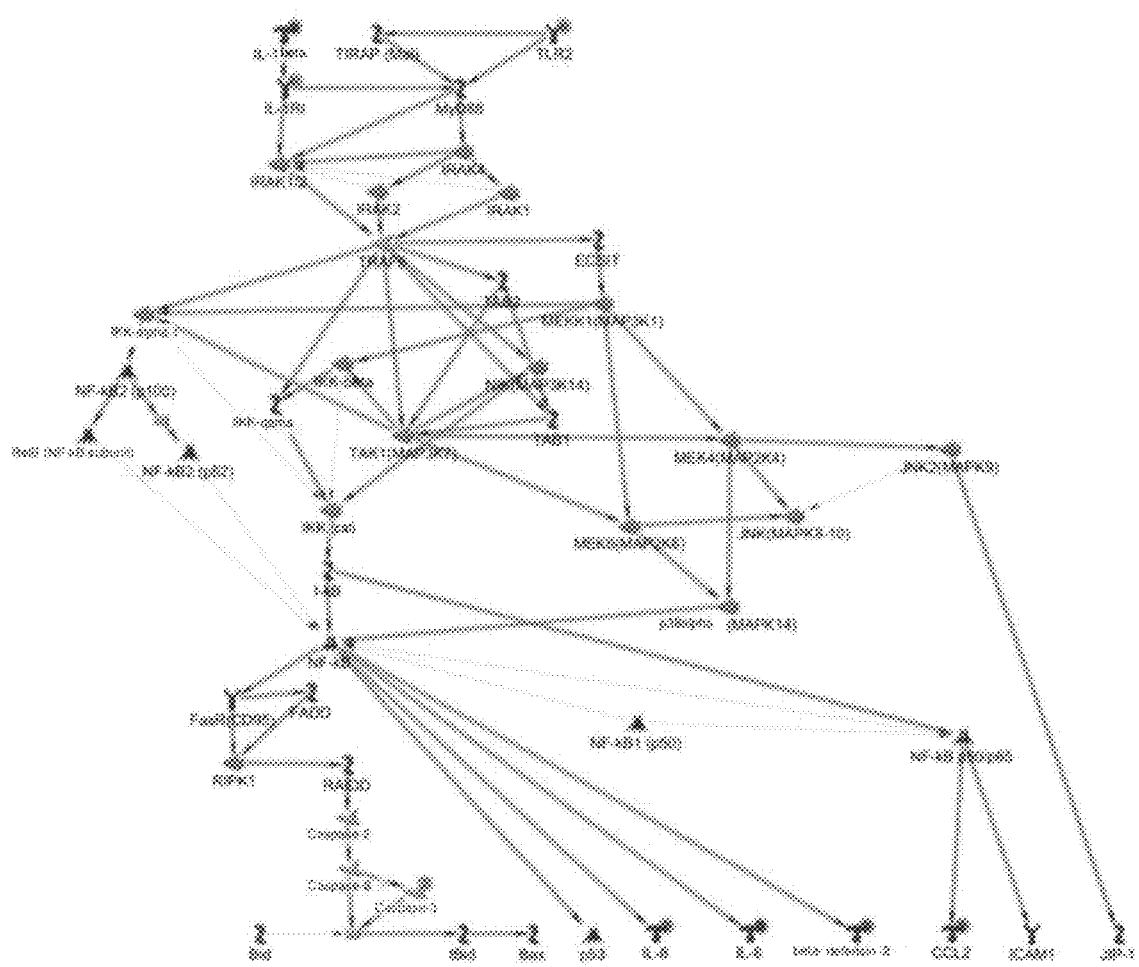

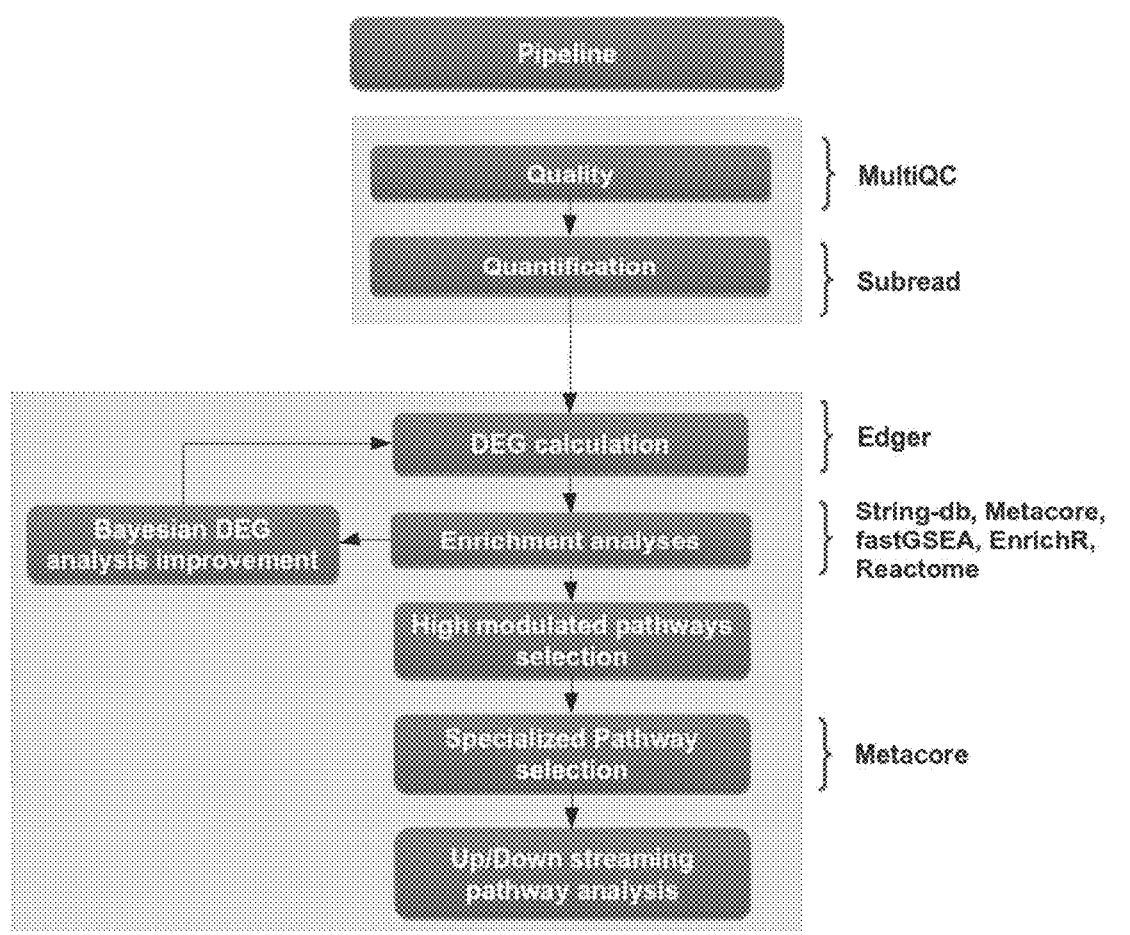

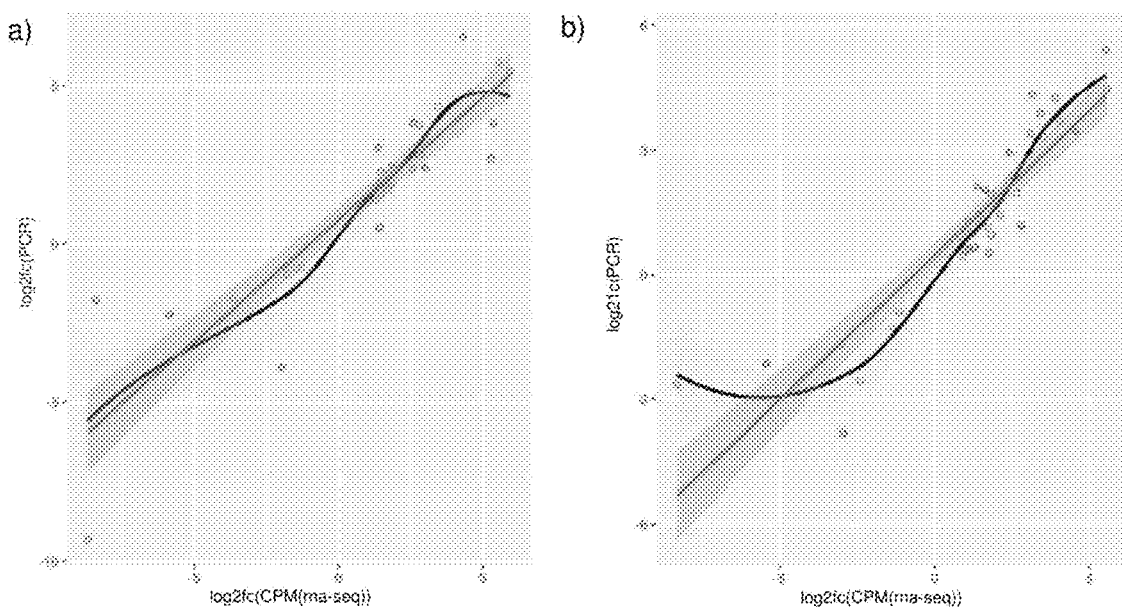

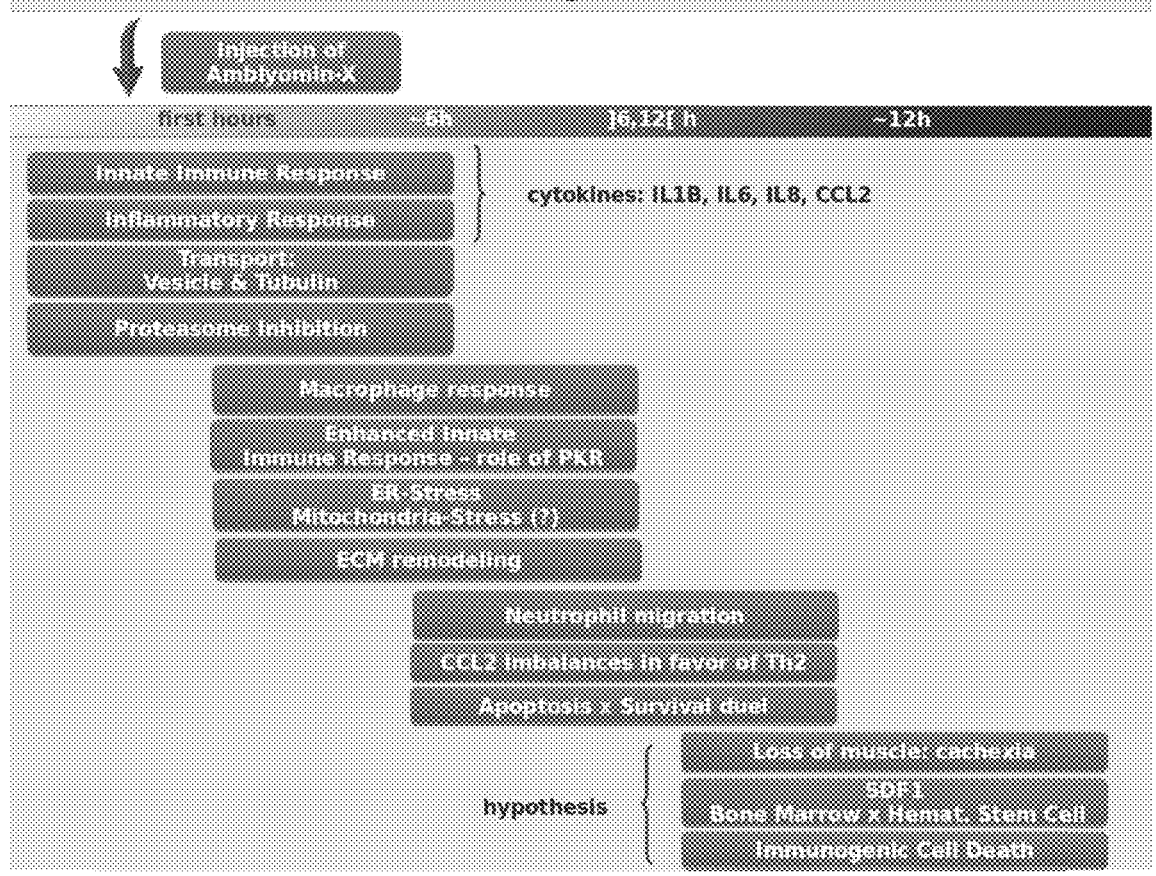

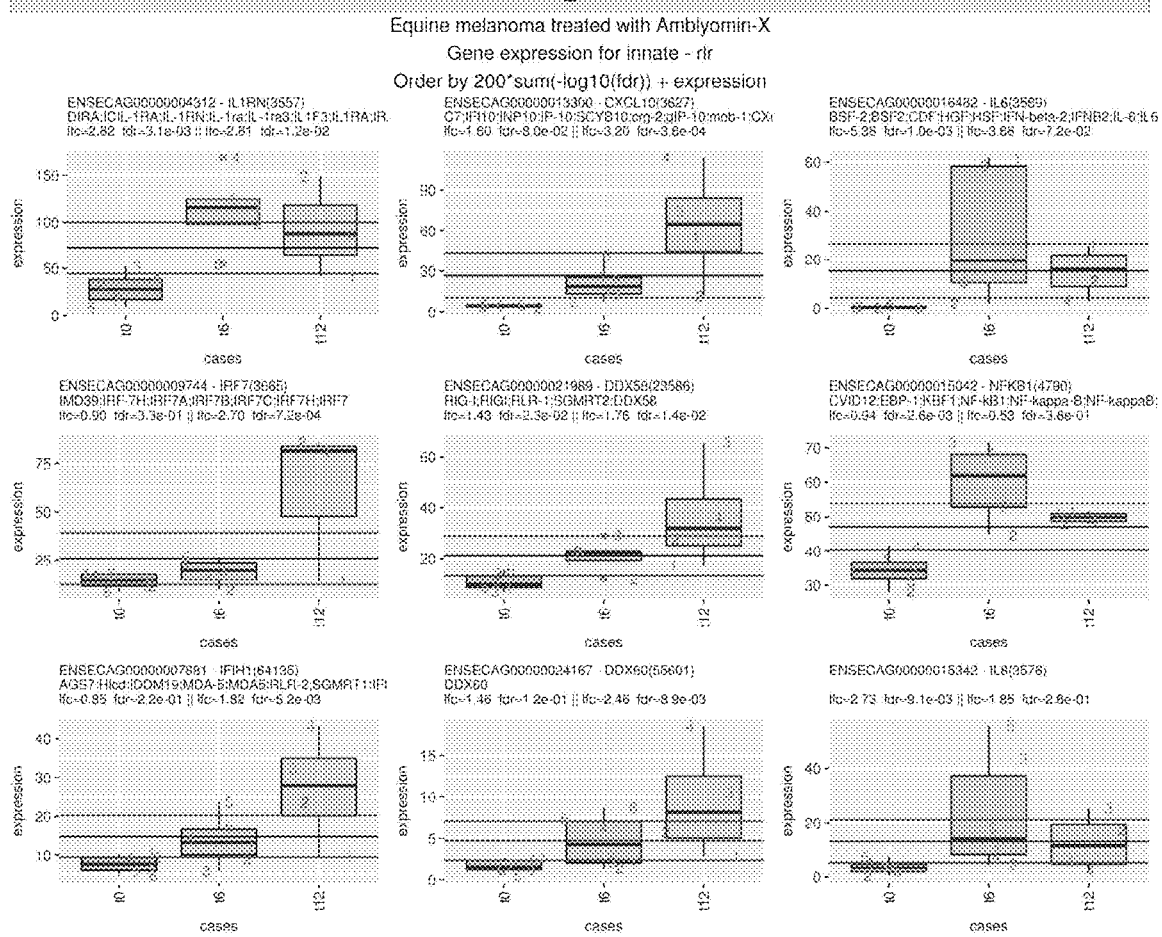

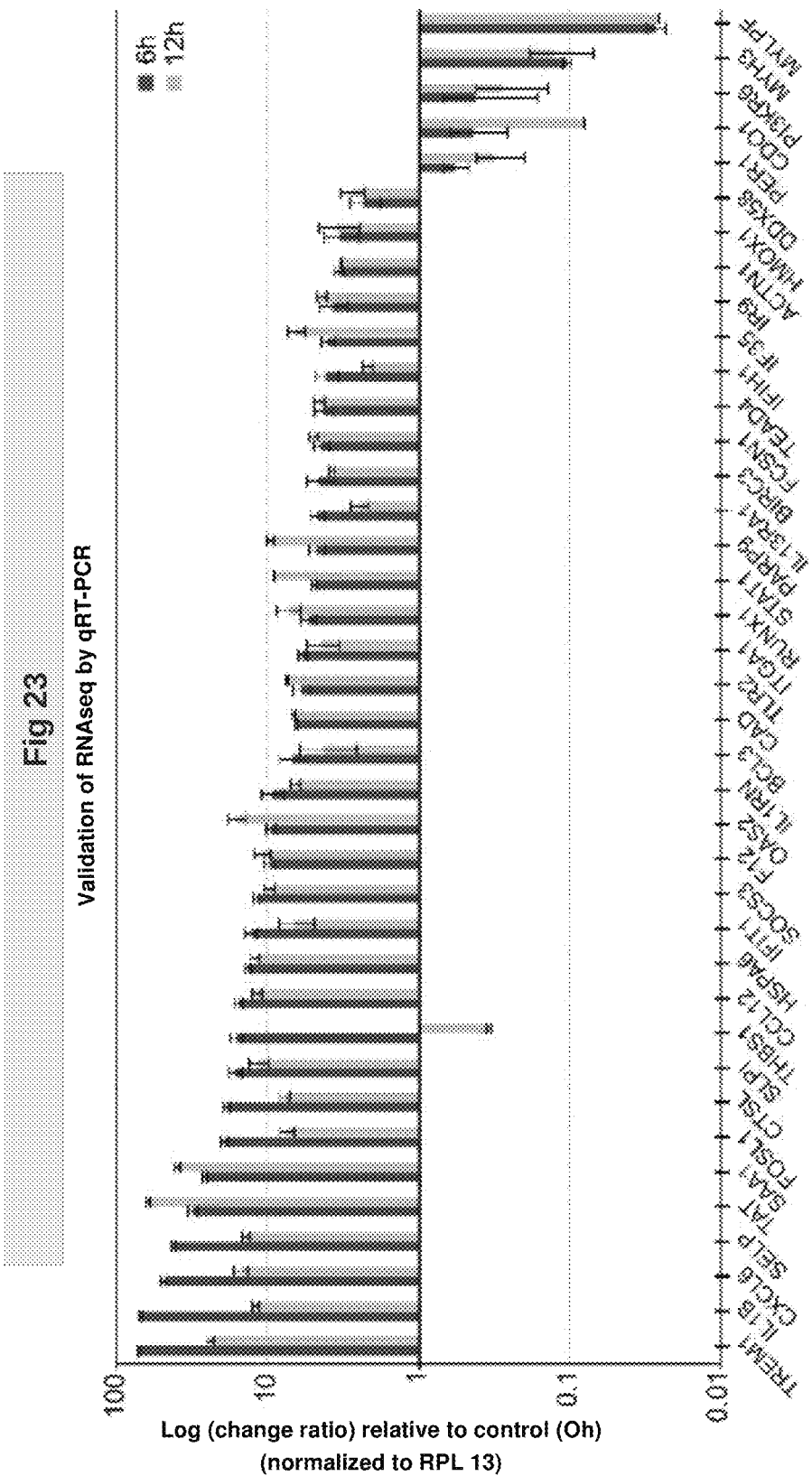

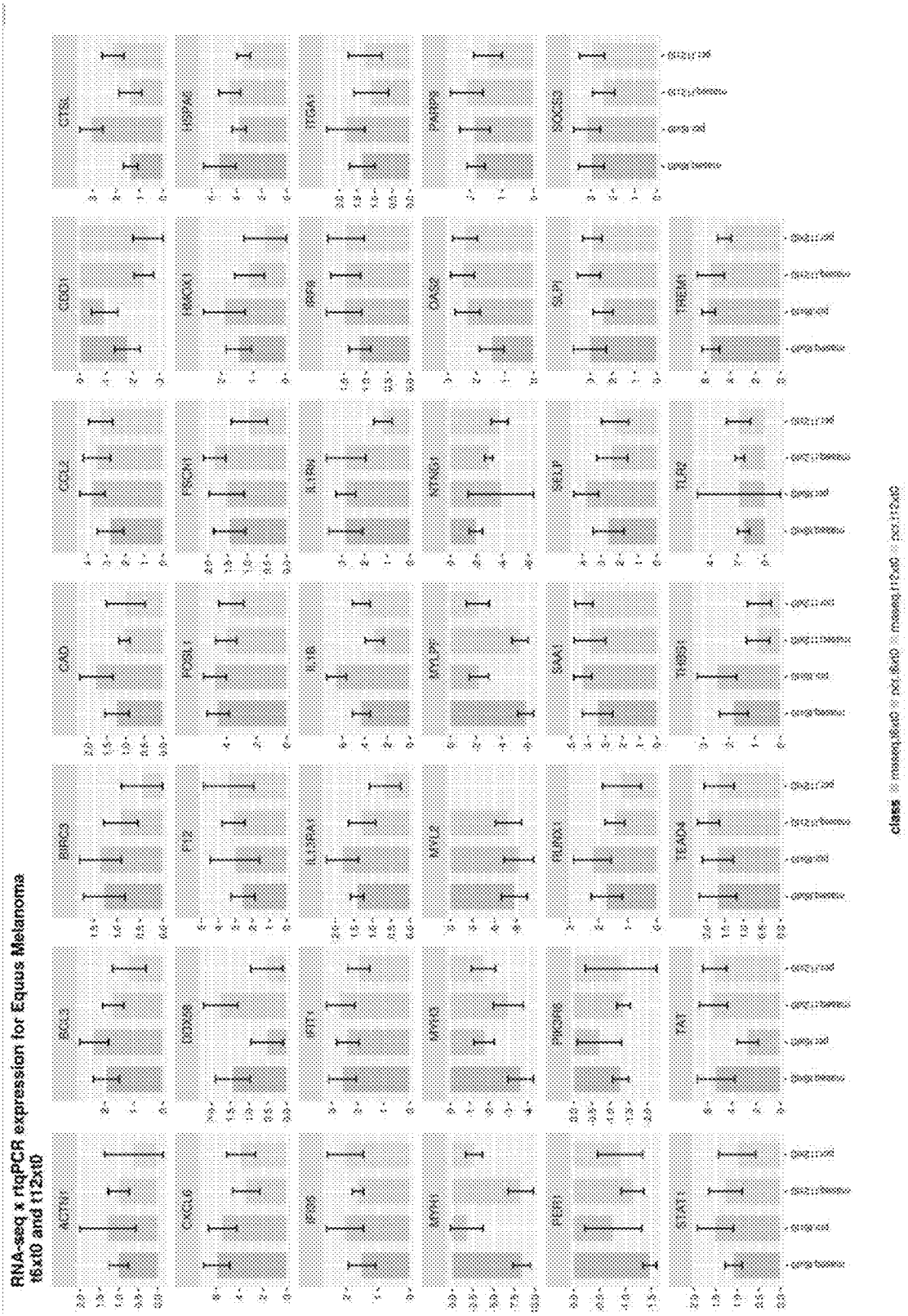

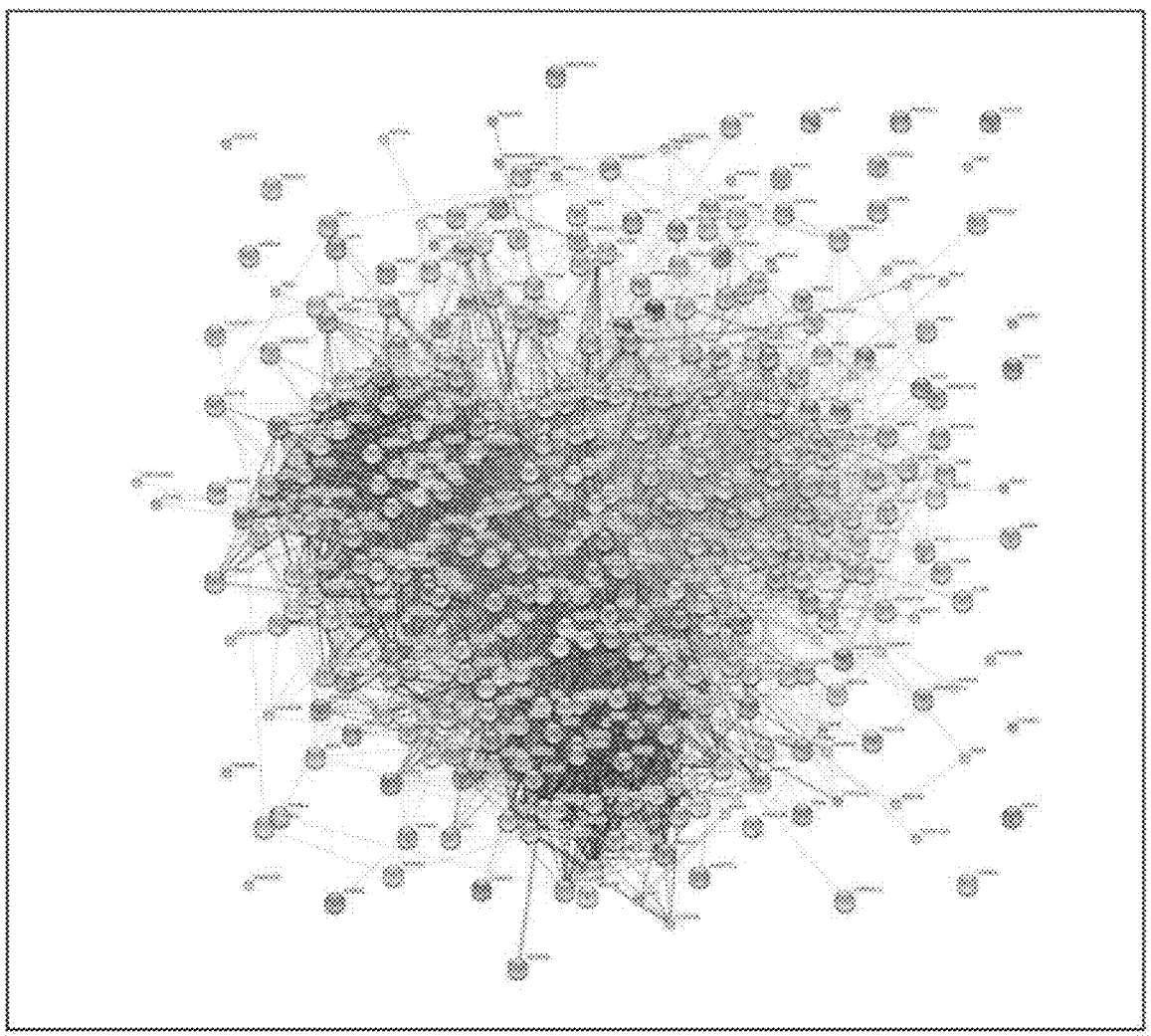

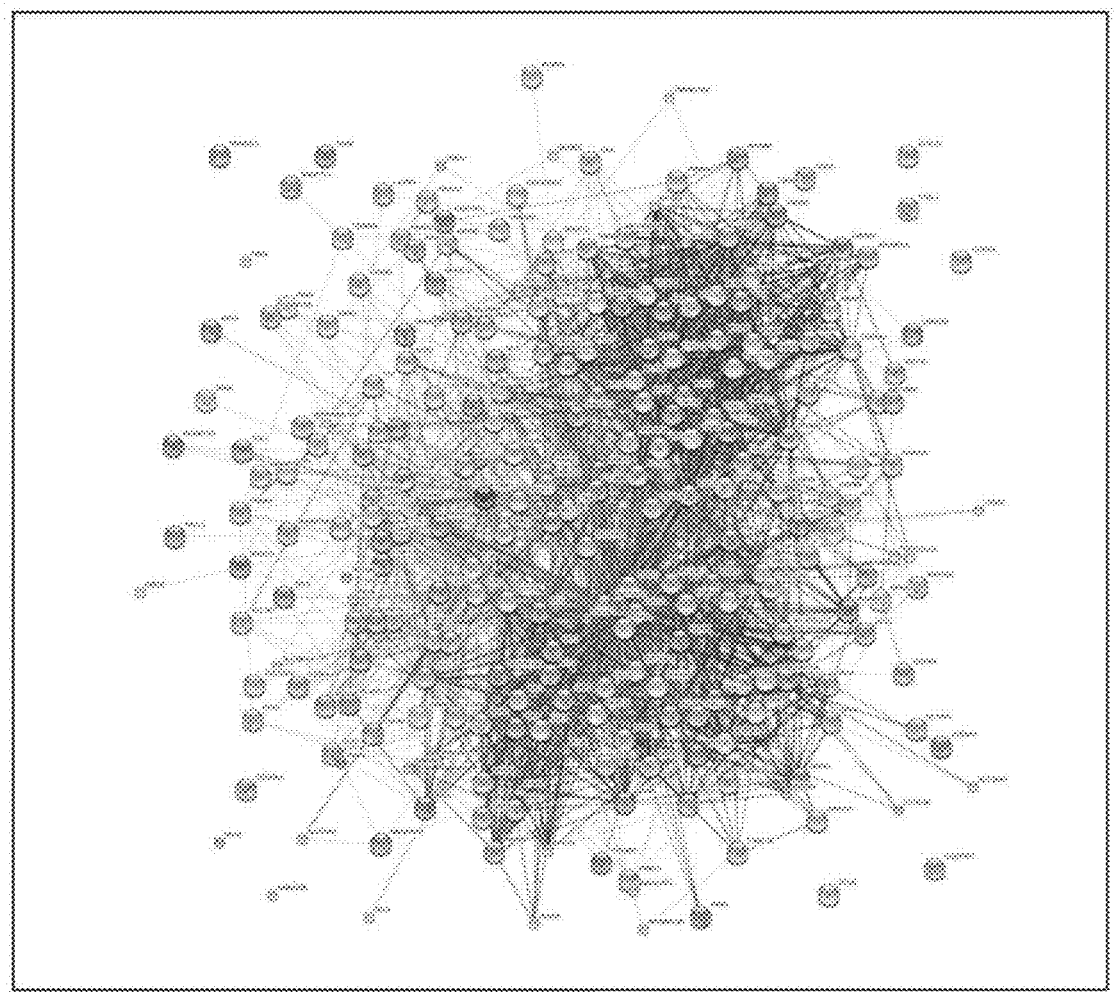

SEQUENCE LISTING

<160> NUMBER OF SEQ ID NOS: 9

<210> SEQ ID NO 1
<211> LENGTH: 129
<212> TYPE: PRT
<213> ORGANISM: Artificial sequence
<220> FEATURE:
<223> OTHER INFORMATION: Amblyomin-X

<400> SEQUENCE: 1

Met Arg Gln Leu Ala Val Leu Ala Leu Val Ile Phe Thr Gly Met Cys
1               5                   10                  15

Val Glu Ser Gln Ser Ala Asn Ser Lys Ala Val Cys Asn Leu Pro Lys
            20                  25                  30

Leu Ala Gly Asp Glu Thr Cys Ser Asn Lys Thr Glu Ile Arg Trp Tyr

```
                35                  40                  45
Tyr Asn Gly Thr Ala Cys Glu Ala Phe Ile Phe Lys Gly Cys Gly Gly
 50                  55                  60

Asn Asp Asn Asn Phe Asp Arg Val Asp Asp Cys Gln Arg Leu Cys Glu
 65                  70                  75                  80

Glu Gln Thr His Phe His Phe Glu Ser Pro Lys Leu Ile Cys Phe Lys
                 85                  90                  95

Val Gln Asp Tyr Trp Ile Leu Asn Asp Ile Met Lys Lys Asn Leu Thr
                100                 105                 110

Gly Ile Ser Leu Lys Ser Glu Glu Glu Asp Ala Asp Ser Gly Glu Ile
                115                 120                 125

Asp

<210> SEQ ID NO 2
<211> LENGTH: 11
<212> TYPE: PRT
<213> ORGANISM: Artificial sequence
<220> FEATURE:
<223> OTHER INFORMATION: Synthetic peptide

<400> SEQUENCE: 2

Val Cys Asn Leu Pro Lys Leu Ala Gly Asp Glu
 1               5                  10

<210> SEQ ID NO 3
<211> LENGTH: 11
<212> TYPE: PRT
<213> ORGANISM: Artificial sequence
<220> FEATURE:
<223> OTHER INFORMATION: Synthetic peptide

<400> SEQUENCE: 3

Gly Asp Glu Thr Cys Ser Asn Lys Thr Glu Ile
 1               5                  10

<210> SEQ ID NO 4
<211> LENGTH: 14
<212> TYPE: PRT
<213> ORGANISM: Artificial sequence
<220> FEATURE:
<223> OTHER INFORMATION: Synthetic peptide

<400> SEQUENCE: 4

Ile Arg Trp Tyr Tyr Asn Gly Thr Ala Cys Glu Ala Phe Ile
 1               5                  10

<210> SEQ ID NO 5
<211> LENGTH: 11
<212> TYPE: PRT
<213> ORGANISM: Artificial sequence
<220> FEATURE:
<223> OTHER INFORMATION: Synthetic peptide

<400> SEQUENCE: 5

Lys Gly Cys Gly Gly Asn Asp Asn Asn Phe Asp
 1               5                  10

<210> SEQ ID NO 6
<211> LENGTH: 13
<212> TYPE: PRT
<213> ORGANISM: Artificial sequence
<220> FEATURE:
<223> OTHER INFORMATION: Synthetic peptide
```

```
<400> SEQUENCE: 6

Asn Asn Phe Asp Arg Val Asp Asp Cys Gln Arg Leu Cys
1               5                   10

<210> SEQ ID NO 7
<211> LENGTH: 13
<212> TYPE: PRT
<213> ORGANISM: Artificial sequence
<220> FEATURE:
<223> OTHER INFORMATION: Synthetic peptide

<400> SEQUENCE: 7

Asn Asn Phe Asp Arg Val Asp Asp Ser Gln Arg Leu Cys
1               5                   10

<210> SEQ ID NO 8
<211> LENGTH: 27
<212> TYPE: PRT
<213> ORGANISM: Artificial sequence
<220> FEATURE:
<223> OTHER INFORMATION: Synthetic peptide

<400> SEQUENCE: 8

Val Cys Asn Leu Pro Lys Leu Ala Gly Asp Glu Thr Cys Ser Asn Lys
1               5                   10                  15

Thr Glu Ile Arg Trp Tyr Tyr Asn Gly Thr Ala
            20                  25

<210> SEQ ID NO 9
<211> LENGTH: 29
<212> TYPE: PRT
<213> ORGANISM: Artificial sequence
<220> FEATURE:
<223> OTHER INFORMATION: Synthetic peptide

<400> SEQUENCE: 9

Gly Thr Ala Cys Glu Ala Phe Ile Phe Lys Gly Cys Gly Gly Asn Asp
1               5                   10                  15

Asn Asn Phe Asp Arg Val Asp Asp Cys Gln Arg Leu Cys
            20                  25
```

COMPOUND FOR MODULATING RLR, TLR, OAS AND/OR ONCOSTATIN M PATHWAYS, USE THEREOF FOR PREPARING A MEDICINE, COMPOSITION, METHOD FOR MODULATING SAID PATHWAYS AND METHOD OF TREATMENT

CROSS REFERENCE TO RELATED APPPLICATIONS

This application is a U.S. National Phase Application of PCT International Application Number PCT/BR2019/050502, filed on Nov. 22, 2019, designating the United States of America and published in the Portuguese language, which is an International Application of and claims the benefit of priority to Brazilian patent application Ser. No. 10/2018074043-1, filed on Nov. 22, 2018. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52(e). The name of the ASCII text file for the Sequence Listing is SeqList-DBLA005-001APC.txt, the date of creation of the ASCII text file is Oct. 28, 2021, and the size of the ASCII text file is 4 KB.

FIELD OF THE INVENTION

The invention is in the fields of the Pharmaceutical Sciences, Immunology and Methods for treating cancer. More specifically, it relates to a compound to modulate one or more innate immune pathways selected from RLR, TLR, OAS and/or Oncostatin M. The use of such compound in the preparation of medicines; a composition and a method to modulate said pathways; and a pharmaceutical composition comprising said compound are also described. The methods and compositions are described, and the substantial technical evidence supports the claimed matter.

BACKGROUND OF THE INVENTION

Amblyomin-X is a recombinant Kunitz type protein identified in a cDNA library of *Amblyomma sculptum* tick salivary glands[3]. Amblyomin-X has the ability to inhibit factor Xa in the blood coagulation cascade and triggers the apoptosis by activating the intrinsic pathway in tumor cells[4-6]. Some of the present inventors have demonstrated that Amblyomin-X causes cell death via proteasome inhibition and stress induction of the endoplasmic reticulum in murine renal adenocarcinoma cells (RENCA) as well as in melanoma (human Sk-mel-28 and murine B16F10 cell line), and in pancreas tumor (Mia-Paca-2 cells) 7-9. Furthermore, it is now known that Amblyomin-X is more eager to recognize tumor cells[10]. The present inventors have also recently shown that the Amblyomin-X has an immuno-modulatory activity mediated by the TCD8 response against kidney metastases in the lungs of Balb/c mice, according to the use of a renal tumor translational model.

In the search for the state of the art in scientific and patent literature, the following documents dealing with the topic were found:

1. Smith, S. H., Goldschmidt, M. H. & McManus, P. M. A Comparative Review of Melanocytic Neoplasms. Vet. Pathol. 39, 651-678 (2002).
2. Rissi, D. R., Fighera, R. A., Irigoyen, L. F., De Lacorte, F. D. & Barros, C. S. L. de. Melanoma maligno anaplasico em um egilino. Cienc. Rural 38, 2072-2075 (2008).
3. Batista, I. F. C. et al. Expressed sequence tags (ESTs) from the salivary glands of the tick *Amblyomma cajennense* (Acari: Ixodidae). Toxicon 51, 823-834 (2008).
4. Branco, V. G. et al. Amblyomin-X having a Kunitz-type homologous domain, is a noncompetitive inhibitor of FXa and induces anticoagulation in vitro and in vivo. Biochim. Biophys. Acta BBA—Proteins Proteomics 1864, 1428-1435 (2016).
5. Maria, D. A. et al. A novel proteasome inhibitor acting in mitochondrial dysfunction, ER stress and ROS production. Invest. New Drugs 31, 493-505 (2013).
6. Chudzinski-Tavassi, A. M., Morais, K. L. P., Pacheco, M. T. F., Pasqualoto, K. F. M. & de Souza, J. G. Tick salivary gland as potential natural source for the discovery of promising antitumor drug candidates. Biomed. Pharmacother. 77, 14-19 (2016). 7.Akagi, E. M. et al. Pro-apoptotic effects of Amblyomin-X in murine renal cell carcinoma "in vitro". Biomed. Pharmacother. 66, 64-69 (2012).
8. Chudzinski-Tavassi, A. M. et al. A new tick Kunitz type inhibitor, Amblyomin-X, induces tumor cell death by modulating genes related to the cell cycle and targeting the ubiquitin-proteasome system. Toxicon 56, 1145-1154 (2010).
9. Lopes, J. D. & Mariano, M. B-1 cell: the precursor of a novel mononuclear phagocyte with immuno-regulatory properties. An. Acad. Bras. Cienc. 81, 489-496 (2009).
10. de Souza, J. G. et al. Promising pharmacological profile of a Kunitz-type inhibitor in murine renal cell carcinoma model. Oncotarget 7, (2016).
11. Langmead, B. & Salzberg, S. L. Fast gapped-read alignment with Bowtie 2. Nat. Methods 9, 357-359 (2012).
12. Anders, S. & Huber, W. Differential expression analysis for sequence count data. Genome Biol. 11, R106 (2010).
13. Pfaffl, M. W. A new mathematical model for relative quantification in real-time RT-PCR. Nucleic Acids Res. 29, e45 (2001).
14. Kim, D., Langmead, B. & Salzberg, S. HISAT: Hierarchical Indexing for Spliced Alignment of Transcripts. (2014).
15. Liao, Y., Smyth, G. K. & Shi, W. The Subread aligner: fast, accurate and scalable read mapping by seed-and-vote. Nucleic Acids Res. 41, e108 - e108 (2013).
16. Robinson, M. D., McCarthy, D. J. & Smyth, G. K. edgeR: a Bioconductor package for differential expression analysis of digital gene expression data. Bioinformatics 26, 139-140 (2010).
17. Franceschini, A. et al. STRING v9.1: protein-protein interaction networks, with increased coverage and integration. Nucleic Acids Res. 41, D808 - D815 (2013).
18. Sergushichev, A. An algorithm for fast preranked gene set enrichment analysis using cumulative statistic calculation. (2016). doi:10.1101/060012 19. Chen, E. Y. et al. Enrichr: interactive and collaborative HTML5 gene list enrichment analysis tool. BMC Bioinformatics 14, 128 (2013).
20. Kuleshov, M. V. et al. Enrichr: a comprehensive gene set enrichment analysis web server 2016 update. Nucleic Acids Res. 44, W90 - W97 (2016).
21. Langfelder, P. & Horvath, S. WGCNA: an R package for weighted correlation network analysis. BMC Bioinformatics 9, 1 - 13 (2008).
22. Russo, P. S. T. et al. CEMiTool: a Bioconductor package for performing comprehensive modular co-expression analyses. BMC Bioinformatics 19, (2018).

23. The R Development Core Team. R: A Language and Environment for Statistical Computing. (2008).

24. Csardi, G. & Nepusz, T. The igraph software package for complex network researc. InterJournal Complex Systems, 1695 (2006).

25. Kanehisa, M., Sato, Y., Kawashima, M., Furumichi, M. & Tanabe, M. KEGG as a reference resource for gene and protein annotation. Nucleic Acids Res 44, D457 - D462 (2016). 26. Gene Ontology Consortium. Gene Ontology Consortium: going forward. Nucl Acids Res 43, D1049 - D1056 (2015).

27. Finn, R. D. et al. The Pfam protein families database: towards a more sustainable future. Nucleic Acids Res. 44, D279 - D285 (2016).

28. Subramanian, A. et al. Gene set enrichment analysis: A knowledge-based approach for interpreting genome-wide expression profiles. PNAS 102, 15545-15550 (2005).

29. Duan, Q. et al. L1000CDS2: LINCS L1000 characteristic direction signatures search engine. Npj Syst. Biol. Appl. 2, (2016).

30. Pacheco, M. T. F. et al. Dynein Function and Protein Clearance Changes in Tumor Cells Induced by a Kunitz-Type Molecule, Amblyomin-X. PLoS ONE 9, e111907 (2014).

31. Morais, K. L. P. et al. Amblyomin-X induces ER stress, mitochondrial dysfunction, and caspase activation in human melanoma and pancreatic tumor cell. Mol. Cell. Biochem. 415, 119-131 (2016).

32. Mogensen, T. H. Pathogen Recognition and Inflammatory Signaling in Innate Immune Defenses. Clin. Microbiol. Rev. 22, 240-273 (2009).

33. Mignogna, C. et al. Innate immunity in cutaneous melanoma. Clin. Exp. Dermatol. 42, 243-250 (2017).

34. Yu, X. et al. Activation of the MDA-5-IPS-1 Viral Sensing Pathway Induces Cancer Cell Death and Type I IFN-Dependent Antitumor Immunity. Cancer Res. 76, 2166-2176 (2016). 35. Colonna, M. TLR pathways and IFN-regulatory factors: To each its own. Eur. J. Immunol. 37, 306-309 (2007).

36. Ohman, T., Rintahaka, J., Kalkkinen, N., Matikainen, S. & Nyman, T. A. Actin and RIG-I/MAVS Signaling Components Translocate to Mitochondria upon Influenza A Virus Infection of Human Primary Macrophages. J. Immunol. 182, 5682-5692 (2009).

37. Jheng, J.-R., Ho, J.-Y. & Horng, J.-T. ER stress, autophagy, and RNA viruses. Front. Microbiol. 5, (2014).

Document U.S. Pat. No. 8,449,795 of the present inventors describes Amblyomin-X as a coagulation cascade X factor inhibitor and its use as an antitumor agent. Such document does not reveal nor suggest the subject matter of the present invention.

Thus, from what is learned from the researched literature, no documents anticipating or suggesting the teachings of the present invention were found, so that the solution herein proposed has novelty and inventive step in view of the state of the art.

SUMMARY OF THE INVENTION

The present invention provides for a compound to modulate one or more innate immune pathways selected from RLR, TLR, OAS and/or Oncostatin M.

The present invention also provides for: the use of said compound in the preparation of medicines; a composition and method to modulate said pathways; and a pharmaceutical composition comprising said compound is also described.

The compound of the present invention is a synthetic peptide selected from: Amblyomin-X (Seq ID No. 1); the peptides VCNLPKLAGDE (Seq ID No. 2), GDETCSNK-TEI (Seq ID No. 3); IRWYYNGTACEAFI (Seq ID No. 4), KGCGGNDNNFD (Seq ID No. 5), NNFDRVDDCQRLC (Seq ID No. 6), NNFDRVDDSQRLC (Seq ID No. 7), VCNLPKLAGDETCSNKTEIRWYYNGTA (Seq ID No. 8), GTACEAFIFKGCGGNDNNFDRVDDCQRLC (Seq ID No. 9); or combinations thereof.

The results of multiple experiments with the compound and the composition of the invention show the modulation of ER-stress, upregulation of CALR, and apoptosis. In one embodiment, the in vivo administration of the compound of the invention results in a cell destiny consistent with an immunogenic cell death (ICD) response.

This and other objects of the invention will be more easily valued by the attached claims and by the evidence provided in the detailed description below.

BRIEF DESCRIPTION OF THE FIGURES

FIG. 1 shows a scheme of the primary responses relating Function and DEGs.

FIGS. 1A and 1B show the pathway of the RIG-type receptor: three DNA/RNA sensors are upregulated in the RLR pathway: RIG-I, LGP2 and MDAS.
1) DDX60 is also upregulated, not shown herein;
2) The pathway next step is the interaction with mitochondrial proteins, such as VISA (MAVS);
3) Two distinct pathways are possible: a) IKK-epsilon or TBK1 pathway; b) IKK-beta pathway for IKK. IKK, IKK-beta and IKK-epsilon are moderately expressed, but not modulated;
4) IKK-epsilon or TBK1 along with the IRF7 transcription factor (DEG) induce the transcription of IFN alpha and IFN beta, but these last two transcriptions have no expression (zero reads);
5) IKK-beta- IKK, via IKB * and NFKB * induces IL-8 and E-selection, the latter genes are positively regulated DEGs. (* means phosphorylated);
6) Using the KEGG database, the following cytokines are upregulated: IL-8 and IP-10 (positively regulated DEG) and TNF-alpha and IL-12 expressed but not modulated.

FIGS. 2A and 2B show Tubulin 1) Importin beta is an upstream effector, an upregulated DEG; 2) There are several downstream pathways: CREB1— Nucleolin, ELAVL— Nucleolin, importin alpha; 3) TUBB and TUBB6 are upregulated DEGs, and downstream genes. TUBB2B and TUBB3 are moderately expressed but are not modulated. Tubulin is an important protein related to microtubules, which in turn plays an important role in cell transportation and in maintaining the cytoskeleton structure. Beta tubulin forms a dimer with alpha tubulin and acts as a structural component of microtubules. Tubulins, HTT (huntingtin), RAB35, RAB31 and RAB8B are modulated and may present some relation with vesicular transport.

FIG. 3 is a schematic of the secondary responses relating Function and DEGs.

FIGS. 3A and 3B show the response of macrophages:
1) IL1B and IFN gamma— TLR2 are upstream effectors;
2) NFKB plays a central role, being an important mediator in the transcription of many cytokines; 3) Downstream transcripts: IL-6, IP10, IL8, CCL2 - upregulated cytokines. IL8 and IP10 are upregulated in RLR macrophage signaling pathways. 5) TNF (tumor necrosis factor) is weakly expressed and is not modulated. TNFRSF1A is an TNF-alpha receptor and an upregulated DEG. TNFAIP2 and TNFAIP6, genes whose expression can be induced by TNF-alpha in endothelial cells, are upregulated DEGs. IP10 and CCL2 are related to chemotaxis of inflammatory cells. CCL2 is also upregulated after 12 h. IL8, which plays a role in neutrophil migration, is upregulated after 6 h. Looking closely at the data, IL6 is upregulated (almost DEG after 6 h, and DEG after 12 h), playing a central role in inflammation.

FIGS. 4A and 4B show 1) The Interferon signaling pathway is a very important pathway for the present study. A good interferon response is mandatory for the future discovery of drugs related to the immune system. In the present study, it is not possible to see the expression of IFN-alpha, IFN-beta and IFN-gamma. But these upstream effectors have many downstream genes with expression, modulation and many DEGs. 2) STAT1, IRF9 and STAT2 are important transcription factors and are upregulated DEGs. 3) ISGF3 (IRF9 - Regulatory Factor 9 of Interferon) is a key transcription factor related to the secondary innate immune response, which induces the transcription of three different OAS genes (2'-5' oligoadenylate synthase 1, 2, and 3); 4) WARS and PKR (EIF2AK2 - Eukaryotic Translation Initiation Factor 2 Alpha Kinase 2 or Protein kinase R, Interferon-Induced Inducible Double-Strand RNA) are upregulated DEGs. If there is a viral invasion, both genes would play a key role in regulating the biosynthesis of viral proteins.

FIGS. 5A and 5B show the Oncostatin M pathway. Oncostatin M is an important signaling pathway for the immune system. OSM is proteolytically processed to produce the mature protein that will be secreted. OSM has the ability to inhibit the proliferation of a number of tumor cell lines. 1) Regulates the production of cytokines such as: IL-6, G-CSF, and GM-CSF of endothelial cells, according to the Uniprot; 2) According to Metacore, it induces the transcription of CCL2 and SERPINA (Serine Protease Inhibitor A3), through STAT3 and STAT1, regulated by SOCS3. 3) MMP-1 is down regulated and is it not in accordance with the pathway.

FIGS. 6A and 6B show the PKR IL1B pathway -response to antiviral stress. IL1B is the main effector of this pathway. 1) The TNF-alpha CASP3 PKR pathway may also be present. 2) IL1B through its upregulated receptor (IL1-RI) MYD88 PKR reaches the nucleus and several transcription factors (RELA (p65), NFKB (p50/p65), NFKB*) induces the transcription of several cytokines, such as: IL6 and IL8. IL10 and TNF-alpha has low expression and low modulation, not in accordance with the prediction of the pathway. 3) The MAP2K6 MAPK14 STAT1 pathway induces BAFF transcription (TNFSF13B), but it was not possible to observe any significant expression.

FIGS. 7A and 7B show if HMGB1 is an effector. 1) According to Uniprot, HBGB1 is the pleiotropic protein involved in DNA remodeling, replication, chromatin transcription, DNA repair and its stability. In the cytoplasm, HBGB1 functions as a sensor and/or chaperone for immunogenic nucleic acids, implying the activation of the immune response of the mediator TLR9, and mediates in autophagy. It also acts as a DAMP that amplifies immune responses during tissue damage. Released to the extracellular environment, it can bind to DNA, nucleosomes, IL-1 beta, CXCL12, isoform AGER 2/sRAGE, liposaccharide (LPS) and lipoteichoic acid (LTA) and activates cells through the engagement of multiple receptor surfaces. In the completely reduced extracellular compartment, HMGB1 (released by necrosis) acts as a chemokine, HMGB1 disulfide (actively secreted) as a cytokine, and HMGB1 sulfonyl (released from apoptotic cells) promotes immune tolerance. It binds to phosphatidylserine and phosphatidylethanolamide. 2) There is a possible RAGE response via NFKB and cJUN. 3) It is very likely that HMGB1 was released in some apoptotic death and induced the production of several cytokines such as: IL6, IL1B, IL8, IL1RN, and also SERPINE1 (PAIl, Serpine Peptidase Inhibitor, Clade E) and CHGA (Chromogranin A, found in neurons and endocrine cells).

FIGS. 8A and 8B show the ER stress signal. In this pathway, it is possible to see the ER stress signal. ER stress can be achieved by different causes, the proteasome inhibition related to treatment with Amblyomin-X may be the main reason. 1) ATF6 and GRP78 are the main upstream effectors, both are upregulated DEGs in 6 h. 2) IRE1 (ERN1-Endoplasmic Reticulum Signaling for Nucleus 1) is upregulated, but it has a very low expression. 3) IP3R1 (ITPR1) is a inositol 1,4,5-triphosphate intracellular receptor. Upon stimulation by inositol 1,4,5-triphosphate, this receptor mediates calcium release from the ER (RefSeq, November of 2009). It is an upregulated DEG in 6 h. 4) Another three DEGs are: XBP1, ERP5 (PDIA6), and Endoplasmin (HSP90B1). 5) According to NCBI, XBP1 loses 26 nt of the spliced mRNA causes a change in frame and an isoform of XBP1 (S), which is the functionally active transcription factor. The isoform encoded by the unamended mRna, XBP1 (U), is constitutively expressed, and thought to work as a negative feedback regulator of XBP1 (S), which terminates the transcription of target genes during the ER stress recovery phase (RefSeq, July of 2008). 6) ERP5 (PDIA6—Disulfide Isomerase Protein Family Member A 6)—catalyzes the folding of the protein and exhibits both isomerase and chaperone activity. (RefSeq, December of 2016). 7) Endoplasmin (HSP90B1-Heat Shock Protein 90 Beta Family Member 1) is a chaperone with functions to stabilize and fold other proteins, it is located for melanosomes and the endoplasmic reticulum (ER). The expression of this protein is associated with a variety of pathogenic conditions, including tumor formation. (RefSeq, August of 2012) 8) The main function of DEGs is to correct the folding and survival. But DERL1, DERL2, HERP (slightly down-regulated) and the EDEM family (1,2,3) have good expression leading to degradation.

FIGS. 9A and 9B show the ER and Mitochondria Stress. 1) IP3R1 and possibly $Ca+^2$ are middle stream signals of released ER stress 2) Calpain-2 and HSP60 must be upregulated as a result of $Ca+^2$ release 3) Calpain-2 promotes and HSP60 inhibits Bax, resulting in the upregulation of Cytochrome c and possible mitochondria release. In consequence, CASP3 is upregulated. 4) In the central part of the pathway diagram, one can observe ATF6 (p50 KDa) inducing the transcription of Calreticulin (CALR) and Endoplasmin (HSP90B1). CALR has several functions including the induction of Immunogenic Cell Death (ICD), and HSP90B1 is a chaperone described in one of the previous paragraphs.

FIGS. 10A and 10B show the oxidative stress and the apoptosis. 1) Oxidative stress induced by cigarette smoke and the apoptosis pathway partially represent what is happening in Amblyomin-X treatment related to possible oxidative stress; 2) SOD2 GRP79 BCL2 is an upregulated pathway. The MCL-1 upstream is not well understood. Both can lead to the release of Cytochrome c from mitochondria. 3) The final downstream is the upregulated CASP3 and CASP4 leading to apoptosis. 4) It has been hypothesized that Cytochrome c CASP9 CASP3, CASP4 induces apoptosis. This pathway is the closest related to treatment with Amblyomin-X, ER and oxidative stress, resulting in programmed cell death. 5) CASP9 has low expression at 0 h and 6 h, and almost zero at 12 h. It must be remembered that the apoptosis pathway has many post-translational transformations, thus many processes cannot be seen by RNA-Seq experiments. 6) VDAC1 is a highly transcribed but not modulated Voltage-Dependent Anionic Channel 1.

FIGS. 11A and 11B show neutrophil migration. 1) TLR2, TNF-R1, IL-1RI receptors, and respective ligands, are the upstream pathways related to IL-8 production; 2) Autocrine and paracrine signaling (via Macrophage and RLR pathways) initiate the attraction of chemokine to Neutrophils. 3) Downstream pathways in this diagram are not very clear, and nothing can be inferred.

FIGS. 12A and 12B show the CCL2 imbalances in favor of Th2. 1) Fibroblast, an important type of cell in the stroma, has three DEGs that are upstream receptors: TNF-R1, IL13RA1, IL4R (type II or RA); 2) IL13 and IL4 have no expression, thus TNF-alpha is the only upstream gene to induce CCL2 transcription (DEG at 6 h and 12 h). The TNF-alpha signal can also reach from NFKB inducing IL-6. Both pathways contribute to unbalance in favor of Th2, instead of Th1. 3) NFKB also helps in the transcription of IL-8 and G-CSF, both promoting neutrophil accumulation. 4) The final result of the pathway is inflammation.

FIGS. 13A and 13B show muscle loss: Cachexia. 1) In the upper right field of the inflammatory mechanisms of the pancreatic cancer pathway, it can be seen that the abundance of IL6 (protein) induces cachexia.

FIG. 14 shows 1) Skeletal muscle atrophy in COPD pathway has TNF-alpha as possible upstream. IGFBP4 (DEG) and IGFBP6 can also act as an upstream. MSTN (myostatin) has no expression. The upstream genes in the pathway have low confidence by observing the transcriptional data. 2) But, in middle stream, there are several downregulated genes like a) centered on MAFbx: MYH8 (MyHC) (dw, dw), MYL1 (MELC) (dw, dw), MYL7 (MRLC) (dw, dw); b) centered on MuRF1: MYH7 (beta-MHC) (dw, dw), MYBPC1 (dw, dw), TNNT3 (Beta TnTF), MYH2 (Myosin IIA) (dw, dw), MYL1 (MLC1F) (dw, dw), MYL2 (MLC2) (dw, dw). 3) Negative binding regulation can give rise to cachexia. 4) It has been discovered that SELP (Selectin P) is a possible gene involved in cachexia, SELP is an upregulated DEG in 6 h and 12 h.

FIG. 15 show the SDF1. 1) The downstream myosin genes look like the previous figure (via cachexia). But here, the upstream effector is the well-defined SDF-1, involved in neutrophilic attraction and expression of GCSF.

FIGS. 16A and 16B show the SDF1. 1) G-CSF plays a central role in the "hematopoietic stem cell mobilization" pathway; 2) G-CSF activates neutrophilic degranulation. 3) G-CSF negatively induces SDF-1 (CXCL12, almost one DEG in 6 h and one DEG in 12 h - downregulated) decreasing the inhibition of HSC (hematopoietic stem cells) adhesion to BM (bone marrow) cells. 4) G-CSF is also an upregulated DEG in 6 h and 12 h, and C5aR is upregulated in 6 h.

FIG. 17 shows IL1B, TLR2-IL6, PAIl, IL-8, TREM1.

FIG. 18 shows 16 h - IL1B, TLR2-IL6, IL8, CCL2, beta defensin 2.

FIG. 19 shows a pipeline which consists of two modules: a) quantification and b) DEG/Analysis of pathways. The first one consists of evaluating quality data using fastqc and, subsequently, the quantification is calculated using Subread. The second module consists of the following sub-modules: a) DEGs are calculated using EdgeR; b) the first round of Enrichment Analysis (EA) is performed using String-db and KEGG gmt; c) with the list of enriched KEGG pathways, the first DEG list is improved using Bayesian analysis, resulting in a larger DEG list; d) again, the EA is run, but knows how to use fastGSEA, String-db and Metacore for manual analysis; e) for KEGG, Metacore and Reactome databases, inter-experiments with high pathway modulation (t6 x t0 versus t12 x t0) can be found and the respective genes modulated; f) with these modulated genes, and other specialized pathways selected manually are found in Metacore; and, at last, g) the functionalities and the analysis of the up/down stream pathway are performed.

FIG. 20 show the main proposed pathways to elucidate the transcriptome data. At the top, the main one causes an "Amblyomin-X injection", just below the four proposed ranges: "first hours" (<6 h), "~6 h" (close to 6 h), "]6,12[h" (between 6 h and 12 h), and "~12 h" (close to 12 h). Each blue pathway denotes an enriched pathway calculated using Metacore, KEGG or Reactome. This enrichment analysis was obtained by comparing 6 h x 0 h and 12 h x 0 h.

FIG. 21 shows the expression boxplot of the most important DEGs of the RLR pathway. In the expression of coordinates in the normalized CPM and on the x-axis, three time points 0 h, 6 h and 12 h. The numbers inside the boxplots are related to the samples, all different. It is possible to see the heterogeneous responses and the lack of normality for some expressions.

FIG. 22 shows the validation of RNA-seq results using qRT-PCR. The same RNA used for RNA-seq was used for qRT-PCR. The AACt method was used to calculate changes in gene expression and RPL18 was used as an internal control. Data analysis was performed in three groups (control, 6 h and 12 h) and the data presented were compared in relation to the control. LFC values >1 are representative of positive regulation and LFC <1 are representative of negative regulation. Control group: 4 different tumors; 6 h group: 5 different tumors; 12 h group: 5 different tumors. The data are the mean±SD of the different tumors present in each group.

FIG. 23 shows graphs representing the correlation a) log 2FC (PCR) x log 2FC (RNA-Seq) for 6 h×0 h, adjusted R2=0.800; b) log 2FC (PCR)×log 2FC (RNA-Seq) for 12 h×0 h, adjusted R2=0.815.

FIG. 24 shows the validation of RNA-seq results using qRT-PCR. Bar graphs represent 41 of the 42 selected genes: in RNA-Seq for 6 h, in PCR for 6 h, in RNA-Seq for 12 h, and in PCR for 12 h. A good correlation can be observed between RNA-Seq and qRT-PCR. All experiments were carried out in triplicate and SD and SE were propagated according to the Pfaffl expression equation, with efficiency equal to 2. The height of the bar refers to the average relative expression and the bar error is SEM.

FIGS. 25A and 25B show, respectively the StringDB—HSA—t6×t0 and t12×t0-*Equus* Melanoma -time series bayes KEGG.

DETAILED DESCRIPTION OF THE INVENTION

Figure 11:
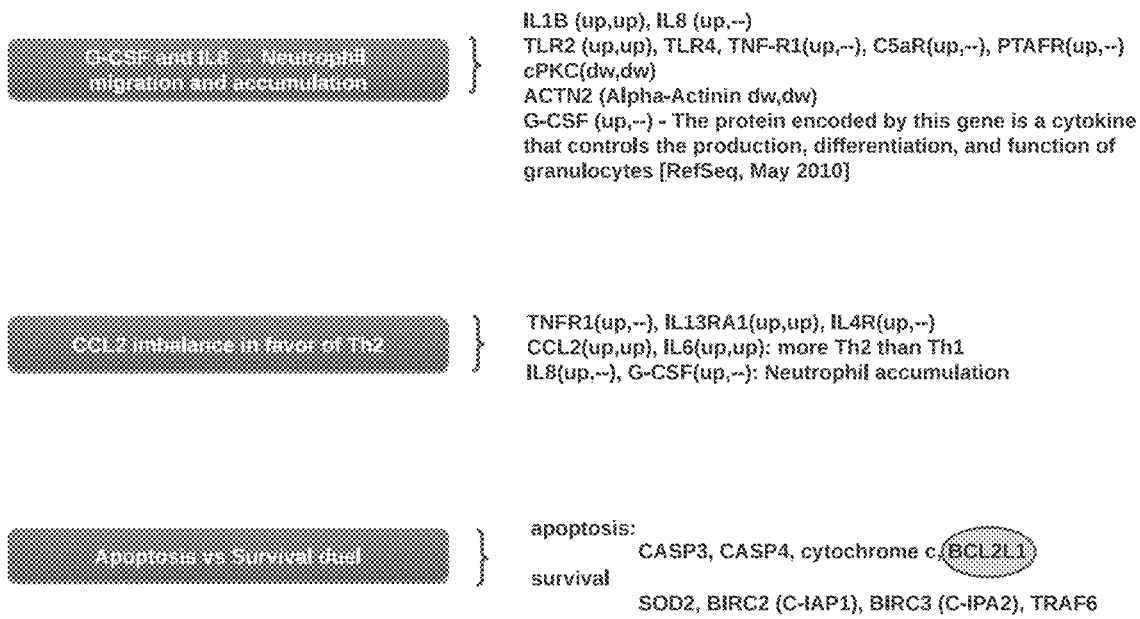
FIG. 11 shows a schematic of the tertiary responses relating Function and DEGs.
Figure 13:
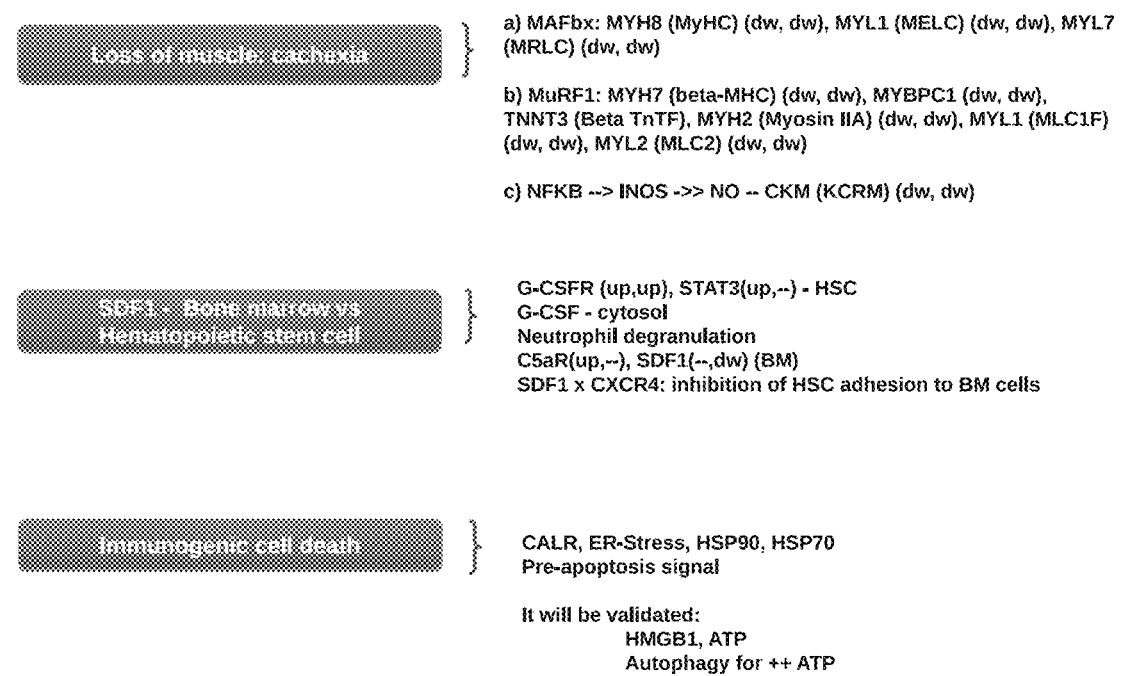
FIG. 13 shows a schematic of the final responses relating Function and DEGs.

The present invention provides for a compound to modulate one or more innate immune pathways selected from RLR, TLR, OAS and/or Oncostatin M.

The present invention also provides for: the use of said compound in the preparation of medicines; a composition and method to modulate said pathways; and a pharmaceutical composition comprising said compound.

The compound of the present invention is a synthetic peptide selected from: Amblyomin-X (Seq ID No. 1); the peptides VCNLPKLAGDE (Seq ID No. 2), GDETCSNKTEI (Seq ID No. 3); IRWYYNGTACEAFI (Seq ID No. 4), KGCGGNDNNFD (Seq ID No. 5), NNFDRVDDCQRLC (Seq ID No. 6), NNFDRVDDSQRLC (Seq ID No. 7), VCNLPKLAGDETCSNKTEIRWYYNGTA (Seq ID No. 8), GTACEAFIFKGCGGNDNNFDRVDDCQRLC (Seq ID No. 9); or combinations thereof.

The invention is also defined by the following clauses:

1) Compound to modulate the RLR, TLR, OAS and/or Oncostatin M pathways characterized in that it is selected from: Amblyomin-X (Seq ID No. 1); VCNLPKLAGDE (Seq ID No. 2), GDETCSNKTEI (Seq ID No. 3); IRWYYNGTACEAFI (Seq ID No. 4), KGCGGNDNNFD (Seq ID No. 5), NNFDRVDDCQRLC (Seq ID No. 6), NNFDRVDDSQRLC (Seq ID No. 7), VCNLPKLAGDETCSNKTEIRWYYNGTA (Seq ID No. 8), GTACEAFIFKGCGGNDNNFDRVDDCQRLC (Seq ID No. 9); or combinations thereof.

2) Pharmaceutical composition which modulates the RLR, TLR, OAS and/or Oncostatin M pathways characterized in that it comprises the compound disclosed in claim 1) and a pharmaceutically acceptable excipient.

3) Use of the compound disclosed in claim 1) for the preparation of a drug to modulate the RLR, TLR, OAS and/or Oncostatin M pathways.

4) Method for in vitro modulation of the RLR, TLR, OAS and/or Oncostatin M pathways, comprising the contact of the compound disclosed in claim 1 with a cell, tissue, or organ.

5) Method of treatment of a disease related to the modulation of RLR, TLR, OAS and/or Oncostatin M pathways characterized in that it comprises the contact of the compound disclosed in claim 1 with a subject.

Example 1. Use of the compound of the invention simultaneously activates different pathways The examples shown here are intended only to exemplify one of the countless ways to carry out the invention, however without limiting the scope thereof.

In this embodiment, the administration of the compound of the invention to mammals provides for the simultaneous modulation of four different canonical innate immune systems. The results of the experiments described in the present invention clearly show the modulation of 1) Toll-like Receptor (TLR) pathways; 2) RIG-like receptor (RLR) pathways; 3) OAS; and 4) Oncostatin M pathways.

TLR, RLR and Oncostatin M are generally related to the production of cytokines and the RLR is also related to the production of interferon. As is well known, the innate immune system is the skin's first immune response against external pathogens. Peripheral skin melanoma cells consist of many different cell types, and many of these cells can respond to external disturbances through inflammatory cytokines and other paracrine molecules. Viral and bacterial infections trigger Pattern Recognition Receptors (PRR), such as TLRs, but after cell invasion they can be recognized by dead-box helicases (DDX), interferon-induced helicases (IFIH) and RNase L genes, such as: DDX58 (RIG-I), DDX60, IFIH1 (MDA5) and OAS (OAS1, 2 or 3), are all present as DEGs. Each of these genes has specialized functions for recognizing DNA or RNA in the cytosol and, right after starting the antiviral response, the pro and anti-inflammatory responses begin.

In this embodiment, the use of the compound of the invention provides initial observable results that are consistent with the first TLR-induced response, increasing the expression levels of many inflammatory cytokines. Therefore, RLR continuously induces the production of IL6, IL8 and IP10 (CXCL10), which are important genes in the inflammatory pathway.

A notable observation in the present invention is that the use of the compound of the invention does not lead to the detectable expression of Interferons. This surprising result is in apparent contradiction with the expected results vis-a-vis the prior art, according to which type 1 interferon (IFN alpha and IFN beta) must be transcribed in one of the branches of the RLR pathway, via IRF7. This did not occur or was not detected in the experiments.

It is also worth mentioning the fact that the use of the compound of the invention did not induce the detectable expression of the NOXA gene (PMAIP1).

The results shown in the present invention support the claim to modulate important pathways. The in vivo administration of the compound of the invention provides enriched signals of effective modulation within 6 h after administration, including Endoplasmic Reticulum stress and cytoskeleton remodeling. Interestingly, ohman et al. described a crosstalk among many RLR proteins and Actin and Tubulin intact proteins close to the mitochondria. In contrast and unexpectedly, the results presented in this patent application show that the administration of the compound of the invention leads to the following DEG modulation: positive regulation of ACTN1 and ACTR3; high negative regulation of ACTA1 and ACTN2; and, with respect to the Tubulin family, on positive regulation of TUBB and TUBB6.

Methods

Melanomas usually are benign tumors, but they can have unpredictable malignancy. In this context, melanoma from horse with dark hair has characteristics that favor greater malignancy when compared to other horses with white hair. Skin tumors in horses are the most common among neoplasms. About two thirds (66%) of the tumors are melanomas and can progress to malignant and metastatic forms. Melanoma is a neoplasm created from melanocytes, and these neoplasms represent 5% to 14% of equine skin neoplasms.

Equine melanoma tumors were used in experiments with the administration of the compound of the invention, for transcriptomic analysis at different points in time. This translational experiment was carried out at Sao Joaquim Farm (SP) and the samples were transported to the Instituto Butantan, in the city of Sao Paulo. The experiment was designed with non-treated control samples at 0 h (PBS) and the treated tumors were excised 6 h and 12 h after the injection of 1 mg of polypeptide per kg of tumor. For each time point, two tumors were removed from three different animals, producing six tumors per time point. All 18 cDNA libraries were prepared following Illumina's TruSeq® RNA Preparation Kit Kits v2 protocol, and then sequenced using HiSeq 1500 Illumina technology, generating 2×100 bp chain-specific paired readings. The raw sequencing readings had the contaminants removed with bowtie2 2.2.5, and then trimmomatic was used for quality control of the sequences, to cut and remove readings with regions of low complexity and enriched with homopolymers, poly-A/T/N tails, low quality adapter strings and bases, with the fastq-mcf 1.04.662 software. The readings were filtered if more than 90% of the readings correspond to regions of homopolymer or of low complexity. Subsequently, cut if the average quality score was less than 25 in a window size equal to 15. After cutting, all readings less than 40 bp were discarded.

RNA extraction and library preparation

Total RNA was isolated from cells grown with Trizol (Ambion, Life Technologies) and purified with a Mini RNAspin kit (GE Healthcare) according to the manufacturer's instructions, with prolonged treatment with DNase I for 1 h.

RNA quality was assessed with an Agilent 2100 Bioanalyzer RNA Pico assay. RNA was quantified using the RibGreen Quant-iT and RNA reagent kit (Invitrogen, Life Technologies). The messenger RNA (mRNA) was isolated and used to prepare the complementary DNA (cDNA) libraries following the instructions of the TruSeq RNA Sample Prep Kit V2 (Illumina, San Diego, Calif.). Briefly, the mRNA was isolated with oligo-dT and purified. Then, the mRNA was fragmented by heating to 94° C. (4 min) in fragmentation buffer. The double-stranded cDNA was synthesized, repaired at the end and tail A. The sequencing adapters were then attached to the cDNA fragments, according to the manufacturer's protocol. The cDNA fragments were enriched after 15 rounds of PCR amplification. The quality control of the library was assessed by size distribution of the cDNA libraries measured using 2100 Bioanalyzer with DNA1000 assay (Agilent Technologies) and a StepOnePlus real-time PCR system from ABI were used to quantify the sample library before sequencing. The cDNA library was sequenced on the Illumina HiSeq 1500 System, in a final flow cell paired with Rapid in a 200 pair strategy of 2-101 bp pairing strategy.

Synthesis of cDNA and qRT-PCR

The levels of gene expression of selected targets observed as differentially expressed in RNA-seq were validated by qRT-PCR. PCR with 40 cycles and 1 pg of the resulting purified total RNA (without reverse transcription), using different primer pairs for the tubulin gene TUBA1C and Histone H3 (multiple copy gene) were previously used to confirm the absence of genomic DNA in all samples. To measure protein-encoding mRNAs, reverse transcription (RT) was performed with SuperScript III according to the manufacturer (Invitrogen) followed by qPCR. For all genes, random transcription initiated by oligo-dT and random was performed using 725 ng of total RNA in 20 pl RT reaction with SuperScript III (Invitrogen), followed by qPCR using 2 pL of the 10-fold diluted RT reaction in 8 pL of qPCR (QuantStudio 3 Real-Time PCR System, Thermo Fisher Scientific). For the assays, the transcription levels were normalized to RPL18 and represented as relative abundance using the delta Ct method. Two controls for the RT step, one without primer (−primer) and one without reverse transcriptase (−RT), were performed, followed by qPCR with the primer pair, in order to confirm the absence of autopriming and genomic RNA. DNA contamination in RT, respectively. The conditions for the qRT-PCR reactions were: 40 cycles of 95° C./15 sec, 60° C./1 min, using the specific primers listed in Table 1.

TABLE 1

Primer sequences used for validating RNA-seq data by qRT-PCR

| Target | Gene_id | Primer | Sequence |
|---|---|---|---|
| ACTN1 | ENSECAG00000019476 | Sense | CCAAGTCATGGCTTCCTTCA |
|  |  | Antisense | ATGCAGTACTCGGCCTGGTC |
| CAD | ENSECAG00000014690 | Sense | CTGCCTGCTCACCCAGTATC |
|  |  | Antisense | CAAATTCCTCCTGCTTGGTG |
| CCL2 | ENSECAG00000023949 | Sense | TGTCCCCAGAAAGCTGTGAT |
|  |  | Antisense | TATCCTGGACCCACTTCTGC |
| CDO1 | ENSECAG00000012826 | Sense | TTGAGGGAAAACCAGTGTGC |
|  |  | Antisense | CAAAGGCATGGCATGTATCA |
| FSCN1 | ENSECAG00000008056 | Sense | ACGCCAGCTGCTACTTTGAC |
|  |  | Antisense | GAGTCCCCTGCTGTTTCCAC |
| HMOX1 | ENSECAG00000001129 | Sense | CTGTTTGAGGAGCTGCAGGA |
|  |  | Antisense | GAGTCTCTGAGGGCGTAGGG |
| HSPA6 | ENSECAG00000004180 | Sense | GGAAGAGGTGGAGAGGATGG |
|  |  | Antisense | GCAAGGAGCTCTTCACATGG |
| IFI35 | ENSECAG00000001598 | Sense | GAGTGGGGAGATCCAGAAGG |
|  |  | Antisense | TGGGCTTCTGGAAGTGAATC |
| IL1RN | ENSECAG00000004312 | Sense | ACTCCAGGAGGAAGCTGT |
|  |  | Antisense | TTGAGCGGATGAAGGTGAAG |
| IRF9 | ENSECAG00000024429 | Sense | TCACAGTGCAGATGGAGCAG |
|  |  | Antisense | GAACAGAGAGGGGAGGAGGA |
| MYLPF | ENSECAG00000017437 | Sense | TCCCATCAACTTCACCGTCT |
|  |  | Antisense | AGGCTCCAGTGATCACATCC |
| OAS2 | ENSECAG00000014422 | Sense | CTCCTGACCCAGATGCAGAG |
|  |  | Antisense | AGAAGATGCCAACACCAACG |

TABLE 1-continued

Primer sequences used for validating RNA-seq data by qRT-PCR

| Target | Gene_id | Primer | Sequence |
|---|---|---|---|
| PER1 | ENSECAG00000013291 | Sense | GATGTGATGGCCTGTGTGG |
|  |  | Antisense | GCCCTAGTCCATCCAGTTCC |
| SLPI | ENSECAG00000016161 | Sense | CCATCTCGAAGCCAGTTGAG |
|  |  | Antisense | CACTGGCCATCTGTCTCACA |
| STAT1 | ENSECAG00000009039 | Sense | GAGAGCGTGCTCTGCTCAAG |
|  |  | Antisense | GGTTCGACCGCATGAAAGTA |
| TLR2 | ENSECAG00000018028 | Sense | GTGATCCCACTGGTGTCTGC |
|  |  | Antisense | AGAGGCGATCTTGTTGTTGG |
| BCL3 | ENSECAG00000013124 | Sense | GAACACCGAGTGCCACGAG |
|  |  | Antisense | CACCATGCTGAGACTGTTGC |
| BIRC3 | ENSECAG00000012229 | Sense | GCAGAAGATGAGATGAGGGAAG |
|  |  | Antisense | CCAGGATTGGAAGCACACAC |
| CTSL | ENSECAG00000007210 | Sense | GTGGTTGGCTATGGCTTTGA |
|  |  | Antisense | AGTGGTTTTCCCGGTCTTTG |
| CXCL6 | ENSECAG00000012742 | Sense | AGAGAACTGCGTTGCATGTG |
|  |  | Antisense | TGGCTACGACTTCCACCTTG |
| DDX58 | ENSECAG00000021989 | Sense | AAGGCATCGACATTGCTCAG |
|  |  | Antisense | TTGCTCTTCCTCTGCCTCTG |
| F12 | ENSECAG00000010619 | Sense | TCCTGAGCTCTGCTCCACTC |
|  |  | Antisense | TCTGCAGTCTCGTCCTCACA |
| FOSL1 | ENSECAG00000023092 | Sense | AACCGGAGGAAGGAACTGAC |
|  |  | Antisense | TCCTTCTGCTTCTGCAGCTC |
| IFIH1 | ENSECAG00000007881 | Sense | TATGCCCTTTCCCAGTGGAT |
|  |  | Antisense | TGTGTCCAGCTCCAATCAGA |
| IFIT1 | ENSECAG00000004433 | Sense | TGGACTGTGAGGAAGGATGG |
|  |  | Antisense | GGGTTTTCTGGGTCCACTTC |
| IL13RA1 | ENSECAG00000019115 | Sense | TCGGTTGTTCCTTTGCTCTG |
|  |  | Antisense | GTGGAGGATCAGGCTTCACA |
| IL1B | ENSECAG00000000168 | Sense | TCTTGTGGGACGAAAGATGG |
|  |  | Antisense | AATTCCACGTTGCCCTTGAT |
| ITGA1 | ENSECAG00000017386 | Sense | GAGTGAAAATGCATCCCTGGT |
|  |  | Antisense | ACTCTGCCTGGTAGCCCATC |
| MYH3 | ENSECAG00000025060 | Sense | TGGTGGACAAACTGCAAGTG |
|  |  | Antisense | CTGCAATATCGGCAGGTTCT |
| PARP9 | ENSECAG00000012331 | Sense | CCAGAGGCTGTTTCAGCAAG |
|  |  | Antisense | GGTCCATACTTTGGGTCGTG |
| PIK3R6 | ENSECAG00000017146 | Sense | TGACAAACACCTTCCGAACC |
|  |  | Antisense | GCAACCTCGAATCTGACGAC |
| RUNX1 | ENSECAG00000003462 | Sense | TCCACTGCCTTTAACCCTCA |
|  |  | Antisense | GATGGGTGTTGCTGGGTGTA |
| SAA1 | ENSECAG00000011404 | Sense | CAGCGATGCCAGAGAGAATG |
|  |  | Antisense | ATTCATTGGCAGCCTGGTC |
| SELP | ENSECAG00000010918 | Sense | ACAGCATGCCAAGAGAGTGG |
|  |  | Antisense | AGGGCTTCCTGGATTGTCAG |
| SOCS3 | ENSECAG00000001249 | Sense | GCCACTTTCTTCACGCTCAG |
|  |  | Antisense | CTTGAGCACGCAGTCGAAG |
| TAT | ENSECAG00000021565 | Sense | GCTGAGCAATCCGTCCACT |
|  |  | Antisense | TACAGGCCTCCAGCATCATC |

TABLE 1-continued

Primer sequences used for validating RNA-seq data by qRT-PCR

| Target | Gene_id | Primer | Sequence |
|---|---|---|---|
| TEAD4 | ENSECAG00000011303 | Sense | CCTGCCCGAGAAGTAGATGA |
|  |  | Antisense | CAAGGTCTCCTGCGTGTCTC |
| THBS1 | ENSECAG00000008923 | Sense | GGCATGACCCTCGTCACATA |
|  |  | Antisense | GGTCCTGAGTCAGCCATGAT |
| TREM1 | ENSECAG00000017436 | Sense | CAGTTCACGTCCGAATGACC |
|  |  | Antisense | TCAGGGTTGCTGAGAATTGG |
| RPL18* | ENSECAG00000021927 | Sense | GAGGTGCCCAAACTGAAGGT |
|  |  | Antisense | CAGCTGGTCAAAGGTGAGGA |

*Reference to the endogenous gene that was used in this analysis.

Protein interactions with the compound of the invention

Purified and lyophilized Amblyomin-X (6 mg) was dissolved in 1 ml of 0.2 M NaHCO$_3$ containing 0.5 M NaCl, pH 8.3. The protein was immobilized on a HP 1 ml column activated by HilrapTM NHS (GE Healthcare Life Sciences) according to the manufacturer's instructions. Thereafter, tissue extract from equine melanoma tumor samples was applied to the HiTrapTM Amblyomin-X affinity column. To eliminate any non-specific protein interactions, the column was washed with 60 ml of 20 mM tris-HCl buffer, pH 8.3. Bounded proteins were eluted with 200 mM glycine containing 0.5 M NaCl, pH 4.0. The eluent was extensively dialyzed with 25 mM ammonium bicarbonate and dried on a vacuum speed evaporator (Thermo Scientific). The dry samples were stored at −80° C. or dissolved in 50 mM ammonium bicarbonate, containing 10 mM CaCl$_2$ for MS/MS analysis. For the identification of proteins, samples of trypsin hydrolysates were analyzed in an LC EASY-nano system (Proxeon Biosystems) coupled online to an ESI-LTQ-OrbitrapVelos mass spectrometer (Thermo Fisher Scientific), which was operated in positive mode of ionization dependent automatic search (DDA) mass scanning of mass spectra digitized by MS. The Peaks Studio 7.5 (Bioinformatics Solutions Inc. Canada) was used for data acquisition, processing, and analysis.

Bioinformatics and Systems Biology

The in-silico analysis of RNA-Seq comprises several quality steps and transcriptomic quantification algorithms that are understood in the present invention as "pipeline". (FIG. 19). The quality check was performed using FastQC3. Hisat214 was used to align readings against the horse's reference genome (*Equus caballus*) (annotation version 89). To map and quantify transcriptions, the feature Counts was used, resulting in a table of genetic IDs versus samples with raw reading counts. Then, differentially expressed genes (DEGs) were calculated using the EdgeR package. Genes with less than one count per million (CPM) were filtered out.

The DEGs were calculated by crossing the sample values of a) 6 h after treatment (6 h)×control (0 h); b) 12 h after treatment (12 h)×control; and also, c) 12 h×6 h. DEGs are defined as an absolute value of log 2 fold change between two groups (LFC)>1 and false discovery rate (FDR)<0.05. All transcripts were mapped using Ensembl Gene ID, and horse gene IDs were mapped to human genetic IDs (reference genome *Homo sapiens* (GRCh38) and annotation (version 89), when orthologs could be found using BioMart, a Bioconductor package (FIG. 19).

The enrichment analyzes were performed using String-db with KEGG as the main database. A second round of DEG assessment improves the DEG list using a Bayesian DEG Improvement Algorithm (BDIA). With the new DEG list, it recalculates Enrichment Analysis using String-db, fGSEA, Enrichr and Metacore using the following databases: KEGG, Reactome, Pfam and GO. A new algorithm called Differential Modulation algorithm between Enriched Pathway Comparisons (DiffMod) was used to search for the most modulated pathway between comparisons of 6 h×0 h and 12 h×0 h. DiffMod is a robust algorithm that finds differences between comparisons, looking for differences in LFC (LFC (casel) - LFC (case)) with a minimal cut, and not just for DEGs in both comparisons.

The translational problem

The genes present in the horse genome have many parallels, and many of them can be mapped in the human genome (orthology), but others do not. Conversely, few genes present in the human genome have parallels, while other genes only existed in the horse's genome. Therefore, about 5.8% of the transcripts were lost (Table 2).

TABLE 2

Gene comparation

| Featured Content | Comparation transcription | | Percentage of transcription | Horse set | Human set | percHsa-Horse set | Validation symbol | Horse percHsa |
|---|---|---|---|---|---|---|---|---|
| 26991 | t6xt0 | 14867 | 55.08 | 14867 | 14004 | 94.2 | 13943 | 93.78 |
| 26991 | t12xt0 | 14867 | 55.08 | 14867 | 14004 | 94.2 | 13943 | 93.78 |

Some cases represent important challenges in the problem of ortholog mapping, with regard to enrichment analysis. Looking at the GFT annotation table, the CCL13 and CCL5 cytokines have the same symbol of the ortholog gene between horse and human, otherwise CCL2 and CCL3 have orthologs CCL7 and CCL18, respectively. This orthology can result in different enrichment analyzes compared to a translational study. Following this reasoning, all genes that have no ortholog have been discarded, regardless of their expressions (readings), and these losses can weaken all enrichment analyzes, as is the case with the ortholog CCL2/CCL7.

Genetic features: biased vs. impartial approaches

At present, at least two ways to predict the functionalities of genes are known: a) the polarization approach, where all genes participate in the search among a certain set of genes, called "Gene Set Enrichment Analysis" (GSEA); and b) the impartial approach, which calculates the correlations between genes in different cases or time points, called "Co-expression Analysis" (AC) between all pairs of genes. In the present invention, both ways, GSEA and CA, were used to better understand the results of transcriptomics. To calculate the GSEA, the following algorithms/software were used to find the functionalities of the genes: a) String-db, fast-GSEA, Enrichr and Metacore. To calculate the CA, both WGCNA and CEMiTool were used. The main idea was to discover a) relationships of the "orchestrated dance of genes" in each module in relation to the enrichment analysis and b) find new genes absent in the enrichment analysis, which are DEGs and participate in corresponding modules.

Enrichment analysis - bias approach

For GSEA String-db, a web application of protein-protein interaction (PPI) network was used, also having a package in R. In addition to validating genes for the species of *Homo sapiens* (in a translational model), it calculates possible protein and interaction scores creates a PPI network. The resulting network properties can be evaluated using the igraph package. The degree of connectivity (k) and the centrality between (g) were calculated. Whenever necessary, String-db clusters the network into sub-modules. String-db uses excessive representation analysis (ORA) against KEGG, GO, Pfam and other databases. The results of String-db+KEGG were presented, using the first 400 most significant DEGs for each comparison. The Gene Set Enrichment Analysis algorithm is a GSEA method developed by Subramanian at the Broad Institute in 2005. The fast GSEA was chosen instead of the java solution because it is a much faster algorithm. The fGSEA calculates the enriched pathways using Reactome, KEGG and other databases offered by the Broad Institute. Enrichr was used to evaluate the enrichment analysis of drugs and diseases, using the LINCS L1000 database.

Finally, the last analysis was carried out using Metacore (version 6.34 build 69200/2018): GSEA, also called Pathway Maps, Process Network Analysis (network enrichment analysis) and Specialized Network Analysis (SNA). The first two methods use all DEGs sent and calculate the enriched pathways and the enriched networks, respectively, for each Comparison (6 h×0 h and 12 h×0 h). The cut-off point of p-value was 0.05 and all up and down genes were used. Intersection analysis between two experiments was not used (compare experiments), as it is believed that DiffMod is a more sensitive algorithm. The third approach, SNA, uses prior knowledge of the network and the user must define a "small" gene set (recommended from 6 to 20 genes) that is believed to represent a determined biological function, previously enriched by any algorithm, validated in experiments, published in reviews or meta-analysis with high impact scores. Transferring these genes to the network enrichment algorithm (bild network, the most general way to calculate the network enrichment analysis in Metacore), the result is a set of specialized networks with well-defined biological/biochemical functions called "specialized network" (SN). The first two methods result in perceptions of biological functionality, and the last (SN) is intended to enrich branches (sub-pathways) belonging to one or multiple pathways. It is noteworthy that some enriched branches can be part of different pathways, believing that this is the way that nature found to evolve and adapt to the environment, a modular reuse of a specialized set of proteins.

Co-expression network analysis - the impartial approach

WGCNA and CEMiTool were used to analyze the co-expression modules. Co-expression analysis was performed with CEMiTool, with a minimum of 20 genes per module and a set of cutreeDynamic modules at 0.75.

This resulted in 28 co-expressed gene modules, called M1-M28, mainly related to the PPAR signaling pathway/Lipid and lipoproteins metabolism/Rho-GTPases signaling/Epidermal development (M1), JAK-STAT signaling pathway/cytokine signaling in the immune system/Inflammatory response (M2), TCA cycle/Lysosome organization/Cillium (M3), Developmental pigmentation (M4), Peroxisome/Lipid and lipoproteins metabolism/Fatty acid metabolic process (M6), Inflammatory response (M7), Muscle contraction. Muscular system process (M9, M10), Positive regulation of locomotion/Body morphogenesis/Regulation of the response to wound healing/Response to oxygen levels (M11), Cytokine signaling in the immune system/response to the virus (M12), Membrane extrinsic component (M13) Cytoskeleton of intermediate filaments (M14), Natural killer cell-mediated cytotoxicity/Cell surface interactions in the vascular wall/Positive regulation of Natural Killer-mediated immunity (M15), cell adhesion molecules/Angiogenesis (M18), Lysosome/Glycosphingolipidic metabolism (M20), RIG-I Receptor signaling pathway/Cytokine signaling in the immune system/Virus defense response (M22), Part of axoneme (M23), Binding to immunoglobulin receptors (M25), neurotransmitter cycle release/Regulation of neurotransmitter levels (M26), Protein lipid complex (M27).

Notably, the genes in M12 showed an increased pattern of expressions at 6 h compared to 0 h and then even higher at 12 h, representing some of those DEGs found to be upregulated in the comparison of 12 h×0 h. Furthermore, M10 showed genes with a higher expression pattern at 0 h, then an abrupt decrease in expression at 6 h and 12 h, representing some of the DEGs found to be negatively regulated in 06 h×0 h and 12 h×0 h comparations.

Most of the DEGs were classified as M9, M10, Mll or M12.

06 h×0 h: M1 (AMZ1, FAM69B, FOXO6, CLEC4G, EMR3, BCMO1, CHP2, HOXB5, ANKRD13D), M2 (CXCL6, ADAMTS8, AKR1C3, FCAR, FOSL1, FPR2, F12, ADAMDEC1, ADAMTS9, CAMP, CCR7, BATF3, CXCR2, HRH2, FCN2, CCL7, B4GALNT4, CSF3, ADAMTS5, HS6ST1, HCAR2, DUSP2, BASP1, ACKR4, CFB, CXCL1, CASP3, CKAP4, AEN, BCL3, GYG1, FSCN1, ADAMTS1, ETV6, DDX58, CCDC86, ANKRD33, CSF2RB, DDX56, DDX21, CTPS1, EPSTI1, COTL1, HMOX1, EAF1, GRWD1, GPATCH4, BIRC3, AGO2, HN1L, FAM203A, CHCHD4, ARG2, GTPBP4, EDNRB, AMPD2, CASP4, DDX10, G3BP1, COX10, DDX54, ABCF2, CAD, DUS3L, GNL3, DKC1, ACTN1, GEMIN5, DDX27, EBNA1BP2), M3 (ALDH1A3, GXYLT2, CD163, GPM6B, CYBRD1, C5AR1, CPNE8, ADAM9), M4 (ARHGAP36, HSPA6, DGKG, C1orf110), M5 (CACNA1D, HEST, ACSM4, CAND2), M6 (CLGN, DDO, CNDP1, FOXN4, COLCA2, AQP7, FBXO17, COX412, CRYM, EFCAB4A), M7 (EAF2, CD300A, CD163L1, CAPSL, CTSL), M9 (CSRP3, ACTA1, CASQ1, COX6A2, ACTN2, ABRA, ANKRD1, AMPD1, C1orf170, ANGPTL1, ASB10, CABP2, CTXN3, CLDN15, FITM1, DDIT4L, GLI1, CLEC3B, DHRS7C, ABCG2, FAM162B, GLT8D2, CD34, ANKRD2, CTSW), M10 (CKM, CA3, APOBEC2, CMYA5, CACNA1S, CAV3, DUSP27, ENO3, DUSP13, C10orf71, CDH15, GADL1, FIBIN, CLEC2L, CDO1, ATP2A1, C1QTNF7, CCDC114, ABLIM3, CD300LG, CD248, DBP, FAM13C, C1QTNF2, ABCB1, EMCN, CYP21A2, ACE, FXYD1, ARHGEF25, HIGD1B, ANKRD23, C10orf10, EXD3), Mll (ADAMTS4, CRISPLD2, CYP7B1, CD38, ARHGAP26, ADAM19, EIF5A2, CGA, ARSJ, HOXC11, CHSY1, EMP1, HAS2, ANGPT2, CDC42SE2, FGF7, DOHH, GDA, HSPA5, CD46, DPH5, ANKRD42, CYCS, FAM111B, ABCC3, FNDC3B, CDH3, ARID5B, HIPK2, CALR, DDX18, CSRNP1, CLPB), M12 (CSF3R, EIF2AK2, AVL9), M13 (FOXS1, AARS2), M14 (EFHD1), M15 (CD300LF, CTHRC1), M16 (FAM115C), M18 (DYSF), M19 (CHRM1), M25 (ALPL, HSP90B1).

12 h×0 h: M1 (FGG, BCMO1), M2 (ADAMTS8, FCAR, FOSL1, F12, DAW1, ADAMTS9, CAMP, CCR7, CXCR2, HRH2, FCN2, CCL7, B4GALNT4, ADAMTS5, HCAR2, CATSPER3, HSD11B1, GBP3, BCL3, GYG1, FSCN1, ETV6, DDX58, CCDC86, ASPN, DDX56, EPSTI1, COTL1, COX10, DDX54, DDX51, GNL3, CHAF1B), M4 (HSPA6, FRZB), M5 (CACNA1D, FGL1, FBXO27), M6 (FBXO17), M7 (EAF2, CD300A, CD163L1, ARNTL2, CTSL, HELLS, DCTPP1, ENTPD4, CARHSP1), M9 (CSRP3, ACTA1, CASQ1, COX6A2, ACTN2, ABRA, ANKRD1, DUSP26, ANGPTL1, ASB10, C1QL1, DDIT4L, CLEC3B, DHRS7C, ABCA8, FAM162B, GLT8D2, CXCL12), M10 (CKM, CA3, APOBEC2, CMYA5, CACNA1S, CAV3, DUSP27, ENO3, FIBIN, CDO1, ATP2A1, C1QTNF7, DBP, C1QTNF2, EMCN, EPHX1, GSTM4), Mll (ADAMTS4, DPH5), M12 (CSF3R, APOBEC3A, C3, EIF2AK2, CLEC4E, GBP2, HK3, DHX58, HERC5, HERC6, AVL9), M16 (FAM115C, CDC6), M22 (CXCL10, DDX60).

Example 2. Method to Improve the DEG List

DEGs are often defined as genes with abs (CFL)>(absolute change in the log 2 order) and FDR <0.05. Surely, one can change these parameters and even maintain different values according to some knowledge, results, and future validations. But the problem arises when the enriched pathways are calculated. An increase or decrease of a few dozen genes can alter the entire enrichment analysis. To solve this problem, a new algorithm is proposed that calculates the distribution around the edge of DEGs and non-DEGs, according to a list of genes ordered by FDR.

The "Bayesian DEG Improvement Algorithm" (BDIA) was implemented to increase the detection of possible significant genes. A Bayesian algorithm was implemented that takes ORA as a function probability for each enriched pathway, and as a priori distribution that calculated with the probabilities of gene expressions (normalized CPM) sampled near the lower edge of DEG and the non-DEG edge. This approach results in an a posteriori distribution, for each pathway, which could be examined, and the new significant genes merged into the DEG list. To validate the present algorithm, the mRNA expression of some of the new DEGs included, as well as some of the DEGs, was measured with qRT-PCR.

There are still problems with DEGS

Most experiments are based on perturbation versus comparisons of control or evolution of time series, and generally the number of repetitions is low (between 2 to 5). This experiment is a time series experiment with 6 samples, 6 samples and 4 samples for control, 6 h and 12 h respectively. An important result of the tumor treatment transcriptome is the heterogeneity of the expression of many genes in a given case, easily observed in a box plot where the median is removed from the mean value. For example, the e-selectin (SELE) gene appears to be an important gene in in silico analysis. The SELE expression is not normally distributed, it is a DEG at 6 h×0 h and not at 12 h×0 h. At 12 o'clock there are only 4 samples (2 were discarded) decreasing the statistical power between comparisons. If you compare the LFC SELE (6 h×0 h)=2.33 with the LFC (12 h×0 h)=1.78, it seems that both are DEGs, but when calculating FDR (6 h×0 h)=0.02 and FDR (12 h×0 h)=0.25. Reviewing the original data, their averages were 1.37, 7.15, 4.85 (CPM) and medians were 1.44, 4.56, 5.63 (CPM), for 0 h, 6 h and 12 h, respectively. As can be seen, it is not trivial to calculate the SELE differential modulation. A layman would infer that the SELE is a DEG upregulated at 6 h, and not at 12 h, but it can be a mistake. The low number of samples, low expression and non-normal distributed data can be misleading in the analysis. It is best to manually include these genes as DEGs and validate with qRT-PCR, whenever they are important and related to the pathways of interest.

How to classify enriched pathways

Given the dozens or hundreds of enriched pathways, the person skilled in the art must decide which are the most important pathways, using the FDR as a parameter. The "Differential Modulation between Enriched Pathway Comparisons" (DiffMod) is a punctuation-based algorithm. The main idea is to compare two conditions of any enriched pathway, in the case 6 h×0 h versus 12 h×0 h.

Usually, "semantically interesting concepts" are sought, among the list of enriched pathways, which represents a known phenomenon related to the experiment. In fact, this "supervised" approach is good if the person skilled in the art is an experienced expert, but the interest of the present invention is in automated solutions that look for disturbed genes in each pathway and how the expression varies for each comparison. The DiffMod classifies all the pathways of the most positive disturbed pathways, proportional to the sum of the CFL for case 1, minus the sum of the CFL for case 2, through pathways with zero classification (similar sum of CFL between cases), up to the most negative disturbed pathways. This classification is somewhat a degree of disturbance, it is a good parameter that uses all differentially modulated genes in each pathway to calculate its classification. Therefore, a gene that has an LFC (case1) of approximately 0.9 and an LFC (case 2) of approximately -0.9 has almost the same difference as two DEGs with an LFC close to 1. and more, this gene appears to be a DEG in both cases, but if your values were LFC (case 1) of approximately 1.2 and LFC (case 2) of approximately -0.8, the difference is still equal to 2, but in many state of the art algorithms it is not a DEG in the case 2.

Results EdgeR— DEGs

FeatureCounts exported a table with 269,991 transcriptions, with 18 samples as columns and horse set IDs as rows. This was the entrance to the EdgeR. Low expression genes, i.e., CPM <1, were filtered out. Also, 2 samples at 12 h with low library size were removed. 14,867 valid cDNA transcripts were found, but only 14,414 were genes encoding proteins, according to the GTF biotypes (Figures I.A and 1B). There were 14,004 protein coding transcripts valid for horses. Using BioMart, 13,138 genes encoding symbols for horses and 13,943 genes with symbols for humans were found. Supposing that more genetic symbols were found for humans, due to the fact that their genome is better studied than the *Equus caballus* genome (horse), EdgeR calculated the normalized expression table in "counts per million" (CPM) and this table is the basis for all fold change calculations. Differentially expressed genes (DEGs) were defined as abs (CFL)>1 and FDR <0.05, and only two comparisons are presented and discussed, "6 h×control" (called 6 h×0 h) and "12 h×control" (called 12 h×0 h) (Table 3). Although the experiment is a time series experiment, it was not possible to find DEGs comparing 12 h×6 h, which means that the gene expressions between these two time points are somewhat similar. For horse transcripts, Edger calculated 580 from 6 h×0 h and 276d from 12 h×0 h, and those who had human orthologs were 546 and 259, for 6 h×0 h and 12 h×0 h, respectively. BDIA improved the human DEG list to 626 and 266 DEG, for 6 h×0 h and 12 h×0 h respectively (Table 3).

TABLE 3

Comparison of genes and transcripts.

| Comparation | Transcriptions | # horse degs | # human degs | $ degs (bayes) |
|---|---|---|---|---|
| t6xt0 | 14867 | 580 | 546 | 626 |
| t12xt0 | 14867 | 276 | 259 | 266 |
| t12xt6 | 14867 | 0 | 0 | 0 |

Example 3. In silico network and pathways analysis

KEGG enriched pathways were calculated using String-db, Reactome and Metacore. To calculate the gene enrichment analysis for KEGG, fGSEA and also String-db were used. Uploading DEGs to Reactome, 218 out of 626 DEGs were not found. Uploading DEGs to the Metacore website, 1 of 266 DEGs was not found. String-db enrichment pathways were automatically calculated via R (pipeline), and up to 400 DEGs could be uploaded, a limitation of String-db. For 6 h×0 h 400 DEGs were sent and 395 were acknowledged. The expected number of interactions (random network) was 2996, however, 4383 were found, validating the network with a p-value equal to 0. For 12 h×0 h, 266 DEGs were loaded, and 265 were recognized. The expected number of interactions was 1572, but 2775 were found, validating the network with a p-value equal to 0. fGSEA was used to calculate GSEG KEGG resulting in some enriched pathways, perhaps because the Kolmogorov-Smirnov statistic is very rigorous. Using String-db, 93 and 63 enriched pathways were found to 6 h×0 h and 12 h×0 h, respectively. Interestingly, with 266 DEGs 63 pathways could be enriched, that is, many genes had their expression decreased, but those that are DEGs were very significant. Reactome did not enrich many pathways in both cases, it is assumed that the high number of genes not found, and the detailed pathways contributed to this bias. 226 pathways enriched with Metacore (or for 6 h×0 h, or for 12 h×0 h, or for both). However, few pathways are slightly repeated, e.g., some diseases have similar enriched genes.

TABLE 4

Number of enriched pathways according to String- db/KEGG, Reactome and Metacore. All with fdr < 0.05, Reactome only with fdr < 0.1.

| Cases | stringdb/kegg | reactome (fdr < .1) | metacore |
|---|---|---|---|
| t6xt0 | 93 | 10 | 226 |
| t12xt0 | 63 | 10 | 226 |

As Metacore has a well-curated database and well-explained pathways and networks, it was decided to continue the analysis with this database only. Furthermore, the lack of standards in pathways names is an obstacle to comparing two more databases.

Hubs

The String-db network was built using DEGs and the connectivity index (k) and the centrality between regions were calculated (g). For 6 h×0 h 77 hubs with k between 40 and 113 were calculated, such as: IL6, ISG15, HSPA5, ACTA1, HSPA8, OAS2, IL1B, IL8, HSPD1, ENO3, CAD, HSP90B1, CASP3, MYH6, ATP2A1, HSPA6, HMOX1, HYOU1, PLK1, MYH7, LYN, GTPBP4, CD34, PRKCQ, GL1, IFIT1, MYH1, CXCL1, MYH3 and PYGM. There are 104 G with g between 300 and 4870, such as: IL6, ACTA1, ISG15, HSPA5, CASP3, HSPD1, IL8, PLK1, LYN and CAD. For 12 h×0 h 48 hubs with k between 40 and 86 were calculated, such as: ISG15, OAST, OASL, ACTA1, OAS2, OAS3, STAT1, MX1, TLR2, ENO3, IL1B, TTN, ATP2A1, MYH7, IFIT1, TIMP1, TNNC2, IFIT3, PGAM2, MYH8, MYH1, MYH3, PYGM, TNNC1, TCAP, RYR1, ISG20 and IFIH1. There are 52 G with g between 300 and 1532, such as: IL1B, TLR2, STAT1, ACTA1, MX1, ISG15, TIMP1, ENO3, OAS1, KRT16, OASL, RERGL, HSPA6, SOD2, OAS2, PYGM, RYR1, OAS3, TTN, EIF2AK2 and SOCS3 (tables 5a and 5b). Note that, in addition to the decreased expression of many genes, the hub and central centrality and intersection genes decrease by 12 h compared to 6 h.

TABLE 5A

Genes and interlacement.

| Gene | k | Interlacement |
|---|---|---|
| IL6 | 113 | 48.693.848.771 |
| ACTA1 | 97 | 31.752.774.712 |
| ISG15 | 103 | 26.255.407.840 |
| HSPA5 | 100 | 22.097.825.286 |
| CASP3 | 72 | 21.546.681.535 |
| HSPD1 | 81 | 20.971.550.063 |
| IL8 | 82 | 20.264.511.335 |
| PLK1 | 63 | 20.231.312.509 |
| LYN | 61 | 20.168.186.254 |
| CAD | 78 | 18.928.862.505 |
| HSP90B1 | 73 | 18.445.550.197 |
| OAS2 | 92 | 18.176.820.983 |
| IL1B | 84 | 18.134.276.065 |
| HSPA8 | 95 | 18.019.261.950 |
| ENO3 | 79 | 16.754.867.610 |
| CD34 | 58 | 16.421.769.561 |
| GLI1 | 56 | 15.875.923.841 |
| MYH6 | 71 | 13.167.305.759 |
| HAS2 | 43 | 12.367.802.632 |
| PI3 | 48 | 12.293.541.556 |
| PDE4B | 29 | 12.254.016.846 |
| HMOX1 | 65 | 11.632.682.488 |
| GTPBP4 | 60 | 10.604.348.657 |
| MYO15A | 34 | 10.443.273.150 |
| CALR | 41 | 9.997.278.013 |
| IFIT1 | 55 | 9.816.965.651 |

TABLE 5A-continued

Genes and interlacement.

| Gene | k | Interlacement |
|---|---|---|
| ATP2A1 | 70 | 9.603.523.025 |
| ANGPT2 | 34 | 9.252.109.404 |
| RAB8B | 21 | 8.906.038.249 |
| PYGM | 54 | 8.715.712.868 |
| MYH1 | 55 | 8.468.897.306 |
| PLEK | 46 | 8.275.273.434 |
| ANXA1 | 36 | 8.106.541.645 |
| HYOU1 | 64 | 7.929.556.364 |
| DDX10 | 47 | 7.615.668.305 |
| IARS | 52 | 7.578.203.870 |
| PRKCQ | 57 | 7.423.775.948 |
| KCNJ11 | 35 | 7.400.261.899 |
| CXCL1 | 55 | 7.248.110.023 |
| ISL1 | 39 | 6.954.452.003 |
| MSX1 | 32 | 6.579.608.285 |
| LDHA | 51 | 6.547.417.006 |
| ANKRD1 | 47 | 6.177.621.316 |
| MYF6 | 49 | 6.163.304.911 |
| PDGFRA | 49 | 5.982.379.223 |
| FOSL1 | 47 | 5.584.776.460 |
| CYCS | 40 | 5.418.732.207 |
| PPP1R3A | 22 | 5.402.045.275 |
| ETV6 | 29 | 5.399.401.580 |
| MMP3 | 47 | 5.300.955.498 |
| ABCC3 | 30 | 5.108.604.924 |
| CKM | 53 | 5.091.190.222 |
| HSPA6 | 66 | 5.029.709.467 |
| FGF7 | 37 | 5.020.307.324 |
| MYH8 | 51 | 5.018.520.126 |
| ACE | 46 | 5.010.287.544 |
| MYLK2 | 43 | 4.940.858.761 |
| EIF5A2 | 39 | 4.920.842.096 |
| MYL2 | 53 | 4.831.066.199 |
| MYLPF | 54 | 4.793.232.046 |
| HIPK2 | 17 | 4.743.935.318 |
| ALDH1A3 | 32 | 4.656.674.512 |
| PGAM2 | 52 | 4.368.514.216 |
| DUSP2 | 33 | 4.231.882.383 |
| ABCG2 | 32 | 4.227.338.135 |
| IFIT3 | 50 | 4.221.774.032 |
| LMOD2 | 25 | 4.203.782.355 |
| MTHFD1L | 50 | 4.186.612.215 |
| DDX58 | 33 | 4.182.886.439 |
| ITPKA | 8 | 4.170.677.295 |
| KRT81 | 7 | 4.158.801.678 |
| CSRNP1 | 12 | 4.157.746.142 |
| MYL3 | 50 | 4.122.701.240 |
| AMPD1 | 39 | 4.117.594.163 |
| MYH7 | 62 | 4.102.711.471 |
| BCL3 | 41 | 4.058.966.150 |
| PRR16 | 6 | 4.051.848.451 |
| OSMR | 12 | 3.987.332.287 |
| PIK3AP1 | 9 | 3.963.643.939 |
| DDX21 | 49 | 3.913.796.487 |
| EIF2C2 | 32 | 3.887.181.894 |
| NTNG1 | 4 | 3.877.451.712 |
| NOLC1 | 38 | 3.856.884.770 |
| PLSCR4 | 3 | 3.806.258.733 |
| HYI | 6 | 3.772.242.907 |
| BIRC3 | 39 | 3.689.547.040 |
| ABCB1 | 44 | 3.669.851.450 |
| NAT10 | 44 | 3.665.786.542 |
| CXCL6 | 20 | 3.616.947.103 |
| CAMP | 23 | 3.594.019.018 |
| ACTN1 | 42 | 3.536.408.721 |
| NEB | 48 | 3.475.009.556 |
| AEN | 44 | 3.450.024.349 |
| MYL1 | 54 | 3.437.461.953 |
| CSF3 | 42 | 3.360.431.117 |
| MRTO4 | 49 | 3.328.359.957 |
| CLPB | 40 | 3.313.814.628 |
| FSCN1 | 30 | 3.302.254.263 |
| ANKRD23 | 48 | 3.261.527.351 |
| ACTN2 | 53 | 3.233.914.803 |
| CABP2 | 36 | 3.165.530.706 |
| CAPSL | 24 | 3.088.855.707 |
| MYH3 | 55 | 3.061.910.359 |
| IFIT5 | 44 | 3.032.463.756 |
| BATF3 | 27 | 2.967.058.940 |
| CAV3 | 38 | 2.957.771.904 |
| MAN1A1 | 10 | 2.934.120.895 |
| CDH15 | 10 | 2.918.451.279 |
| ANKRD2 | 45 | 2.890.934.770 |
| DDX18 | 45 | 2.811.459.934 |
| CRISPLD2 | 12 | 2.804.043.722 |
| MYO18B | 34 | 2.787.475.039 |
| CCL7 | 25 | 2.737.000.462 |
| IRG1 | 17 | 2.671.849.145 |
| PLN | 36 | 2.643.279.006 |
| ADAMTS1 | 27 | 2.596.220.614 |
| CLGN | 13 | 2.532.552.420 |
| EIF2AK2 | 31 | 2.498.499.702 |
| LDB3 | 45 | 2.487.860.008 |
| MYH2 | 48 | 2.410.654.559 |
| CLEC3B | 22 | 2.358.573.894 |
| ITPR1 | 29 | 2.342.125.285 |
| CCR7 | 41 | 2.339.143.809 |
| CFB | 16 | 2.322.940.981 |
| CMYA5 | 20 | 2.318.516.457 |
| ABRA | 21 | 2.269.106.079 |
| GNL3 | 41 | 2.249.048.074 |
| IDH3A | 36 | 2.186.141.872 |
| IFI35 | 11 | 2.153.032.879 |
| MMP8 | 32 | 2.138.543.775 |
| PLAUR | 25 | 2.134.899.659 |
| DUSP13 | 26 | 2.123.080.711 |
| MEOX2 | 8 | 2.096.699.653 |
| NFIL3 | 18 | 2.080.618.331 |
| EPSTI1 | 8 | 2.080.069.525 |
| NMNAT3 | 16 | 2.073.867.347 |
| AKR1C3 | 19 | 2.024.462.836 |
| ADAMTS4 | 18 | 1.987.875.534 |
| OSBPL6 | 13 | 1.980.566.348 |
| AARS2 | 24 | 1.968.044.501 |
| GYG1 | 8 | 1.952.665.829 |
| DKC1 | 46 | 1.938.095.026 |
| CACNA1S | 36 | 1.924.955.956 |
| EDNRB | 30 | 1.868.631.018 |
| IL6ST | 24 | 1.862.628.000 |
| GDPD3 | 15 | 1.853.116.486 |
| CDO1 | 9 | 1.840.250.378 |
| LDLR | 33 | 1.813.363.997 |
| EBNA1BP2 | 33 | 1.806.860.217 |
| NFIB | 6 | 1.717.637.066 |
| DUSP27 | 23 | 1.671.230.298 |
| LMNB1 | 25 | 1.643.138.360 |
| GPM6B | 7 | 1.637.825.097 |
| NLRP12 | 21 | 1.598.160.025 |
| CTPS1 | 45 | 1.537.914.588 |
| M6PR | 16 | 1.506.676.405 |
| COX6A2 | 34 | 1.500.181.331 |
| CASQ1 | 43 | 1.496.908.290 |
| MYOZ1 | 48 | 1.496.588.695 |
| CTSL1 | 27 | 1.493.065.657 |
| FXYD1 | 6 | 1.491.198.376 |
| NDRG1 | 15 | 1.455.545.372 |
| CYP7B1 | 11 | 1.412.417.198 |
| C10orf10 | 11 | 1.402.985.310 |
| CHRM1 | 19 | 1.397.763.610 |
| ALPL | 26 | 1.397.283.042 |
| EMP1 | 10 | 1.389.610.596 |
| CXCR2 | 34 | 1.387.283.264 |
| HS6ST1 | 9 | 1.385.369.607 |
| FCN2 | 5 | 1.363.901.901 |
| IL13RA1 | 16 | 1.347.887.867 |
| PTAFR | 21 | 1.338.852.067 |
| PPP1R27 | 28 | 1.337.906.643 |
| DUS3L | 22 | 1.327.156.400 |
| HOXC11 | 6 | 1.326.830.906 |
| MYOM1 | 35 | 1.324.501.748 |
| AQP7 | 25 | 1.274.160.580 |
| CNDP1 | 18 | 1.272.542.399 |

TABLE 5A-continued

Genes and interlacement.

| Gene | k | Interlacement |
|---|---|---|
| PRPS2 | 39 | 1.249.386.880 |
| DPH5 | 24 | 1.239.811.454 |
| MSC | 5 | 1.141.899.073 |
| NELL2 | 5 | 1.137.183.111 |
| ADAM19 | 11 | 1.119.492.832 |
| NELL1 | 4 | 1.098.962.936 |
| CD38 | 24 | 1.094.536.095 |
| DDX54 | 27 | 1.091.744.688 |
| PHLDA1 | 12 | 1.049.929.482 |
| EFHD1 | 8 | 1.018.621.488 |
| FAM115C | 8 | 982.902.698 |
| OSGEPL1 | 10 | 981.362.003 |
| PRPS1 | 36 | 937.273.078 |
| RAB44 | 14 | 912.358.584 |
| KANK3 | 8 | 900.497.523 |
| MMP25 | 16 | 892.174.796 |
| MYBPC1 | 32 | 882.704.996 |
| IL4R | 23 | 878.405.736 |
| AMPD2 | 16 | 849.990.178 |
| PENK | 18 | 849.114.032 |
| C5AR1 | 21 | 846.921.262 |
| MTHFD2 | 31 | 839.029.836 |
| G3BP1 | 18 | 836.634.674 |
| LOXL1 | 8 | 836.551.518 |
| IL1R1 | 26 | 834.392.470 |
| CSF2RB | 8 | 825.709.932 |
| ADAMTS9 | 11 | 807.425.436 |
| NLRC4 | 16 | 798.435.691 |
| NPHS1 | 18 | 784.541.330 |
| GRWD1 | 37 | 782.686.824 |
| DDX27 | 39 | 782.591.870 |
| ADAMTS8 | 8 | 767.122.112 |
| ASB10 | 26 | 764.297.886 |
| MMP11 | 18 | 741.807.298 |
| PPA1 | 27 | 737.077.150 |
| ABCF2 | 31 | 736.671.233 |
| NRAP | 29 | 733.340.542 |
| HOXB5 | 7 | 730.513.161 |
| IGSF6 | 6 | 720.372.307 |
| PTGES | 16 | 716.287.744 |
| ARHGAP26 | 6 | 709.014.661 |
| DOHH | 30 | 692.973.747 |
| ANKRD42 | 24 | 690.417.481 |
| COTL1 | 9 | 657.918.551 |
| CSRP3 | 36 | 652.738.609 |
| PNO1 | 27 | 646.820.543 |
| LINGO1 | 22 | 628.730.439 |
| PTX3 | 8 | 596.400.671 |
| CA3 | 13 | 578.635.755 |
| LRRC17 | 20 | 551.249.414 |
| LYAR | 28 | 546.941.514 |
| FPR2 | 20 | 539.495.040 |
| CACNA1D | 18 | 526.005.469 |
| MYOT | 33 | 525.875.030 |
| CD300LF | 4 | 525.835.446 |
| MYBPH | 31 | 516.075.781 |
| GXYLT2 | 5 | 515.746.783 |
| FOXS1 | 11 | 510.281.997 |
| MRGPRF | 7 | 502.528.947 |
| IL1RN | 25 | 495.230.391 |
| KPNB1 | 15 | 493.967.446 |
| BCMO1 | 3 | 488.913.401 |
| PDSS1 | 17 | 478.291.086 |
| PITRM1 | 10 | 477.977.461 |
| ITGA1 | 15 | 473.402.930 |
| DYSF | 23 | 469.698.126 |
| OLR1 | 19 | 468.389.372 |
| MOB1A | 12 | 456.530.210 |
| EAF2 | 6 | 443.073.843 |
| LMOD3 | 17 | 440.772.129 |
| PROCR | 3 | 440.709.411 |
| NR1D1 | 9 | 436.236.996 |
| MANF | 12 | 435.682.592 |
| MYOZ2 | 35 | 430.226.573 |
| PIWIL1 | 12 | 421.332.736 |
| MAFF | 12 | 418.510.979 |
| COX10 | 20 | 416.536.477 |
| MAL | 5 | 370.341.092 |
| CD300A | 4 | 370.278.545 |
| ACSM4 | 19 | 367.329.604 |
| MYOM2 | 34 | 363.225.940 |
| C1QTNF2 | 6 | 356.350.918 |
| CDAN1 | 12 | 353.975.282 |
| PAEP | 5 | 349.577.136 |
| PTP4A1 | 7 | 346.342.297 |
| CHSY1 | 4 | 335.926.045 |
| MEIS3 | 7 | 332.012.989 |
| LRP6 | 13 | 319.634.080 |
| CASP4 | 13 | 293.081.051 |
| ARG2 | 14 | 285.967.435 |
| ABLIM3 | 5 | 280.466.613 |
| DHRS7C | 14 | 276.975.354 |
| FAM203A | 25 | 275.740.139 |
| EMR3 | 3 | 275.197.483 |
| LOXL3 | 4 | 273.724.845 |
| ANKRD13D | 2 | 267.416.323 |
| B4GALNT4 | 4 | 261.342.125 |
| GLT8D2 | 6 | 259.258.773 |
| MYOM3 | 11 | 241.006.133 |
| CHP2 | 21 | 240.433.592 |
| NARS | 17 | 235.795.231 |
| CYBRD1 | 6 | 228.150.315 |
| P2RY13 | 13 | 220.548.448 |
| F12 | 10 | 207.390.969 |
| HIGD1B | 2 | 201.588.433 |
| IGSF10 | 12 | 192.786.822 |
| KLKB1 | 10 | 185.658.155 |
| MFSD3 | 14 | 179.246.336 |
| DDX56 | 28 | 177.491.900 |
| ADAM9 | 11 | 174.353.934 |
| MIDN | 2 | 155.918.027 |
| ORM1 | 5 | 153.730.136 |
| MEDAG | 3 | 149.558.767 |
| MLYCD | 11 | 149.088.837 |
| CD300LG | 5 | 147.737.615 |
| GADL1 | 10 | 139.438.535 |
| ADAMTS5 | 10 | 138.825.582 |
| PHYHD1 | 4 | 136.516.182 |
| MEP1B | 5 | 135.223.505 |
| DDIT4L | 7 | 132.753.002 |
| OLFML2B | 4 | 125.161.629 |
| IRF9 | 11 | 119.920.097 |
| KBTBD10 | 9 | 118.884.317 |
| LRRC59 | 4 | 115.785.742 |
| KBTBD5 | 8 | 109.514.782 |
| DBP | 6 | 108.542.127 |
| DGKG | 4 | 106.116.675 |
| ARHGAP36 | 5 | 105.439.678 |
| IL7R | 17 | 100.181.394 |
| ARHGEF25 | 9 | 86.796.006 |
| CDH3 | 5 | 86.466.636 |
| HCAR2 | 12 | 84.599.988 |
| KCNH4 | 5 | 84.264.652 |
| LRPPRC | 8 | 83.009.057 |
| GDA | 8 | 78.695.178 |
| COX4I2 | 11 | 75.813.243 |
| CTHRC1 | 2 | 72.842.474 |
| BASP1 | 2 | 71.616.958 |
| ARSJ | 4 | 65.200.377 |
| CTSW | 3 | 65.138.482 |
| PARP9 | 11 | 61.830.902 |
| CD248 | 4 | 58.486.147 |
| EAF1 | 3 | 58.457.738 |
| PAK1IP1 | 23 | 54.742.685 |
| CSF3R | 9 | 51.951.555 |
| FNDC3B | 3 | 50.257.622 |
| FAM98C | 5 | 48.341.301 |
| FOXN4 | 9 | 48.175.835 |
| CD46 | 10 | 45.586.351 |
| CYP21A2 | 3 | 45.414.463 |
| AMZ1 | 3 | 42.931.659 |
| CRYM | 6 | 42.259.727 |

TABLE 5A-continued

Genes and interlacement.

| Gene | k | Interlacement |
|---|---|---|
| GEMIN5 | 7 | 42.221.750 |
| IGFBP4 | 6 | 37.073.343 |
| ANGPTL1 | 2 | 36.210.590 |
| RAB42 | 3 | 35.578.966 |
| PVRL3 | 2 | 34.884.192 |
| APOBEC2 | 10 | 30.691.203 |
| FAM13C | 2 | 25.170.161 |
| ARID5B | 2 | 23.803.910 |
| DDO | 8 | 23.075.080 |
| CLEC4G | 2 | 22.910.249 |
| FOXO6 | 7 | 21.850.696 |
| FITM1 | 3 | 21.172.074 |
| EMCN | 2 | 20.818.810 |
| MIPEP | 8 | 17.571.818 |
| C1QTNF7 | 2 | 15.833.333 |
| PER1 | 4 | 15.419.443 |
| KRT4 | 3 | 10.681.220 |
| CAND2 | 3 | 0.9989385 |
| NRP2 | 5 | 0.8478632 |
| IL18RAP | 8 | 0.5852316 |
| LAYN | 2 | 0.5490028 |
| IDNK | 2 | 0.3726900 |
| ANKRD33 | 3 | 0.3645833 |
| CD163 | 9 | 0.3310364 |
| EXD3 | 2 | 0.3263618 |
| ADAMDEC1 | 2 | 0.1622613 |
| CHCHD4 | 2 | 0.1226054 |
| AVL9 | 1 | 0.0000000 |
| BTBD6 | 1 | 0.0000000 |
| C1orf110 | 2 | 0.0000000 |
| CCDC114 | 1 | 0.0000000 |
| CCDC86 | 8 | 0.0000000 |
| CDC42SE2 | 1 | 0.0000000 |
| CGA | 1 | 0.0000000 |
| CLDN15 | 1 | 0.0000000 |
| CTXN3 | 2 | 0.0000000 |
| FCAR | 1 | 0.0000000 |
| HN1L | 1 | 0.0000000 |
| HRH2 | 1 | 0.0000000 |
| LRRN4CL | 1 | 0.0000000 |
| MORN5 | 1 | 0.0000000 |
| MRGPRX3 | 1 | 0.0000000 |
| MZT2B | 1 | 0.0000000 |
| NPTX1 | 2 | 0.0000000 |
| PCOLCE2 | 1 | 0.0000000 |
| PHYHIPL | 1 | 0.0000000 |
| PLSCR2 | 1 | 0.0000000 |
| RAMP2 | 1 | 0.0000000 |

TABLE 5B

Genes and interlacing

| Gene | k | Interlacing |
|---|---|---|
| IL1B | 59 | 1.53E+09 |
| TLR2 | 62 | 1.52E+09 |
| STAT1 | 72 | 1.41E+09 |
| ACTA1 | 76 | 1.39E+09 |
| MX1 | 63 | 1.33E+09 |
| ISG15 | 86 | 1.31E+09 |
| TIMP1 | 53 | 1.29E+09 |
| ENO3 | 62 | 1.11E+09 |
| OAS1 | 81 | 1.10E+09 |
| KRT16 | 42 | 1.03E+09 |
| OASL | 78 | 9.24E+08 |
| RERGL | 36 | 7.76E+08 |
| HSPA6 | 43 | 7.63E+08 |
| SOD2 | 41 | 7.43E+08 |
| OAS2 | 75 | 7.33E+08 |
| PYGM | 48 | 7.06E+08 |
| RYR1 | 46 | 7.00E+08 |
| OAS3 | 74 | 6.89E+08 |
| TTN | 59 | 6.29E+08 |
| EIF2AK2 | 41 | 6.21E+08 |
| SOCS3 | 42 | 6.09E+08 |
| ATP2A1 | 57 | 5.42E+08 |
| TCAP | 47 | 5.02E+08 |
| MRTO4 | 33 | 4.98E+08 |
| YARS | 36 | 4.79E+08 |
| IFIT1 | 54 | 4.38E+08 |
| CXCL12 | 41 | 4.35E+08 |
| TUBB6 | 33 | 4.28E+08 |
| ISG20 | 46 | 4.22E+08 |
| TPM4 | 37 | 4.10E+08 |
| PGAM2 | 50 | 4.07E+08 |
| PDGFRL | 25 | 3.96E+08 |
| FOSL1 | 36 | 3.89E+08 |
| FRZB | 25 | 3.82E+08 |
| IFIH1 | 46 | 3.43E+08 |
| CXCL10 | 44 | 3.40E+08 |
| BCL3 | 36 | 3.38E+08 |
| MYH7 | 56 | 3.37E+08 |
| MMP3 | 32 | 3.37E+08 |
| MYH8 | 49 | 3.28E+08 |
| MYH1 | 49 | 3.26E+08 |
| PGK1 | 27 | 3.06E+08 |
| CDC6 | 27 | 2.99E+08 |
| POLA2 | 12 | 2.96E+08 |
| C3 | 21 | 2.94E+08 |
| GYG1 | 9 | 2.92E+08 |
| TNNC2 | 53 | 2.71E+08 |
| FCN2 | 6 | 2.68E+08 |
| RUVBL1 | 27 | 2.65E+08 |
| IFIT3 | 52 | 2.65E+08 |
| PROCR | 4 | 2.59E+08 |
| ASPN | 25 | 2.58E+08 |
| ADAMTS4 | 8 | 2.54E+08 |
| SAMD9L | 23 | 2.54E+08 |
| DDX58 | 41 | 2.44E+08 |
| MYLK2 | 35 | 2.41E+08 |
| PER2 | 12 | 2.41E+08 |
| CACNA1S | 30 | 2.40E+08 |
| IFI44L | 29 | 2.40E+08 |
| CSRP3 | 38 | 2.39E+08 |
| PPP1R3A | 13 | 2.35E+08 |
| MTHFD1L | 28 | 2.34E+08 |
| PTPN1 | 21 | 2.33E+08 |
| MYH3 | 49 | 2.30E+08 |
| MYOT | 35 | 2.26E+08 |
| ACTN2 | 44 | 2.25E+08 |
| ANKRD1 | 40 | 2.25E+08 |
| MMP8 | 26 | 2.16E+08 |
| SH3BGR | 14 | 2.15E+08 |
| SLPI | 21 | 2.14E+08 |
| NEB | 45 | 2.12E+08 |
| CAV3 | 36 | 1.97E+08 |
| TNNI1 | 43 | 1.94E+08 |
| IFITM1 | 31 | 1.88E+08 |
| RBPJ | 27 | 1.88E+08 |
| CCL7 | 24 | 1.87E+08 |
| TREM1 | 9 | 1.74E+08 |
| MYL2 | 45 | 1.74E+08 |
| ETV6 | 17 | 1.73E+08 |
| TNNC1 | 48 | 1.70E+08 |
| TEAD4 | 28 | 1.68E+08 |
| MYLPF | 45 | 1.67E+08 |
| DPH5 | 20 | 1.66E+08 |
| PRKCQ | 34 | 1.66E+08 |
| TNNT3 | 45 | 1.64E+08 |
| NOP58 | 29 | 1.62E+08 |
| CAMP | 21 | 1.61E+08 |
| CKM | 41 | 1.57E+08 |
| HELLS | 22 | 1.55E+08 |
| RPL7 | 26 | 1.54E+08 |
| PLAUR | 17 | 1.52E+08 |
| KBTBD10 | 8 | 1.52E+08 |
| TNNI2 | 42 | 1.51E+08 |
| RAD54L | 25 | 1.50E+08 |

TABLE 5B-continued

Genes and interlacing

| Gene | k | Interlacing |
|---|---|---|
| MYOZ1 | 46 | 1.44E+08 |
| SPATA5 | 22 | 1.42E+08 |
| LMO3 | 11 | 1.40E+08 |
| LMOD2 | 28 | 1.39E+08 |
| DUSP27 | 19 | 1.30E+08 |
| HERC5 | 37 | 1.29E+08 |
| CXCL6 | 22 | 1.27E+08 |
| CCR7 | 29 | 1.26E+08 |
| MCM5 | 17 | 1.26E+08 |
| GNL3 | 29 | 1.26E+08 |
| EPHX1 | 8 | 1.22E+08 |
| DDX60 | 35 | 1.21E+08 |
| MYL3 | 44 | 1.14E+08 |
| ASB10 | 25 | 1.12E+08 |
| NGF | 20 | 1.12E+08 |
| IRF7 | 40 | 1.11E+08 |
| HERC6 | 34 | 1.07E+08 |
| TPPP3 | 5 | 1.05E+08 |
| COX6A2 | 36 | 1.04E+08 |
| FAM115C | 5 | 9.70E+07 |
| TMOD4 | 25 | 9.29E+07 |
| ISL1 | 22 | 9.16E+07 |
| GBP2 | 32 | 9.15E+07 |
| CTSL1 | 20 | 8.78E+07 |
| DUSP26 | 18 | 8.60E+07 |
| CACNA1D | 16 | 8.51E+07 |
| NR1D1 | 8 | 8.26E+07 |
| FGG | 8 | 8.14E+07 |
| CLEC3B | 12 | 8.02E+07 |
| FSCN1 | 18 | 7.46E+07 |
| SGCA | 20 | 7.01E+07 |
| S100A2 | 6 | 6.70E+07 |
| WDR36 | 20 | 6.64E+07 |
| IRG1 | 18 | 6.61E+07 |
| PDSS1 | 11 | 6.53E+07 |
| EPSTI1 | 21 | 6.46E+07 |
| CASQ1 | 39 | 5.88E+07 |
| TTC27 | 24 | 5.32E+07 |
| GBP3 | 19 | 5.31E+07 |
| TG | 11 | 5.09E+07 |
| TNIP3 | 7 | 5.08E+07 |
| F12 | 10 | 5.08E+07 |
| LMOD3 | 20 | 5.02E+07 |
| DHX58 | 26 | 4.99E+07 |
| NOLC1 | 16 | 4.96E+07 |
| DDX56 | 23 | 4.96E+07 |
| IFI44 | 31 | 4.95E+07 |
| UCK2 | 10 | 4.80E+07 |
| RETN | 13 | 4.62E+07 |
| DDX54 | 19 | 4.31E+07 |
| FBXO27 | 3 | 4.25E+07 |
| IL1RN | 14 | 4.04E+07 |
| KRT6B | 8 | 4.03E+07 |
| COX10 | 10 | 3.97E+07 |
| IFITM2 | 19 | 3.83E+07 |
| LTBR | 11 | 3.74E+07 |
| ZNF577 | 24 | 3.73E+07 |
| PODN | 16 | 3.67E+07 |
| NRAP | 27 | 3.65E+07 |
| PRR16 | 5 | 3.63E+07 |
| CXCR2 | 21 | 3.63E+07 |
| CA3 | 11 | 3.56E+07 |
| TRIM54 | 16 | 3.48E+07 |
| ZNF114 | 23 | 3.45E+07 |
| DHRS7C | 10 | 3.32E+07 |
| ORM1 | 6 | 3.24E+07 |
| RGS18 | 12 | 3.20E+07 |
| CARHSP1 | 6 | 3.16E+07 |
| C1QTNF2 | 5 | 3.10E+07 |
| FBXO17 | 3 | 3.08E+07 |
| IGSF10 | 13 | 2.95E+07 |
| IPO4 | 18 | 2.91E+07 |
| CHAF1B | 9 | 2.60E+07 |
| XIRP2 | 10 | 2.55E+07 |
| ARNTL2 | 5 | 2.50E+07 |
| NLRC4 | 9 | 2.50E+07 |
| SGCE | 7 | 2.48E+07 |
| PENK | 14 | 2.22E+07 |
| MYOZ2 | 31 | 2.20E+07 |
| IFI35 | 28 | 2.18E+07 |
| CLEC4E | 10 | 2.14E+07 |
| PER1 | 6 | 2.07E+07 |
| LTBP1 | 7 | 1.88E+07 |
| WDR69 | 9 | 1.83E+07 |
| CLK1 | 6 | 1.81E+07 |
| HSD11B1 | 8 | 1.79E+07 |
| MYBPC1 | 31 | 1.74E+07 |
| SELENBP1 | 4 | 1.71E+07 |
| PGAM4 | 15 | 1.51E+07 |
| UPP1 | 11 | 1.44E+07 |
| HSPB8 | 7 | 1.37E+07 |
| SOS2 | 9 | 1.23E+07 |
| DDX51 | 13 | 1.15E+07 |
| ABCA8 | 5 | 1.09E+07 |
| MRGPRX3 | 4 | 9.09E+06 |
| GLT8D2 | 2 | 9.05E+06 |
| SERPINB6 | 9 | 9.02E+06 |
| OSMR | 8 | 9.01E+06 |
| ENTPD4 | 3 | 8.37E+06 |
| NFATC4 | 9 | 7.77E+06 |
| IRF9 | 26 | 7.67E+06 |
| EAF2 | 8 | 7.65E+06 |
| TFF3 | 7 | 7.44E+06 |
| NOTUM | 9 | 7.14E+06 |
| PARP9 | 21 | 7.07E+06 |
| DBP | 3 | 6.99E+06 |
| HK3 | 18 | 6.51E+06 |
| ABRA | 18 | 6.41E+06 |
| PIWIL1 | 5 | 6.05E+06 |
| COTL1 | 4 | 6.04E+06 |
| PAEP | 3 | 5.95E+06 |
| PTX3 | 6 | 5.59E+06 |
| CSF3R | 7 | 5.13E+06 |
| SMPX | 25 | 4.87E+06 |
| NPHS1 | 6 | 4.64E+06 |
| SLCO4A1 | 2 | 4.44E+06 |
| MYOM3 | 10 | 4.38E+06 |
| XAF1 | 26 | 4.10E+06 |
| HCAR2 | 10 | 3.91E+06 |
| APOBEC2 | 14 | 3.82E+06 |
| TCEAL7 | 2 | 3.70E+06 |
| CD300A | 2 | 3.50E+06 |
| PLSCR4 | 3 | 3.32E+06 |
| GSTM4 | 2 | 3.25E+06 |
| CMYA5 | 14 | 3.21E+06 |
| DDIT4L | 3 | 3.11E+06 |
| SLC4A7 | 5 | 2.97E+06 |
| ITM2A | 2 | 2.94E+06 |
| ADAMTS8 | 4 | 2.74E+06 |
| APOBEC3A | 3 | 2.69E+06 |
| IL13RA1 | 8 | 1.88E+06 |
| FGL1 | 2 | 1.72E+06 |
| B4GALNT4 | 3 | 1.30E+06 |
| ADAMTS5 | 6 | 1.22E+06 |
| LILRB3 | 2 | 1.16E+06 |
| ZNF593 | 11 | 1.01E+06 |
| NTNG1 | 3 | 9.80E+05 |
| CDO1 | 2 | 8.69E+05 |
| TMEM178A | 2 | 7.05E+05 |
| LRRC59 | 2 | 6.58E+05 |
| STEAP4 | 3 | 4.00E+05 |
| SLC39A14 | 5 | 3.45E+05 |
| LPGAT1 | 2 | 2.82E+05 |
| ZWILCH | 5 | 2.64E+05 |
| ADAMTS9 | 3 | 4.76E+04 |
| ANGPTL1 | 1 | 0.000000E+00 |
| AVL9 | 1 | 0.000000E+00 |
| BCMO1 | 1 | 0.000000E+00 |
| CATSPER3 | 2 | 0.000000E+00 |
| CCDC86 | 3 | 0.000000E+00 |
| DCTPP1 | 1 | 0.000000E+00 |
| EMCN | 1 | 0.000000E+00 |

TABLE 5B-continued

Genes and interlacing

| Gene | k | Interlacing |
|---|---|---|
| KRT4 | 1 | 0.000000E+00 |
| NELL2 | 1 | 0.000000E+00 |
| PLAC8 | 6 | 0.000000E+00 |
| PRR5 | 5 | 0.000000E+00 |
| SAA4 | 1 | 0.000000E+00 |
| SLC35A4 | 2 | 0.000000E+00 |
| STEAP3 | 1 | 0.000000E+00 |
| TSC22D3 | 2 | 0.000000E+00 |

Example 4. Systems Biology Methods

Systems Biology applied to complex biological systems has powerful tools to discriminate and elucidate pathways. However, in vivo analysis of the transcription of multiple cell tumors brings with it many uncertainties arising from the overlapping effects of multi-cell transcriptions. Therefore, interactions between tumor cells (melanoma), stroma (fibroblasts, macrophages, mast cells and others), epidermal, immunological, endothelial and muscle cells treated with Amblyomin-X can be described and hypotheses can be launched for future validations. With these concepts in mind, the Systems Biology hypothesis is supported by enrichment analysis and enriched network features, based on transcriptomic data. As mentioned earlier, the data were obtained from algorithms and databases of protein-protein interactions (PPI) and Reactome, Metacore. Gene expressions of confusional transcripts were observed, such as the DEGs related to Actins and Calcium, involving possible processes such as "Endoplasmic Reticulum Stress" (ER-stress), "Cytoskeleton Remodeling" and "Muscle contraction". On the other hand, there are interesting, orchestrated responses between "Immune System", "Inflammation", "Apoptosis" and the first two previous pathways, "ER Stress" and "Cytoskeleton Remodeling". Then, we intend to present some of the genes, pathways, and networks with greater statistical significance in relation to the publications of the state of the art, supporting evidence that Amblyomin-X acts in apoptosis, dinein transport, inflammation, proteasome inhibition in relation to tumor cells, but also adding new pathways and evidence. All the following results are based on the results from the Metacore database.

Example 5. Administration of the compound of the invention and activation of different pathways Right after the injection of the drug, many processes could be taking place such as hypoxia, healing wounds, external organic compound effects, drug action effects, among others. However, four different canonical innate immune systems have been notably found: 1) Toll-like Receptor (TLR) pathways, 2) RIG-like Receptor (RLR) pathways, 3) OAS, and 4) Oncostatin M pathways. TLR, RLR and Oncostatin M are generally related to the production of cytokines and RLR is also related to the production of interferon. As is well known, the innate immune system is the first immune response of skin tissues against external pathogens. Peripheral skin melanoma cells consist of many different cell types, and many of these cells can respond to external disturbances through inflammatory cytokines and other paracrine molecules. Infection by viruses and bacteria triggers Pattern Recognition Receptors (PRR), like TLRs, but after cell invasion they can be recognized by closed-box helicases (DDX), interferon-induced helicases (IFIH) genes and RNase L, such as: DDX58 (RIG-I), DDX60, IFIH1 (MDA5) and OAS (OAST, 2 or 3), are all present as DEGs. Each of these genes has specialized functions for recognizing DNA or RNA in the cytosol and, right after starting the antiviral response, the pro and anti-inflammatory responses begin. Possibly, TLRs induced the first response to increase the expression levels of many inflammatory cytokines at the beginning, after the injection of Amblyomin-X. RLRs continuously induce the production of IL6, IL8 and IP10 (CXCL10), important genes in the inflammatory pathway. According to the literature, type 1 Interferons (IFN alpha and IFN beta) must be transcribed in one of the branches of the RLR pathway, via IRF7, but it was not possible to see any transcribed expression. It is also important to note that no expression transcribed for NOXA was seen. Other important pathways that are enriched in 6 h are ER stress and cytoskeleton remodeling. Interestingly, ohman et al.36 described a crosstalk among many RLR proteins and Actin and Tubulin intact proteins close to the mitochondria. In the results of the present invention, ACTN1 and ACTR3 are positively regulated by DEGs; ACTA1 and ACTN2 are highly repressed DEGs; and in relation to the Tubulin family, TUBB and TUBB6 are positively regulated.

The class of the Innate Immune System pathways enriched 30 pathways, of which 29 were highly differentially modulated to 6 h×0 h compared to 12 h×0 h. The "IFN alpha/beta" pathway (FIGS. 1A/1B and 4A/4B) is highly modulated by 6 h×0 h and increases the modulation by 12 h×0 h, but its effectors (upstream genes) were not detected (IFN alpha, beta INF and gamma INF). The "Oncostatin M" pathway (OSM) is a cytokine and a growth regulator with an important role in inflammation and inhibition of tumor growth. The OSM effector was not a DEG, but the receptors were (OSMR and OSM receptor) (FIGS. 5A and 5B). The neutrophils pathways (FIGS. 11A and 11B) and eosinophils (FIGS. 12A and 12B) have been enriched and are important responses for the control of inflammation and apoptosis. According to Metacore, the enriched neutrophil pathways are "Neutrophil migration inhibition by pre-transformation of lipid mediators in COPD" (fdr 1.21e-4), "Chemotaxis: lipoxins inhibitory action on IL-8 and leukotriene B4-induced neutrophil migration" (fdr 4.55e-4), "Impaired lipoxins inhibitory action on neutrophil migration in CF" (fdr 1.15e-2) and "Neutrophils resistance to apoptosis in COPD and preventive impact of the lipid mediator" (fdr 1.44 e-2); and for Eosinophils are: "CCR3 immune response signaling in eosinophils" (fdr 2.12e-3), and "Adhesion of eosinophils and trans endothelial migration in asthma" (fdr 2.38e-2).

Previous experiments supported the 6 h enriched ER stress pathway (FIGS. 8A and 8B; 9A and 9B), and it was assumed that this is an important response in relation to treatment with Amblyomin-X. Amblyomin-X is a Kunitz-type protein homologue, is endocytosed by tumor cells, reaches the vicinity of the ER, inhibits the proteasome machinery and initiates or reinforces ER stress. Another interesting feature is that this molecule is transported within tumor cells, but not in normal human fibroblast cells that do not have phosphatidylserine on the outer side of the cell membrane. ER stress also promotes mitochondrial dysfunction, Cytochrome c release, PARP cleavage, $Ca+^2$ mobilization and caspase activation in SK-MEL-28 and Mia-PaCa-2 cells, positively regulating CASP3. The survival rate of the previous experiment, calculated using cell viability tests, is herein summarized: Mia-PaCa-2 67%, SK-MEL-28 44%, SK-MEL-5 42%, non-tumoral human fibroblasts 100% (rounded values). These numbers indicate that part of the cells possibly survives through a positive unfolded protein response (UPR) and part dies. It is well known that, if persistent stress persists or is severe, and if UPR does not reach its goal (homeostasis), the cell death pathway is a possible destination as the next step. Furthermore, autophagy could also be evoked to recover a global tissue homeostasis, and, in this case, there is the signature of immunogenic cell death (ICD). It is believed that the ICD could explain this.

The compound of the invention proved to be able to activate different pathways in different cells, such as innate immune systems (early: TLR2, RLR and lately: OAS and Oncostatin M), and in parallel inhibits the proteasome systems leading the cell to ER stress followed by apoptosis. The analysis of the results of the transcriptome leads to the conclusion that the pathway sequence shown in the figure (Supp Mat PPT) occurs.

Inflammation and innate immune system pathways appear to be orchestrated at the beginning of treatment with the compound of the invention. No IFN transcripts were detected in these experiments. The first step should be the damage of the tumor cells followed by the interaction of the compound of the invention with many types of cells that make up the tumor environment. In the beginning, the innate immune system is activated and regulates IL1B, IL6, IL8, IPlO and CCL2. RLR via which has its expression DNA-RNA (RIG-I, LGP2, MDA5) increased in time, can increase the transcript IL8, IL6, IPlO, less modulated IL12 and Alph TNF. Theoretically, by way of IRF7, IFN alpha and IFN beta should be transcribed. There is a great deal of discussion in the literature about how the RLR pathway is activated without virus invasion. One possible answer is to activate endogenous retrovirus transcription in a genomic region that was previously protected by methyl groups. After 6 hours, it is observed that many genes of the RLR pathway have their expressions increased, and close to 12 h OAS and Oncostatin M responses are activated, as shown in FIGS. 1, 3, 4 and 5.

Many apoptotic signals are elevated in 6 h (CASP3, CASP4, Cytochrome c) and their expression decreased in 12 h, but survival signs also have this behavior (BIRC2, BIRC3, ATF6, SOD2), in addition to SOD2 (until 6 h×0 h, up 12 h×0 h), the only pro-survival signal that keeps regulated at both times. At 6 h, Cytochrome c is regulated, and the possibility of mitochondrial damage has been hypothesized, for which the release of the protein needs to be validated. Calpain 2 and HSP60, both DEGs and BAX (verified in previous in vitro experiments) supported this hypothesis. ER-stress is supposed to peak at 6 h, since GRP78, IP3R1, ATF6, XBP1, PDIA6 and endoplasmin (HSP90B1) are upregulated at this time.

Dead cells and cell survival are seen in previous experiments. Therefore, it is believed that HBGB1 is present in the external environment. Furthermore, calreticulin (CALR) is an important DEG at 6 h, and its co-location close to the ER, on the inner side of the cell membrane, and also on the outer side, must be validated. To support immunogenic cell death (ICD), traces that autophagy may occur in some cells must be found. According to Jheng et al., the signs upstream of autophagy are ER-stress signaling: CASP4, CASP12, JNK, ATF6, CHOP, ATF4, EIF2AK3 (PERK), EIF2A and GADD34. Many of these genes are well expressed, but not modulated, and autophagy can begin later in some cells.

The present invention presents a hypothetical view that the compound of the invention can kill some cells, allowing others to survive and elicit the ICD mechanism via ER-stress and autophagy with the release of HMBG1 and CALR.

Possible IFN gamma proteins can reach TLR2, or even paracrine IL1B, from nearby macrophages, resulting in increased transcription of IL6, CCL2, IL8 and IPlO (CXCL10).

Simultaneously, according to previous studies, Amblyomin-X recognizes phosphatidylserine present in cancer membranes, and is transported via endocytosis vesicles into the cell. Since the compound of the invention has the ability to inhibit the proteasome machinery, some proteins begin to accumulate near the Endoplasmic Reticulum and new chaperones are transcribed (HSP60, HSP70, HSP90) similar to what is called the Unfolded Protein Response (UPR), an important function for the stress pathway of the Endoplasmic Reticulum. The HMGB1-RAGE signaling pathway (FIGS. 7A and 7B) it is also enriched, indicating that HMGB1 is possibly the main effector that induces the transcription of IL6, IL1B, IL8, IL1RN, PAIL and Chromogranin A (CHGA). Some of them are cytokines secreted to the extracellular environment, and IL8 is a chemoattractant for neutrophils. Neutrophils also respond to two other DEGs, such as C5aR and glomerular colony stimulated factor (G-CSF), which are upregulated in 6 h. G-CSF may be an important key gene, down regulating SDF-1, which in turn is a cytokine related to cancer metastasis and orchestrates the balance between neutrophil adhesion, bone marrow and hematopoietic stem cells, as shown in (FIGS. 15, 16A and 16B). Finally, another interesting, regulated cytokine is CCL2, which has as one of its roles the stimulation of helper T cell maturation, favoring the transcription of Th2 compared to Th1 as shown in (FIGS. 12A and 12B).

Inflammation

As mentioned earlier, there must be a first response increasing the expression level of many cytokines, most of them related to inflammatory pathways, such as IL1B (produced by activated macrophages and proteolytically processed to the active form by CASP1), IL-1R1, IL-6 (the important protein that acts in acute and chronic inflammation), CXCL8 (IL-8, secreted mainly by neutrophils) and CCL2 (involved in immunoregulatory and inflammatory processes and acting as an antitumor gene). Analyzing different networks and enrichment pathways, many different inflammatory responses can be seen, many of them resulting in increased expression levels of the previously mentioned cytokines, in addition to genes such as Beta-Defensin 2 (DEFB4A, microbicidal and cytotoxic peptides secreted by neutrophils and regulated by inflammation) (FIG. 18). Another inflammatory pathway is related to the TREM1 response (FIG. 17), possibly increasing the expression levels of IL-6, CCL2 and IL-8. Finally, the TNF pathway has also been enriched, although TNF A-alpha has been moderately regulated, being a pro-inflammatory cytokine secreted by macrophages and also produced downstream of the RLR pathway. Furthermore, the TNF receptor TNF-R1 is a DEG. Downstream of TNF-R1, two important pathways are seen, one by means of AP1, reaching two DEGs, Stromelysin-1 (MMP3, Matrix Metalloproteinase 3) and IL6, and another by means of the NFKB complex and possibly related to important DEGs such as IL-6, IL1B, SFK (SRC kinase family, a proto-oncogene related to development and growth) and IL1RN (an IL1 receptor agonist that inhibits=A and IL1B, modulating the inflammatory response of the IL1 gene family). Finally, Oncostatin M is a pro-inflammatory mediator, and its pathway can be seen in FIGS. 5A and 5B.

Summarizing

The compound of the invention selectively enters cancer cells only through endocytosis (perhaps through the clathrin-independent pathway), binding to the outer membrane attracted by phosphatidylserine affinity, and from there, inside the cell, inhibits the proteasome machinery.

Phosphatidylserine plays a dual role: it helps the compound of the invention entering the cell and it is also related to CALR externalization.

Innate immune response is possibly present in the first hours, releasing IL8, IL6, IP10, and maybe IL12 and TNF-alpha.

The RLR and Macrophage/TLR2 cascades increase the production of many pro-inflammatory cytokines.

The ER is stressed (and possibly the mitochondria is also stressed) and the UPR response begins, however many new proteins remain in a bad folding format, inducing apoptosis; HSP60 and Calpain-2 they are upregulated at 6 h promoting Cytochrome C production, which can also be released from the mitochondria; if confirmed, it suggests mitochondrial stress and apoptosis.

The mRNA molecules are produced, and their translation is controlled by the EIF2A proteins family; also, a UPR feature.

The OAS gene family is highly expressed and induces the action of RNase L, fragmenting many mRNA molecules because the antiviral cascade is still active.

The RLR pathway appears to respond in the first hours and is enhanced between 4h and 12 h, inducing the transcription of more inflammatory cytokines and DNA-RNA antiviral Sensors; Via RLR apparently collaborates in the processes of apoptosis, but neither by means of NOXA nor STING; it was not possible to see any expression of IFN alpha, IFN beta, only of IL8, IL6 and IP10 cytokines.

The signs of inflammation are evident with a central role for genes like IL6, IL1B, IL8 and CCL2; The IL17 genes (C and F) have very low expressions; IP10 is DEG only at 12 h.

The pro-apoptosis (CASP3, CASP4, Cytochrome C) and pro-survival (BIRC2, BIRC3, ATF6, S0D2) genes are expressed to support the survival-death dual hypothesis.

Some cells die and others survive as a result of cell tensions and responses; therefore, signs of death such as HMGB1 and ATP can be released outside the cells.

The main hypothesis, in addition to innate immune responses, is the response of immunogenic cell death (ICD).

IFN alpha, IFN beta and IFN gamma, showed no expression.

Interatomic

Table 6 shows the lists of ligands identified in the extract extracted from tumor.

TABLE 6

Ligands identified in the tumor extract.

| Protein ID | Adhesion | Description | −10 lgP | Coverage (%) | # Peptides | Single # | Average mass |
|---|---|---|---|---|---|---|---|
| 54205 | P00004 | Cytochrome c | 256.58 | 33 | 9 | 9 | 11833 |
| 213 | P35747 | Serum albumin | 210.89 | 9 | 6 | 5 | 68599 |
| 5340 | P80010 | Plasminogen (Fragment) | 180.62 | 15 | 5 | 5 | 37132 |
| 1915 | A2Q0Z0 | Elongation Factor 1-alpha 1 | 168.13 | 16 | 11 | 11 | 50125 |
| 146183 | Q28372 | Gelsolin | 164.13 | 7 | 6 | 6 | 80827 |
| 60 | P60708 | Cytoplasmic actin 1 | 147.24 | 11 | 3 | 3 | 41737 |
| 2335 | Q28377 | Fibronectin (Fragment) | 137.04 | 5 | 3 | 3 | 57577 |
| 476 | P18907 | alpha-1 Sodium/potassium-carrier ATPase subunit | 110.96 | 11 | 16 | 16 | 112697 |
| 83992 | Q2QLA2 | Cortactin 2 binding protein | 106.07 | 4 | 10 | 10 | 181383 |
| 217 | P12762 | Mitochondrial aldehyde dehydrogenase | 90.23 | 12 | 8 | 7 | 54166 |
| 301 | Q8HZM6 | Annexin A2 | 89.2 | 16 | 6 | 5 | 38604 |
| 7431 | F7B5C4 | Uncharacterized protein | 87.29 | 16 | 7 | 5 | 53652 |
| 1621 | Q9XTA0 | Dopamine beta-hydroxylase | 86.67 | 10 | 10 | 9 | 68229 |
| 7097 | Q6T752 | Toll 2 type receptors | 86.62 | 15 | 16 | 16 | 90164 |
| 7431 | K9KCT0 | Vimentin type | 81.17 | 16 | 7 | 4 | 53652 |
| 7171 | P02561 | Alpha 4 tropomyosin chain | 48.61 | 8 | 2 | 2 | 28523 |
| 10367 | Q9N0V5 | Calcitonin | 42.16 | 11 | 2 | 2 | 15358 |
|  | P05002 | Interferon omega 2 | 38.98 | 11 | 3 | 2 | 22132 |
| 4233 | Q2QLA9 | Hepatocyte growth factor receptor | 36.98 | 2 | 3 | 3 | 154560 |
| 2099 | Q9TV98 | Estrogen receptor | 36.92 | 3 | 2 | 2 | 66104 |
| 4538 | P48655 | NADH-ubiquinone oxidoreductase chain 4 | 36.62 | 7 | 4 | 4 | 51748 |
| 1687 | Q7YS54 | Homology of proteins 5 with non-syndromic hearing loss | 35.97 | 2 | 2 | 2 | 54883 |
| 5213 | Q867C9 | ATP-dependent muscle type 6-phosphofructokinase | 35 | 3 | 3 | 3 | 85282 |

TABLE 6-continued

Ligands identified in the tumor extract.

| Protein ID | Adhesion | Description | −10 lgP | Coverage (%) | # Peptides | Single # | Average mass |
|---|---|---|---|---|---|---|---|
| 4359 | Q6WEB5 | Myelin protein P0 | 34.63 | 6 | 2 | 2 | 27485 |
| 121278 | Q0EAB8 | Tryptophan 5-hydroxylase 2 | 34.5 | 3 | 2 | 2 | 56087 |
| 2984 | O46689 | Acute mitochondrial steroidogenic regulatory protein | 33.73 | 6 | 2 | 2 | 31853 |
| 5406 | P29183 | Pancreatic triacylglycerol lipase (Fragment) | 32.52 | 3 | 2 | 2 | 50921 |
| 135 | Q6TLI7 | A2a adenosine receptor | 32.24 | 2 | 2 | 2 | 44894 |
| 1836 | Q65AC2 | Sulfate carrier | 31.47 | 2 | 2 | 2 | 81489 |
| 4599 | Q28379 | Interferon protein induced GTP-ligand Mx1 | 28.87 | 3 | 2 | 2 | 75566 |
| 6013 | P22969 | Prorelaxin | 28.8 | 5 | 2 | 2 | 20721 |
| 3320 | Q9GKX7 | HSP 90-alpha heat shock protein | 27.97 | 2 | 2 | 2 | 84770 |
| 3623 | P55101 | Inhibin alpha chain | 26.37 | 2 | 2 | 2 | 39423 |
| 6352 | Q8MKD0 | C-C chemokine motif 5 | 25.96 | 5 | 2 | 2 | 10159 |
| 2495 | Q8MIP0 | Ferritin heavy chain | 25.64 | 6 | 2 | 2 | 21269 |
| 914 | P37998 | CD2 T cell surface antigen | 25.29 | 5 | 2 | 2 | 38864 |
| 4193 | P56951 | Ubiquitin ligase E3 Mdm2 protein | 23.37 | 3 | 4 | 2 | 149114 |
| 6648 | Q9XS41 | Mitochondrial superoxide dismutase [Mn] | 22.64 | 4 | 2 | 2 | 24739 |
| 7172 | Q3BCR6 | Thiopurine S-methyltransferase | 22.49 | 3 | 2 | 2 | 28118 |
| 7040 | O19011 | Beta 1 transforming growth factor | 21.53 | 3 | 2 | 2 | 43975 |
| 7157 | P79892 | P53 cell tumor antigen (Fragment) | 20.22 | 3 | 2 | 2 | 30985 |

Temporal validation of RNA-seq by qRT-PCR

The RNA-seq was carried out to identify the transcriptional regulation mechanisms associated with tumor regression of animals that were treated with the compound of the invention after 6 and 12 hours. The DEGs related to the innate immune response, apoptosis and inflammation were selected for validation with qRT-PCR (Table 7 a, b, c).

56 DEGs related to the immune and inflammation system were chosen, and 6 newer DEGs were calculated using BDIA for validation of the qRT-PCR. According to the median expression, these genes have been divided into 3 groups: highly expressed, moderately expressed, and poorly expressed. 42 of these 56 genes were chosen for validation of the qRT-PCR. Highly expressed genes (i.e., at least one median 50 CPM): ACTN1, CAD, CCL2, CDO1, FSCN1, HMOX1, HSPA6, IFI35, IL1RN, IRF9, MYLPF, OAS2, PER1, SLPI, STAT1 and TLR2. Moderately expressed genes (i.e., expression (CPM)<50): BCL3, BIRC3, CTSL, CXCL6, DDX58, F12, FOSL1, IFIH1, IFIT1, IL13RA1, IL1B, ITGA1, MYH1, MYH3, MYL2, NTNG1, PARP9, PIK3R6, RUNX1, SAA1, SELP, SOCS3, TAT, TEAD4, THBS1 and TREM1. Poorly expressed genes (i.e., median expression <5 CPM): BATF3, CAV3, CCR7, CDH15, EIF2AK2, ETV6, IL18RAP, IL7R, MYLK2, NECTIN3, NLRC4, NLRP12, OAS3 and PRKCQ.

The person skilled in the art will value the knowledge herein presented and will be able to reproduce the invention in the presented embodiments and in other variants and alternatives, covered by the scope of the following claims.

Tabel 7A
DEGs related to the innate immune response, apoptosis, and inflammation

| gene_id | symbol | entrezid | logFC6 | fdr6 | logFC12 | fdr12 | median1 | median2 | median3 |
|---|---|---|---|---|---|---|---|---|---|
| ENSECAG00000019476 | ACTN1 | 87 | 1.003274 | 2.76E−02 | 1.005997 | 8.95E−02 | 80.48236 | 153.3001 | 165.3412 |
| ENSEAG00000014690 | CAD | 790 | 1.226793 | 3.86E−03 | 1.027948 | 7.93E−02 | 25.08148 | 52.81868 | 50.33678 |
| ENSECAG00000023949 | CCL2 | 6347 | 2.790141 | 1.88E−03 | 3.516916 | 4.32E−04 | 25.87876 | 171.527 | 418.8519 |
| ENSECAG00000012826 | CDO1 | 1036 | −1.785163 | 1.96E−02 | −2.407696 | 1.20E−02 | 76.10831 | 22.45353 | 12.70687 |

Tabel 7A
DEGs related to the innate immune response, apoptosis, and inflammation

| ENSECAG 00000008056 | FSCN1 | 6624 | 1.457395 | 2.00E−02 | 1.830736 | 9.05E−03 | 43.16424 | 97.18602 | 152.3466 |
|---|---|---|---|---|---|---|---|---|---|
| ENSECAG 00000001129 | HMOX1 | 3162 | 1.442806 | 2.01E−02 | 1.116878 | 2.39E−01 | 55.11232 | 99.10729 | 105.6427 |
| ENSECAG 00000004180 | HSPA6 | 3310 | 5.375559 | 4.98E−04 | 4.549971 | 1.02E−02 | 1.690108 | 15.92756 | 53.79293 |
| ENSECAG 00000001598 | IFI35 | 3430 | 1.512998 | 1.55E−03 | 1.638749 | 3.58E−03 | 19.93591 | 48.07028 | 66.19103 |
| ENSECAG 00000004312 | IL1RN | 3557 | 2.823176 | 3.13E−03 | 2.805385 | 1.25E−02 | 28.03596 | 120.3935 | 118.3058 |
| ENSECAG 00000024429 | IRF9 | 10379 | 1.13631 | 8.01E−03 | 1.461662 | 2.37E−03 | 34.55774 | 72.39045 | 85.23673 |
| ENSECAG 00000017437 | MYLPF | 29895 | −5.872047 | 3.18E−06 | −5.427971 | 1.09E−03 | 77.08533 | 1.313922 | 1.628965 |
| ENSECAG 00000014422 | OAS2 | 4939 | 1.462622 | 1.81E−02 | 2.491031 | 9.19E−05 | 10.51689 | 34.26109 | 82.84068 |
| ENSECAG 00000013291 | PER1 | 5187 | −1.473567 | 2.76E−07 | −1.139048 | 2.83E−03 | 92.26096 | 32.08106 | 39.99363 |
| ENSECAG 00000016161 | SLPI | 6590 | 3.008671 | 7.54E−03 | 3.050831 | 2.13E−02 | 79.35763 | 230.2294 | 620.7695 |
| ENSECAG 00000009039 | STAT1 | 6772 | 1.085014 | 1.17E−02 | 1.26715 | 1.12E−02 | 34.02156 | 76.47681 | 83.63719 |
| ENSECAG 00000018028 | TLR2 | 7097 | 1.5586 | 4.16E−03 | 1.838635 | 3.29E−03 | 26.67079 | 59.58356 | 93.64169 |

| gene_id | refseq |
|---|---|
| ENSECAG 00000019476 | Alpha actinins belong to the spectrin gene superfamily that represents a diverse group of cytoskeletal proteins, including the alpha and beta and dystrophin spectrins. Actinin alfa is the actin-binding protein with multiple functions in different types of cells. In non-muscle cells, the cytoskeleton isoform is found along bundles of microfilaments and junctions of the adherent type, where it is involved in the actin binding to the membrane. In contrast, skeletal, cardiac, and smooth muscle isoforms are located on disc Z and in dense analogous bodies, where they help anchor myofibrillar actin filaments. This gene encodes a non-muscular, cytoskeletal, alpha-actinin isoform and maps the same place as the structurally similar erythroid beta spectrin gene. Three transcribed variants encoding different isoforms were found for this gene, [provided by RefSeq, July of 2008] |
| ENSEAG 00000014690 | The de novo synthesis of pyrimidine nucleotides is necessary to proliferate mammalian cells. This gene encodes the trifunctional protein that is associated with the enzymatic activities of the first three enzymes in the 6-stage pyrimidine biosynthesis pathway: carbamoyl phosphate synthase (CPS II), aspartate transcarbamylase and dihydroorotase. This protein is regulated by the mitogen activated protein kinase cascade (MAPK), which indicates a direct link between the activation of the MAPK cascade and the de novo biosynthesis of pyrimidine nucleotides. Alternative splicing results in multiple transcript variants that encode different isoforms, [provided by RefSeq, April of 2015] |
| ENSECAG 00000023949 | This gene is one of several cytokine genes grouped in the chromosome 17 q arm. Chemokines are a superfamily of secreted proteins involved in immunoregulatory and inflammatory processes. The superfamily is divided into four subfamilies based on the disposition of the N-terminal cysteine residues of the mature peptide. This chemokine is a member of the CC subfamily that is characterized by two adjacent cysteine residues. This cytokine has chemotactic activity for monocytes and basophils, but not |

Tabel 7A
DEGs related to the innate immune response, apoptosis, and inflammation

|  |  |
|---|---|
|  | for neutrophils or eosinophils. It has been implicated in the pathogenesis of diseases characterized by monocytic infiltrates, such as psoriasis, rheumatoid arthritis, and atherosclerosis. It binds to chemokine receptors CCR2 and CCR4. [provided by RefSeq, July of 2013] |
| ENSECAG 00000012826 | CDO1 (Cysteine Dioxigenase Type 1) is a protein coding gene. Diseases associated with CDO1 include Hepatoblastoma and Adenocarcinoma of the Esophagus. Among its related pathways are Metabolism and the metabolism of sulfur amino acids. GO notes related to this gene include iron ions binding and dioxigenase activity. |
| ENSECAG 00000008056 | This gene encodes a member of the fascine family of actin-binding proteins. Fascine proteins organize F-actin in parallel bundles and are necessary for the formation of actin-based cell protrusions. The coded protein plays a critical role in cell migration, motility, adhesion, and cell interactions. The expression of this gene is known to be regulated by several microRNAs, and the overexpression of this gene can play a role in the metastasis of multiple types of cancer, increasing cell motility. The expression of this gene is also a marker for Reed-Sternberg cells in Hodgkin's lymphoma. A pseudogene of this gene is located on the long arm of chromosome 15. [provided by RefSeq, September of 2011] |
| ENSECAG 00000001129 | Heme oxygenase, an essential enzyme in heme catabolism, cleaves heme to form biliverdin, which is subsequently converted to bilirubin by biliverdin reductase and carbon monoxide, a putative neurotransmitter. The activity of heme oxygenase is induced by its heme substrate and by several non-heme substances. Heme oxygenase occurs in two isoenzymes, an inducible heme oxygenase-1 and a constitutive heme oxygenase-2. HMOX1 and HMOX2 belong to the heme oxygenase family, [provided by RefSeq, July of 2008] |
| ENSECAG 00000004180 |  |
| ENSECAG 00000001598 | IFI35 (Interferon 35-Induced Protein) is a protein coding gene. Diseases associated with IFI35 include stomatitis and lymphocytic choriomeningitis. Among its related pathways are interferon signaling and cytokine signaling in the immune system. An important parallel of this gene is the NMI. |
| ENSECAG 00000004312 | The protein coded by this gene is a member of the interleukin cytokine family 1. This protein inhibits the activities of alpha interleukin 1 (IL1A) and beta interleukin 1 (IL1B) and modulates a variety of immune and inflammatory responses related to interleukin 1. This gene and five other closely related cytokine genes form a set of genes spanning approximately 400 kb on chromosome 2. A polymorphism of this gene is reported to be associated with an increased risk of osteoporotic fractures and gastric cancer. Several alternatively processed transcribed variants that encode distinct isoforms have been reported, [provided by RefSeq, January of 2016] |
| ENSECAG 00000024429 | IRF9 (Interferon Regulatory Factor 9) is a protein coding gene. Diseases associated with IRF9 include skin papilloma and hepatitis C. Among its related pathways are interferon type II (IFNG) signaling and the PI3K-Akt signaling pathway. The GO annotations |

Tabel 7A
DEGs related to the innate immune response, apoptosis, and inflammation

|  |  |
|---|---|
|  | related to this gene include the activity of the transcription factor, the binding to the sequence-specific DNA and the binding to the DNA of the regulatory region. An important parallel of this gene is IRF8. |
| ENSECAG 00000017437 | MYLPF (Myosin Light Chain, Phosphorylable, Fast Skeletal Muscle) is a protein coding gene. Among its related pathways are focal adhesion and Sertoli-Sertoli cell junction dynamics. The GO annotations related to this gene include binding to the calcium ion and structural constituent of the muscle. An important parallel of this gene is MYL10. |
| ENSECAG 00000014422 | This gene encodes a member of the family of 2-5A synthetases, essential proteins involved in the innate immune response to viral infection. The coded protein is induced by interferons and uses adenosine triphosphate in specific 2'nucleotide transfer reactions to synthesize 2',5'-oligoadenylates (2-5As). These molecules activate latent RNase L, which results in the degradation of viral RNA and the inhibition of viral replication. The three known members of this family of genes are located in a cluster on chromosome 12. Alternatively, transcribed variants have been described that encode different isoforms, [provided by RefSeq, July of 2008] |
| ENSECAG 00000013291 | This gene it is a member of the Period gene family and is expressed in a circadian pattern in the suprachiasmatic nucleus, the main circadian pacemaker in the mammalian brain. Genes in this family encode components of circadian rhythms of locomotor activity, metabolism, and behavior. This gene is up regulated by the CLOCK/ARNTL heterodimers, but then suppresses this upregulation in a feedback loop using PER/CRY heterodimers to interact with CLOCK/ARNTL. This gene polymorphisms can increase the risk of getting certain types of cancer. Alternative splicing has been observed in this gene; however, these variants have not been fully described, [provided by RefSeq, January of 2014] |
| ENSECAG 00000016161 | This gene encodes a secreted inhibitor that protects epithelial tissues from serine proteases. It is found in several secretions, including seminal plasma, cervical mucus, and bronchial secretions, and has an affinity for trypsin, leukocyte elastase and cathepsin G. Its inhibitory effect contributes to the immune response, protecting the epithelial surfaces from attack by endogenous proteolytic enzymes. This antimicrobial protein has antibacterial, antifungal, and antiviral activity, [provided by RefSeq, November of 2014] |
| ENSECAG 00000009039 | The protein coded by this gene is a member of the STAT protein family. In response to cytokines and growth factors, members of the STAT family are phosphorylated by receptor-associated kinases, and then form homo or heterodimers that translocate to the cell nucleus where they act as activators of transcription. This protein can be activated by several ligands, including interferon-alpha, interferon-gamma, EGF, PDGF and IL6. This protein mediates the expression of a variety of genes, which is considered important for cell viability in response to different cellular stimuli and pathogens. Two alternatively processed transcript variants that encode distinct isoforms have been described, [provided by RefSeq, July of 2008] |

Tabel 7A
DEGs related to the innate immune response, apoptosis, and inflammation

| | | |
|---|---|---|
| | ENSECAG 00000018028 | The protein coded by this gene it is a member of the Toll-like receptor (TLR) family, which plays a key role in the recognition of pathogens and in the activation of innate immunity. TLRs are highly conserved from Drosophila for humans and share structural and functional similarities. This protein is the cell surface protein that can form heterodimers with other members of the TLR family to recognize conserved molecules derived from microorganisms known as pathogen-associated molecular patterns (PAMPs). The activation of TLRs by PAMPs leads to a positive regulation of signaling pathways to modulate the host's inflammatory response. This gene is also thought to promote apoptosis in response to bacterial lipoproteins. This gene has been implicated in the pathogenesis of several autoimmune diseases. Alternative splicing results in multiple transcription variants, [provided by RefSeq, January 2016] |

TABLE 7B
DEGs related to the innate immune response, apoptosis and inflammation

| gene_id | symbol | entrezid | logFC6 | fdr6 | logFC12 | fdr12 | median1 | median2 | median3 |
|---|---|---|---|---|---|---|---|---|---|
| ENSECAG 00000013124 | BCL3 | 602 | 1.936137 | 8.12E−04 | 1.708745 | 1.86E−02 | 11.56478 | 46.57452 | 39.97441 |
| ENSECAG 00000012229 | BIRC3 | 330 | 1.274862 | 3.22E−02 | 0.914585 | 3.73E−01 | 28.29855 | 47.3192 | 47.38031 |
| ENSECAG 00000007210 | CTSL | 1514 | 1.375742 | 1.31E−02 | 1.385028 | 4.65E−02 | 14.33356 | 34.0817 | 33.8889 |
| ENSECAG 00000012742 | CXCL6 | 6372 | 5.944581 | 2.47E−05 | 3.416715 | 6.71E−02 | 0.117873 | 6.189267 | 1.107985 |
| ENSECAG 00000021989 | DDX58 | 23586 | 1.43417 | 2.33E−02 | 1.760214 | 1.38E−02 | 9.662251 | 22.54543 | 31.89639 |
| ENSECAG 00000010619 | F12 | 2161 | 2.55947 | 1.71E−03 | 3.104341 | 6.13E−04 | 0.91761 | 4.891358 | 8.670772 |
| ENSECAG 00000023092 | FOSL1 | 8061 | 4.577606 | 3.70E−06 | 4.028115 | 2.85E−04 | 0.711383 | 14.18345 | 11.45513 |
| ENSECAG 00000007881 | IFIH1 | 64135 | 0.851001 | 2.17E−01 | 1.822844 | 5.17E−03 | 7.70477 | 13.28863 | 27.95496 |
| ENSECAG 00000004433 | IFIT1 | 3434 | 2.574277 | 7.21E−05 | 2.654729 | 3.64E−04 | 4.305026 | 28.13053 | 34.10787 |
| ENSECAG 00000019115 | IL13RA1 | 3597 | 1.407626 | 1.95E−04 | 1.279878 | 7.04E−03 | 11.93182 | 29.30146 | 23.98159 |
| ENSECAG 00000000168 | IL1B | 3553 | 4.309274 | 1.23E−04 | 3.151516 | 2.13E−02 | 1.383081 | 20.23137 | 10.07414 |
| ENSECAG 00000017386 | ITGA1 | 3672 | 1.348086 | 1.86E−02 | 1.094292 | 2.11E−01 | 2.714836 | 7.060046 | 6.155113 |
| ENSECAG 00000022909 | MYH1 | 4619 | −8.39983 | 4.80E−04 | −8.310499 | 1.64E−02 | 34.82201 | 0 | 0 |
| ENSECAG 00000025060 | MYH3 | 4621 | −3.643139 | 2.54E−04 | 3.004454 | 3.41E−02 | 19.16169 | 1.417986 | 1.816813 |
| ENSECAG 00000007867 | MYL2 | 4633 | −8.696907 | 4.15E−04 | −7.917205 | 2.56E−02 | 5.682312 | 0 | 0 |
| ENSECAG 00000016691 | NTNG1 | 22854 | −1.958745 | 3.13E−03 | −2.943364 | 1.18E−03 | 5.708642 | 1.059075 | 0.744026 |
| ENSECAG 00000012331 | PARP9 | 83666 | 1.81581 | 9.65E−04 | 2.108666 | 7.70E−04 | 4.325163 | 16.33833 | 18.55893 |
| ENSECAG 00000017146 | PIK3R6 | 146850 | −1.276586 | 4.34E−04 | −1.356323 | 6.05E−03 | 10.93888 | 5.162471 | 4.433471 |
| ENSECAG 00000003462 | RUNX1 | 861 | 1.722528 | 6.49E−03 | 1.442929 | 1.04E−01 | 3.17072 | 8.948591 | 9.266301 |
| ENSECAG 00000011404 | SAA1 | 6288 | 3.455868 | 1.71E−03 | 3.902343 | 1.69E−03 | 0.731329 | 7.680465 | 11.70194 |
| ENSECAG 00000010918 | SELP | 6403 | 2.595984 | 1.52E−02 | 2.394535 | 7.64E−02 | 5.946949 | 22.34192 | 20.57901 |
| ENSECAG 00000001249 | SOCS3 | 9021 | 2.978711 | 4.96E−05 | 2.42347 | 7.33E−03 | 1.750263 | 12.20652 | 11.57231 |

TABLE 7B-continued

DEGs related to the innate immune response, apoptosis and inflammation

| ENSECAG 00000021565 | TAT   | 6898  | 5.291507 | 3.48E−02 | 5.520961 | 6.06E−02 | 0.089441 | 1.235419 | 9.520038 |
|---------------------|-------|-------|----------|----------|----------|----------|----------|----------|----------|
| ENSECAG 00000011303 | TEAD4 | 7004  | 1.684784 | 5.68E−03 | 1.948997 | 6.16E−03 | 8.944683 | 21.64296 | 39.11542 |
| ENSECAG 00000008923 | THBS1 | 7057  | 1.819392 | 2.80E−02 | 0.87494  | 6.67E−01 | 18.72164 | 43.50112 | 31.31727 |
| ENSECAG 00000017436 | TREM1 | 54210 | 5.55061  | 9.94E−06 | 5.55888  | 5.62E−05 | 1.189625 | 31.36121 | 24.25151 |

| gene_id | refseq |
|---------|--------|
| ENSECAG 00000013124 | This gene is a candidate for proto-oncogene. It is identified by its translocation to the alpha immunoglobulin locus in some cases of B cell leukemia. The protein coded by this gene contains seven replications of ankyrin, which are more closely related to those found in proteins I kappa B. This protein functions as a transcriptional co-activator that activates through its association with NF-kappa B homodimers. The expression of this gene can be induced by NF-kappa B, which is part of the self-regulatory loop that controls the nuclear residence of p50 NF-kappa B. [provided by RefSeq, July of 2008] |
| ENSECAG 00000012229 | This gene encodes a member of the IAP proteins family that inhibit apoptosis by binding to factors associated with the tumor necrosis factor receptor TRAF1 and TRAF2, probably interfering with the activation of ICE-type proteases. This gene encodes a member of the IAP proteins family that inhibit apoptosis by binding to factors associated with the tumor necrosis factor receptor TRAF1 and TRAF2, probably interfering with the activation of ICE-type proteases. The coded protein inhibits apoptosis induced by serum deprivation but does not affect apoptosis resulting from exposure to menadione, a potent inducer of free radicals. Contains 3 baculovirus IAP repeats and an annular domain. Transcription variants encoding the same isoform have been identified, [provided by RefSeq, August of 2011] |
| ENSECAG 00000007210 | The protein coded by this gene is a lysosomal proteinase cysteine that plays an important role in the catabolism of intracellular proteins. Its substrates include collagen and elastin, as well as the alpha-1 protease inhibitor, an important element in controlling neutrophilic elastase activity. The coded protein has been implicated in several pathological processes, including myofibrillary necrosis in myopathies and myocardial ischemia, and in the renal tubular response to proteinuria. This protein, which is a member of the C1 peptidase family, is a dimer composed of disulfide-linked heavy and light chains, both produced from a single protein precursor. Multiple transcribed variants of alternative splicing have been found for this gene, [provided by RefSeq, April of 2012] |
| ENSECAG 00000012742 | |
| ENSECAG 00000021989 | The DEAD-box proteins, characterized by the conserved motif Asp-Glu-Ala-Asp (DEAD), are supposed RNA helicases that are implicated in various cellular processes involving the binding of RNA and alteration of the secondary structure of RNA. This gene encodes a protein containing RNA DEAD-box protein helicase motifs and a caspase recruitment domain (CARD). It is involved in the viral recognition of double-stranded RNA (ds) and in the regulation of the immune response, [provided by RefSeq, July of 2008] |

TABLE 7B-continued

| DEGs related to the innate immune response, apoptosis and inflammation | |
|---|---|
| ENSECAG 00000010619 | This gene encodes coagulation factor XII that circulates in the blood as a zymogen. This single-chain zymogen is converted to a two-chain serine protease with a heavy chain (alpha factor XIIa) and a light chain. The heavy chain contains two fibronectin-like domains, two epidermal growth factor (EGF)-type domains, a kringle domain and a proline-rich domain, while the light chain contains only a catalytic domain. Upon activation, more cleavages in the heavy chain occur, resulting in the production of the beta factor XIIa light chain and the alpha factor XIIa light chain becomes the beta factor XIIa heavy chain. Pre-kallikrein is cleaved by factor XII to form kallikrein, which then cleaves factor XII into alpha factor XIIa and then into beta factor XIIa. Active factor XIIa participates in the initiation of blood clotting, fibrinolysis and the generation of bradykinin and angiotensin. It activates coagulation factors VII and XI. This gene defects do not cause any clinical symptoms and the only effect is that the blood clotting time is prolonged, [provided by RefSeq, July of 2008] |
| ENSECAG 00000023092 | The FOS gene family consists of 4 members: FOS, FOSB, FOSL1 and FOSL2. These genes encode proteins with leucine zippers that can dimerize with proteins of the JUN family, thus forming the complex of AP-1 transcription factors. As such, FOS proteins have been implicated as regulators of cell proliferation, differentiation, and transformation. Several transcribed variants that encode different isoforms have been found to this gene, [provided by RefSeq, July of 2014] |
| ENSECAG 00000007881 | DEAD-box proteins, characterized by the conserved motif Asp-Glu-Ala-Asp (DEAD), are putative RNA helicases. They are implicated in several cellular processes that involve the alteration of the secondary structure of RNA, such as the initiation of translation, the nuclear and mitochondrial junction and the assembly of the ribosome and spliceosome. Based on their distribution patterns, some members of this family are believed to be involved in embryogenesis, spermatogenesis and cell growth and division. This gene encodes the protein DEAD-box which is upregulated in response to treatment with beta-interferon and an activating compound of the protein kinase C, mezerein. Irreversible reprogramming of melanomas can be achieved by treatment with both agents; treatment with either agent alone achieves a reversible differentiation. The genetic variation in this gene is associated with type 19 insulin-dependent diabetes mellitus. [provided by RefSeq, July of 2012] |
| ENSECAG 00000004433 | This gene encodes a protein containing tetra tropic peptide repeats that were originally identified as induced by treatment with interferon. The coded protein can inhibit viral replication and translational initiation. This gene is located in a cluster on chromosome 10 with five other closely related genes. There is a pseudogene for this gene on chromosome 13. Alternatively, transcribed variants have been observed that encode multiple isoforms, [provided by RefSeq, August of 2012] |
| ENSECAG 00000019115 | The protein coded by this gene it is a subunit of the interleukin 13 receptor. This subunit forms a receptor complex with an alpha IL4 receptor, a subunit shared by the IL13 and IL4 receptors. This subunit serves as a |

TABLE 7B-continued

DEGs related to the innate immune response, apoptosis and inflammation

| | |
|---|---|
| | primary IL13-binding subunit of the IL13 receptor and can also be a component of IL-4 receptors. This protein has been shown to bind to tyrosine kinase TYK2 and therefore can mediate the signaling processes that lead to IL13 and IL4-induced activation of JAK1, STAT3 and STAT6. [provided by RefSeq, July of 2008] |
| ENSECAG 00000000168 | The protein coded by this gene it is a member of the interleukin 1 cytokine family. This cytokine is produced by macrophages activated as a pro-protein, which is proteolytically processed in its active form by caspase 1 (CASP1/ICE). This cytokine is an important mediator of the inflammatory response and is involved in a variety of cellular activities, including cell proliferation, differentiation, and apoptosis. The induction of cyclooxygenase-2 (PTGS2/COX2) by this cytokine in the central nervous system (CNS) is found to contribute to hypersensitivity to inflammatory pain. This gene and eight other genes from the interleukin 1 family form a cluster of cytokine genes on chromosome 2. [provided by RefSeq, July of 2008] |
| ENSECAG 00000017386 | This gene encodes the alpha 1 subunit of the integrin receptors. This protein heterodimerizes with the beta 1 subunit to form a cell surface receptor for collagen and laminin. The heterodimeric receptor is involved in cell-cell adhesion and can play a role in inflammation and fibrosis. The alpha 1 subunit contains an inserted (I) domain of the inserted von Willebrand type I factor, which is thought to be involved in collagen binding, [provided by RefSeq, July of 2008] |
| ENSECAG 00000022909 | Myosin is the important contractile protein that converts chemical energy into mechanical energy through the hydrolysis of ATP. Myosin is the hexameric protein composed of a pair of myosin heavy chains (MYH) and two pairs of non-identical light chains. The heavy chains of myosin are encoded by a multigenic family. In mammals, at least 10 different myosin heavy chain (MYH) isoforms have been described from striated, smooth, and non-muscle cells. These isoforms show expression that is spatially and temporally regulated during development, [provided by RefSeq, July of 2008] |
| ENSECAG 00000025060 | Myosin is the important contractile protein that converts chemical energy into mechanical energy through the hydrolysis of ATP. Myosin is the hexameric protein composed of a pair of myosin heavy chains (MYH) and two pairs of non-identical light chains. This gene is a member of the MYH family and encodes protein with an IQ domain and a myosin head-like domain. This gene mutations have been associated with two congenital contracture syndromes (arthrogriposis), Freeman-Sheldon syndrome and Sheldon-Hall syndrome, [provided by RefSeq, July of 2008 |
| ENSECAG 00000007867 | |
| ENSECAG 00000016691 | This gene encodes a pre-proprotein that is processed into a secreted protein containing domains similar to eukaryotic growth factor (EGF). This protein acts to guide axon growth during neuronal development. Polymorphisms in this gene may be associated with schizophrenia. Alternative splicing results in multiple transcript variants that encode distinct isoforms, [provided by RefSeq, August of 2015] |
| ENSECAG 00000012331 | PARP9 (A member of the POLI (ADP-ribose) polymerase family 9) is a Protein Coding |

TABLE 7B-continued

DEGs related to the innate immune response, apoptosis and inflammation

| | |
|---|---|
| | gene. PARP9-associated diseases include lymphomas and B-cell lymphoma. Among its related pathways are Metabolism and Metabolism of vitamins and water-soluble cofactors. The GO annotations related to this gene include NAD + ADP-ribosyl transferase activity. An important parallel of this gene is PARP14. |
| ENSECAG 00000017146 | Phosphoinositide 3-gamma kinase is a lipid kinase that produces the second lipid messenger phosphatidylinositol 3,4,5-triphosphate. The kinase is composed of a catalytic subunit and one of several regulatory subunits, being mainly activated by receptors coupled to protein G. This gene encodes a regulatory subunit and is distantly related to the phosphoinositide-3-kinase subunit 5 gene, which is located adjacent to this gene on chromosome 7. The ortholog protein in the mouse binds to both the catalytic and G (beta/gamma) subunits and mediates the activation of the kinase subunit downstream of the protein G-coupled receptors. Alternative splicing results in multiple transcription variants, [provided by RefSeq, February of 2014] |
| ENSECAG 00000003462 | The nucleus-binding factor (CBF) is a heterodimeric transcription factor that binds to the central element of many enhancers and promoters. The protein coded by this gene represents the alpha subunit of CBF and is believed to be involved in the development of normal hematopoiesis. Chromosomal translocations involving this gene are well documented and have been associated with several types of leukemia. Three transcribed variants that encode different isoforms have been found for this gene, [provided by RefSeq, July of 2008] |
| ENSECAG 00000011404 | This gene encodes a member of the serum amyloid A family of apolipoproteins. The encoded pre-proprotein is processed proteolytically to generate the mature protein. This protein is the important acute phase protein that is highly expressed in response to inflammation and tissue damage. This protein also plays an important role in HDL metabolism and cholesterol homeostasis. Elevated levels of this protein are associated with chronic inflammatory diseases including atherosclerosis, rheumatoid arthritis, Alzheimer's disease, and Crohn's disease. This protein can also be a potential biomarker for certain tumors. Alternative splicing results in several transcript variants that encode the same protein. A pseudogene of this gene is found on chromosome 11. [provided by RefSeq, February of 2016] |
| ENSECAG 00000010918 | This gene encodes the 140 kDa protein that is stored in the alpha granules of the platelets and in the Weibel-Palade bodies of the endothelial cells. This protein redistributes itself to the plasma membrane during platelet activation and degranulation and mediates the interaction of activated endothelial cells or platelets with leukocytes. The membrane protein is a calcium-dependent receptor that binds to sialylated forms of Lewis blood group carbohydrate antigens on neutrophils and monocytes. Alternative splice variants may occur but are not well documented, [provided by RefSeq, July of 2008] |
| ENSECAG 00000001249 | This gene encodes a member of the STAT-induced STAT inhibitor (SSI), also known as cytokine signaling suppressor (SOCS), family. Members of the SSI family are cytokine-inducible negative regulators of cytokine signaling. The expression of this gene is |

TABLE 7B-continued

DEGs related to the innate immune response, apoptosis and inflammation

| | | |
|---|---|---|
| | | induced by several cytokines, including IL6, IL10 and interferon (IFN)-gamma. The protein coded by this gene can bind to JAK2 kinase and inhibit JAK2 kinase activity. Studies of the counterpart of mice of this gene suggested the roles of this gene in the negative regulation of fetal liver hematopoiesis and placental development, [provided by RefSeq, July of 2008] |
| | ENSECAG 00000021565 | This nuclear gene encodes the mitochondrial protein tyrosine aminotransferase that is present in the liver and catalyzes the conversion of L-tyrosine to p-hydroxyphenylpyruvate. Mutations in this gene cause tyrosinemia (type II, Richner-Hanhart syndrome), a disorder accompanied by important skin and corneal lesions, with possible mental retardation. A tyrosine aminotransferase regulatory gene is linked to X. [provided by RefSeq, July of 2008] |
| | ENSECAG 00000011303 | This gene product is a member of the transcription enhancing factor (TEF) family of transcription factors, which contains the DNA-binding domain of TEA/ATTS. It is preferentially expressed in skeletal muscle, and it binds to the regulatory element M-CAT found in promoters of specific muscle genes to direct its gene expression. Alternatively processed transcripts encoding distinct isoforms, some of which are translated using a non-AUG initiation codon (UUG), have been described for this gene, [provided by RefSeq, July of 2008] |
| | ENSECAG 00000008923 | The protein coded by this gene it is a disulfide-bound homotrimeric protein subunit. This protein is an adhesive glycoprotein that mediates cell-cell and cell-matrix interactions. This protein can bind to fibrinogen, fibronectin, laminin, type V collagen and alpha-V/beta-1 integrins. This protein has been shown to play a role in platelet aggregation, angiogenesis, and tumorigenesis. [provided by RefSeq, July of 2008] |
| | ENSECAG 00000017436 | This gene encodes a receptor belonging to the Ig superfamily expressed in myeloid cells. This protein amplifies inflammatory responses mediated by neutrophils and monocytes, triggered by bacterial and fungal infections, stimulating the release of pro-inflammatory chemokines and cytokines, as well as increasing the surface expression of cell activation markers. Alternatively, transcribed variants processed encoding different isoforms were observed for this gene. [Provided by RefSeq, June of 2011] |

TABLE 7C

DEGs related to innate immune response, apoptosis, and inflammation.

| gene_id | symbol | entrezid | logFC6 | fdr6 | logFC12 | fdr12 | median1 | median2 | median3 |
|---|---|---|---|---|---|---|---|---|---|
| ENSECAG 00000011042 | BATF3 | 55509 | 3.137442 | 0.009959 | 2.910096 | 0.054986 | 0.370764 | 4.203848 | 4.039599 |
| ENSECAG 00000020701 | CAV3 | 859 | −3.0363 | 0.007186 | −6.6813 | 0.000663 | 2.260559 | 0.273368 | 0 |
| ENSECAG 00000004945 | CCR7 | 1236 | 2.651571 | 0.000812 | 2.359309 | 0.020078 | 0.178883 | 2.951747 | 3.137418 |
| ENSECAG 00000022526 | CDH15 | 1013 | −2.61649 | 0.019906 | −1.70207 | 0.4241 | 0.845054 | 0.068342 | 0.241768 |
| ENSECAG 00000011726 | EIF2AK2 | 5610 | 2.400155 | 0.004067 | 2.959487 | 0.001208 | 0.381304 | 1.717853 | 2.113246 |
| ENSECAG 00000023546 | ETV6 | 2120 | 1.794723 | 0.004139 | 1.871016 | 0.014637 | 1.034732 | 4.092317 | 4.68746 |

TABLE 7C-continued

DEGs related to innate immune response, apoptosis, and inflammation.

| | | | | | | | | | |
|---|---|---|---|---|---|---|---|---|---|
| ENSECAG 00000000214 | IL18RAP | 8807 | 2.81657 | 0.03053 | 2.593437 | 0.127649 | 0.78569 | 3.592823 | 1.950324 |
| ENSECAG 00000010973 | IL7R | 3575 | 2.531562 | 0.048441 | 2.22672 | 0.257395 | 0 | 1.180559 | 0.833432 |
| ENSECAG 00000011041 | MYLK2 | 85366 | −5.15164 | 0.001693 | −5.67185 | 0.019194 | 4.097029 | 0.068342 | 0 |
| ENSECAG 00000006637 | NECTIN3 | 25945 | 1.287059 | 0.045707 | 1.113063 | 0.270904 | 1.274145 | 2.630473 | 1.991054 |
| ENSECAG 00000019830 | NLRC4 | 58484 | 5.502526 | 0.001787 | 5.687202 | 0.005073 | 0 | 0.78052 | 0.864274 |
| ENSECAG 00000017662 | NLRP12 | 91662 | 3.400355 | 0.011373 | 2.297243 | 0.309324 | 0 | 1.395778 | 1.236851 |
| ENSECAG 00000008809 | OAS3 | 4940 | 1.716008 | 0.072453 | 2.111503 | 0.059172 | 1.029133 | 2.470657 | 4.496043 |
| ENSECAG 00000023084 | PRKCQ | 5588 | −1.53087 | 0.042897 | −3.02147 | 0.007044 | 1.540639 | 0.571363 | 0 |

| gene_id | refseq |
|---|---|
| ENSECAG 00000011042 | This gene encodes a member of the basic leucine zipper protein family. The coded protein functions as a transcriptional repressor when heterodimerizing with JUN. The protein may play a role in the suppression of interleukin-2 and matrix-1 metalloproteinase transcription [provided by RefSeq, February of 2009], |
| ENSECAG 00000020701 | This gene encodes a member of the caveolin family, which functions as a component of the plasma caveola membranes found in most cell types. Caveolin proteins are proposed to be scaffold proteins to organize and concentrate certain molecules that interact with caveolin. The mutations identified in this gene lead to interference with protein oligomerization or intra-cellular routing, interrupting the formation of caveola and resulting in type-1C muscular dystrophy (LGMD-1C), hyperCKemia or undulatory muscle disease (RMD). Alternative splicing was identified for this locus, with the inclusion or exclusion of a differentiated intron. Furthermore, transcripts use multiple polyA sites and contain two potential translation initiation sites, [provided by RefSeq, July of 2008] |
| ENSECAG 00000004945 | The protein coded by this gene is a member of the family of receptors coupled to protein G. This receptor has been identified as an Epstein-Barr (EBV) virus-induced gene, and it is believed to be a mediator of the effects of EBV on B lymphocytes. This receptor is expressed in several lymphoid tissues and activates B and T lymphocytes. It has been shown to control the migration of memory T cells to inflamed tissues, as well as stimulating the maturation of dendritic cells. Ligand 19 of chemokine (motif C-C) (CCL19/ECL) has been described as being a specific ligand for this receptor. The signals mediated by this receptor regulate T cell homeostasis in the lymph nodes and can also act on the activation and polarization of T cells and in the pathogenesis of chronic inflammation. Alternative processing of this gene results in multiple transcription variants, [provided by RefSeq, September of 2014] |
| ENSECAG 00000022526 | This gene is a member of the cadherin gene superfamily, which encodes calcium-dependent intercellular adhesion glycoproteins. Cadherins consist of an extracellular domain containing 5 cadherin domains, a transmembrane region, and a conserved cytoplasmic domain. The transcripts of this particular cadherin are expressed in myoblasts and upregulated in myotubule-forming cells. The protein is believed to be essential for the control of |

TABLE 7C-continued

DEGs related to innate immune response, apoptosis, and inflammation.

| | |
|---|---|
| | morphogenetic processes, specifically myogenesis, and can provide a stimulus for the terminal differentiation of muscle cells, [provided by RefSeq, July of 2008] |
| ENSECAG 00000011726 | The protein coded by this gene is a serine/threonine protein kinase which is activated by autophosphorylation after binding to dsRNA. The activated form of the coded protein can phosphorylate the EIF2S1 translation initiation factor, which in turn inhibits protein synthesis. This protein is also activated by manganese and heparin ions. Three transcribed variants that encode two different isoforms have been found for this gene, [provided by RefSeq, October of 2011] |
| ENSECAG 00000023546 | This gene encodes a transcription factor from the ETS family. The product of this gene contains two functional domains: a pointed N-terminal domain (PNT) that is involved in protein-protein interactions with itself and other proteins, and a C-terminal DNA binding domain. Studies of genetic knockout in mice suggest that it is necessary for hematopoiesis and maintenance of the developing vascular network. This gene is known to be involved in a large number of chromosomal rearrangements associated with congenital leukemia and fibrosarcoma, [provided by RefSeq, September of 2008] |
| ENSECAG 00000000214 | The protein coded by this gene is an accessory subunit of the heterodimeric receptor for interleukin 18 (IL18), a pro-inflammatory cytokine involved in inducing cell-mediated immunity. This protein increases IL18 binding activity of the IL18 receptor and plays a role in IL18 signaling. Mutations in this gene are associated with Crohn's disease and inflammatory bowel disease and susceptibility to celiac disease and leprosy. Alternatively, processed transcribed variants of this gene have been described, but its full-length nature is not known, [provided by RefSeq, February of 2014] |
| ENSECAG 00000010973 | The protein coded by this gene is a receptor for interleukin 7 (IL7). The function of this receptor requires the gamma chain of the interleukin 2 receptor (IL2RG), which is a common gamma chain shared by the receptors of various cytokines, including interleukins 2, 4, 7, 9 and 15. This protein has been shown to play a critical role in V (D) J recombination during lymphocyte development. Defects in this gene may be associated with severe combined immunodeficiency (SCID). Alternatively, processed transcribed variants were found, [provided by RefSeq, December of 2015] |
| ENSECAG 00000011041 | This gene encodes a myosin light chain kinase, a calcium/calmodulin-dependent enzyme, which is exclusively expressed in adult skeletal muscle, [provided by RefSeq, July of 2008] |
| ENSECAG 00000006637 | This gene encodes a member of the nectin family of proteins, which function as adhesion molecules at adherent junctions. This family member interacts with other nectin-like proteins and with afadin, a filamentous actin-binding protein involved in the regulation of directional motility, cell proliferation and survival. This gene plays a role in eye development involving the ciliary body. Mutations in this gene are believed to result in congenital eye defects. Alternative splicing results in multiple transcription variants, [provided by RefSeq, August of 2011] |
| ENSECAG 00000019830 | This gene encodes a member of the NLR family containing caspase recruitment |

TABLE 7C-continued

DEGs related to innate immune response, apoptosis, and inflammation.

| | | |
|---|---|---|
| | | domain. Family members play essential roles in innate immune response to a wide range of pathogenic organisms, tissue damage and other cellular stresses. Mutations in this gene result in autoinflammation with childhood enterocolitis. Alternative splicing results in multiple transcription variants, [provided by RefSeq, October of 2014] |
| | ENSECAG 00000017662 | This gene encodes a CATERPILLER family member of cytoplasmic proteins. The coded protein, which contains an N-terminal pyrin domain, a NACHT domain, a NACHT-associated domain, and a C-terminal leucine-rich repeat region, works as a mitigating factor in inflammation by suppressing inflammatory responses in activated monocytes. Mutations in this gene cause type 2 cold familial autoinflammatory syndrome. Alternative splicing results in multiple transcription variants, [provided by RefSeq, March of 2013] |
| | ENSECAG 00000008809 | This gene encodes an enzyme included in the family 2',5' oligoadenylate synthase. This enzyme is induced by interferons and catalyzes oligomers 2',5' adenosine in order to bind and activate RNase L. This family of enzymes plays a significant role in inhibiting cellular protein synthesis and resistance to viral infection, [provided by RefSeq, July of 2008] |
| | ENSECAG 00000023084 | The protein kinase C (PKC) is a family of serine and threonine-specific protein kinases that can be activated by calcium and by the second diacylglycerol messenger. PKC family members phosphorylate a wide variety of protein targets and are known to be involved in several cell signaling pathways. Members of the PKC family also serve as primary receptors for phorbol esters, a class of tumor promoters. Each member of the PKC family has a specific expression profile and is believed to play a distinct role. The protein coded by this gene is one of the members of the PKC family. It is a protein kinase which is calcium independent and phospholipid dependent. This kinase is important for the activation of T cells. It is necessary for the activation of the NF kappa B and AP-1 transcription factors and can link the T cell receptor (TCR) signaling complex to the activation of the transcription factors, [provided by RefSeq, July of 2008] |

The invention claimed is:

1. A compound comprising a polypeptide sequence consisting of one of Seq ID Nos: 2-9.

2. A pharmaceutical composition comprising at least one compound of claim 1 and one pharmaceutically acceptable excipient.

3. A method of making a medicine comprising incorporating the compound of claim 1 into a pharmaceutical.

* * * * *